Figure 1:
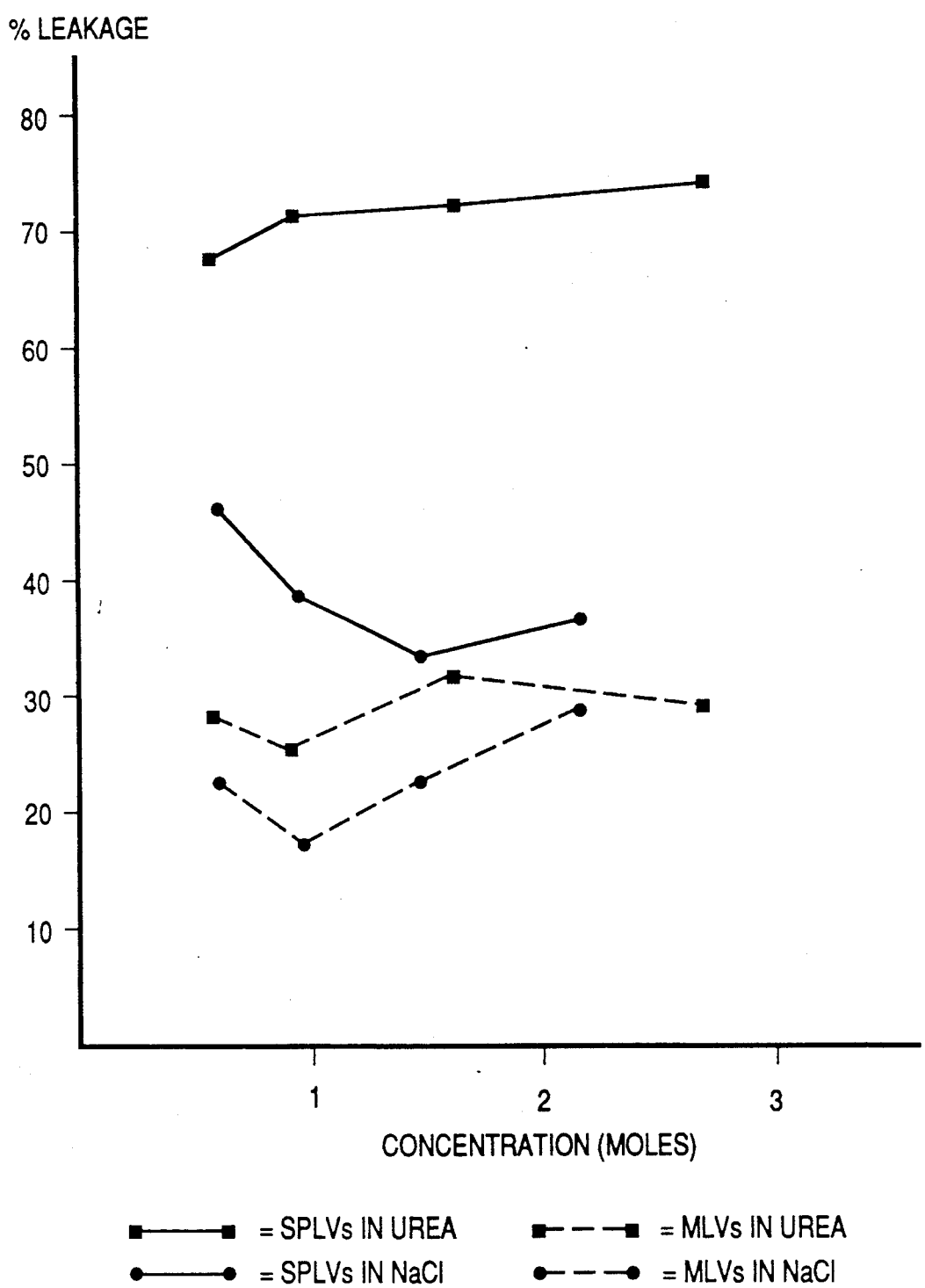

United States Patent [19]

Lenk et al.

[11] Patent Number: 5,030,453

[45] Date of Patent: * Jul. 9, 1991

[54] STABLE PLURILAMELLAR VESICLES

[75] Inventors: Robert P. Lenk, Lambertville; Michael W. Fountain, Griggstown, both of N.J.; Andrew S. Janoff, Yardley, Pa.; Mircea C. Popescu, Plainsboro, N.J.; Steven J. Weiss, Hightstown, N.J.; Richard S. Ginsberg, Monroe Township,, N.J.; Marc J. Ostro, Griggstown, N.J.; Sol M. Gruner, Lawrenceville, N.J.

[73] Assignee: The Liposome Company, Inc., Princeton, N.J.

[*] Notice: The portion of the term of this patent subsequent to Jun. 11, 2002 has been disclaimed.

[21] Appl. No.: 660,573

[22] Filed: Oct. 12, 1984

Related U.S. Application Data

[63] Continuation-in-part of Ser. No. 633,481, Jul. 26, 1984, abandoned, and a continuation-in-part of Ser. No. 476,496, Mar. 24, 1983, Pat. No. 4,522,803, and a continuation-in-part of Ser. No. 521,176, Aug. 8, 1983, Pat. No. 4,588,578.

[51] Int. Cl.⁵ ............................................. A61K 37/22
[52] U.S. Cl. ..................................................... 424/450
[58] Field of Search ................. 424/38, 450; 264/4.1, 264/4.3, 4.6

[56] References Cited

U.S. PATENT DOCUMENTS 4,522,803 1/1985 Lenk et al. ............................ 424/38

FOREIGN PATENT DOCUMENTS 8303383 10/1983 World Int. Prop. O. ............ 424/38

Primary Examiner—Stanley J. Friedman
Assistant Examiner—Raymond J. Henley, III
Attorney, Agent, or Firm—Allen Bloom; Thomas M. Saunders; Ronald G. Ort

[57] ABSTRACT

A new and substantially improved type of lipid vesicle, called stable plurilamellar vesicles (SPLVs), are described, as well as the process for making the same and X-ray diffraction methods for identifying the same. SPLVs are characterized by lipid bilayers enclosing aqueous compartments containing one or more entrapped solutes, the concentration of such solutes in each aqueous compartment being substantially equal to the concentration of solutes used to prepare the SPLVs. The bilayers of SPLVs are substantially non-compressed. SPLVs are stable during storage and can be used in vivo for the sustained release of compounds and in the treatment of disease.

23 Claims, 20 Drawing Sheets

FIG. 2
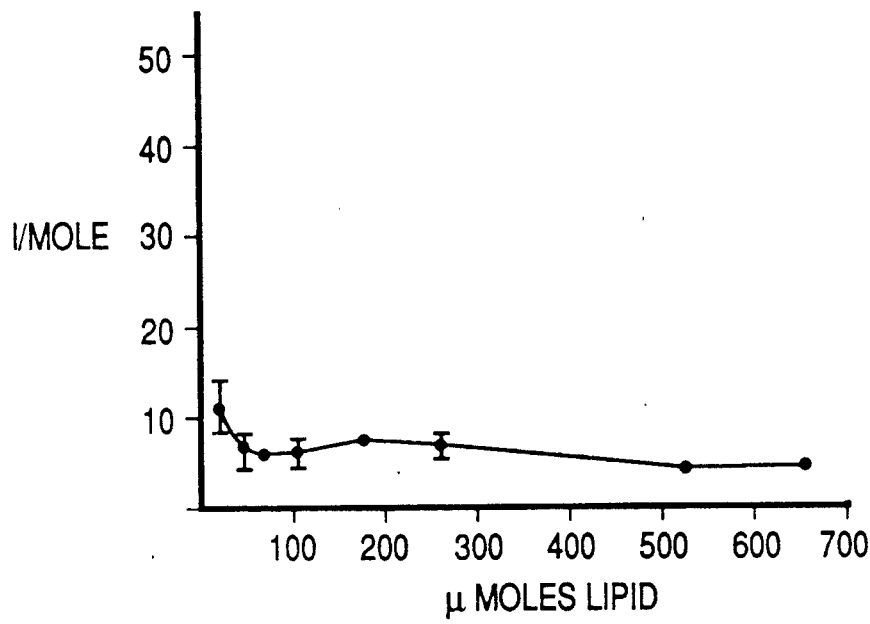
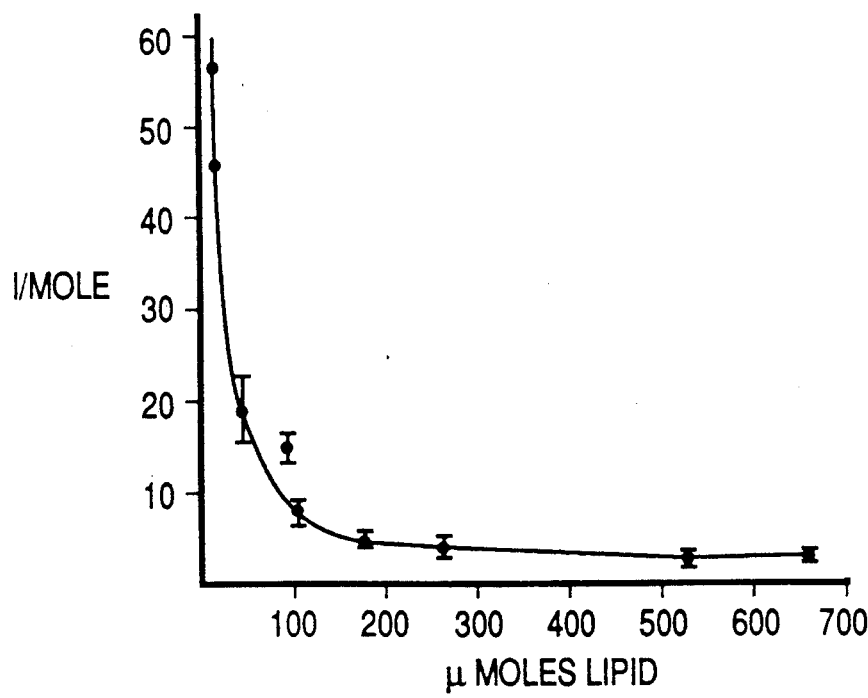

FIG. 6
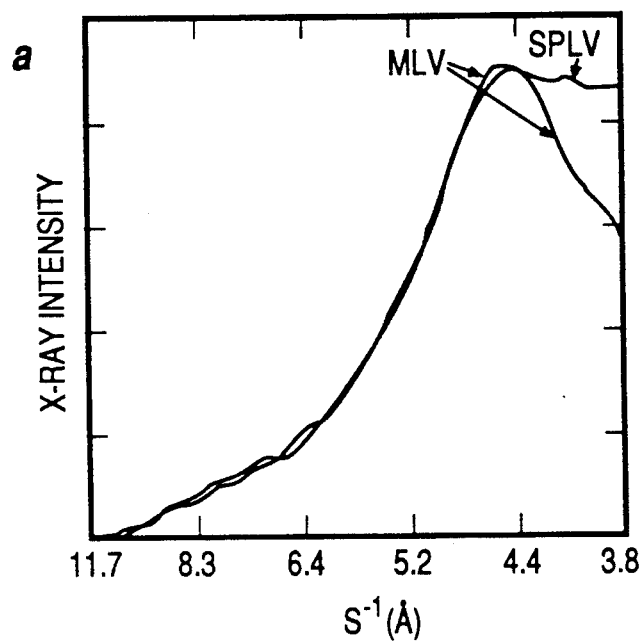
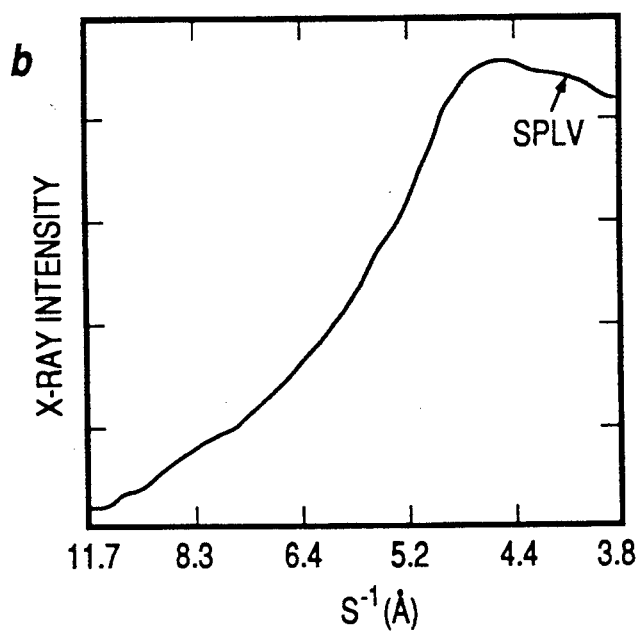

FIG. 17
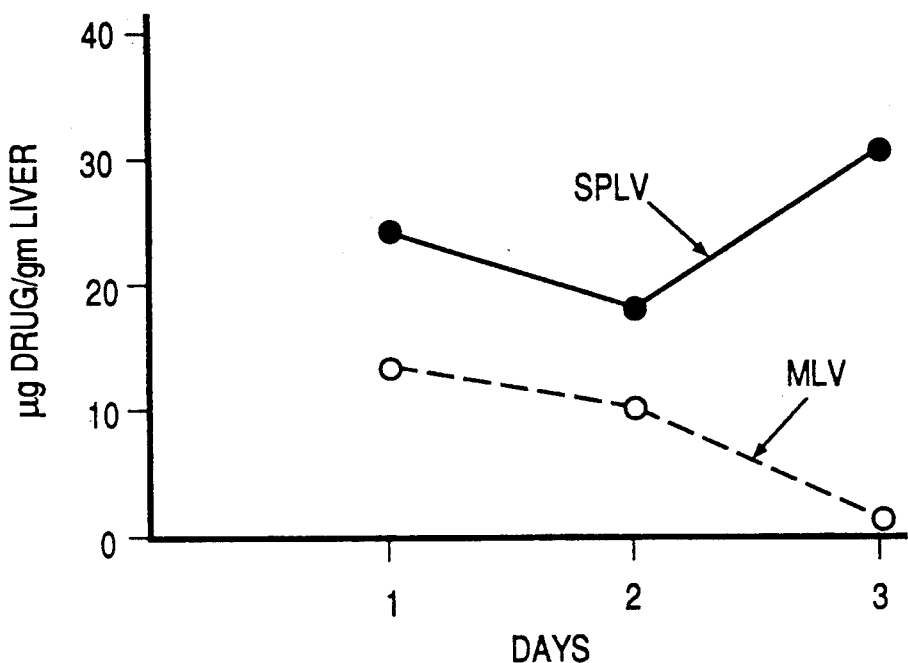
a) LIVER
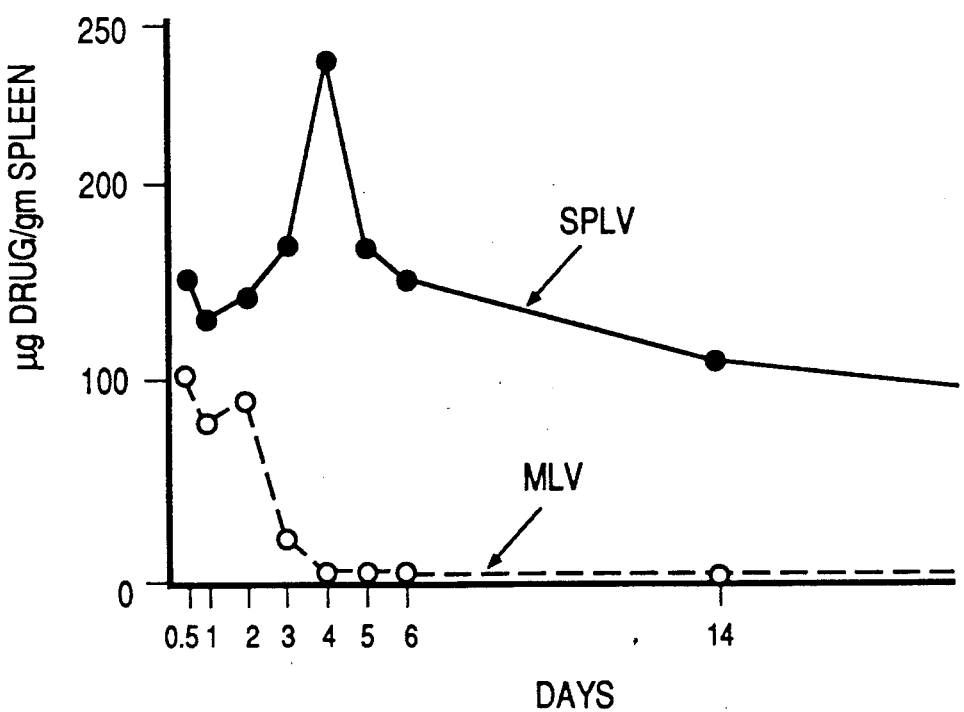
b) SPLEEN

FIG. 19

SURVIVING BRUCELLA CANIS IN VARIOUS TISSUES OF
MICE AFTER TWO-STAGE TREATMENT WITH STREPTOMYCIN

A: CONTROL
B: STREPTOMYCIN
C: SPLV - ENTRAPPED STREPTOMYCIN

FIG. 20

SURVIVING BRUCELLA ABORTUS IN SPLEENS OF GUINEA
PIGS AFTER TWO-STAGE TREATMENT WITH STREPTOMYCIN

STABLE PLURILAMELLAR VESICLES

This is a continuation-in-part of application Ser. No. 06/633,481, filed July 26, 1984 now abandoned and a continuation-in-part of application Ser. No. 06/476,496, filed Mar. 24, 1983 now U.S. Pat. No. 4,522,803 and a continuation-in-part of application Ser. No. 06/521,176, filed Aug. 8, 1983 now U.S. Pat. No. 4,588,578.

TABLE OF CONTENTS

1. Field of the Invention
2. Background of the Invention
   2.1. Liposomes
   2.2. Uses of Liposomes
3. Summary of the Invention
4. Brief Description of the Figures
5. Detailed Description of the Invention
   5.1. Preparation of SPLVs
      5.1.1. Monophasic Solvent System Process
      5.1.2. Emulsification Process
      5.1.3. SPLV Constituents
   5.2. Characterization of SPLVs
      5.2.1. Stability of SPLVs in Storage
      5.2.2. Stability of SPLVs in Other Environments
      5.2.3. Entrapment of Active Material by SPLVs
      5.2.4. Effect of Varying the Initial Lipid to Aqueous Ratio
      5.2.5. Volume of SPLVs
      5.2.6. Buoyant Density of SPLVs
      5.2.7. Osmotic Properties of SPLVs
      5.2.8. Electron Spin Resonance
      5.2.9. X-ray Diffraction
         5.2.9.1. X-ray Diffraction Methods
         5.2.9.2. X-ray Diffraction Signatures
         5.2.9.3. Long Spacing Signature
         5.2.9.4. Relation of Long Spacing Signature to the Osmotic Properties of SPLVs and MLVs
         5.2.9.5. Solute Distribution in SPLVs vs. MLVs
         5.2.9.6. Identification of SPLVs
         5.2.9.7. Interpretation of Results
   5.3. Uses of SPLVs
      5.3.1. Delivery of Bioactive Compounds
         5.3.1.1. Delivery In Vitro
         5.3.1.2. Delivery In Vitro
      5.3.2. Treatment of Pathologies
6. Example: Preparation of SPLVs by the Monophasic Solvent System Processes
   6.1. SPLVs Containing Tetracyclines
   6.2. SPLVs Containing Gentamicin and Nafcillin
   6.3. SPLVs Containing Gentamicin
   6.4. SPLVs Containing Chloramphenicol
   6.5. SPLVs Containing Tobramycin
   6.6. SPLVs Containing Ticarcillin
   6.7. SPLVs Containing Ticarcillin and Tobramycin
   6.8. Alternative Methods of Preparaing SPLVs
   6.9. Preparation of SPLVs Using Various Solvent System
7. Preparation of SPLVs by the Emulsification Processes
   7.1. SPLVs Containing Antibiotics
   7.2. Preparation of SPLVs Containing Gentamicin or Nafcillin
   7.3. Preparation of SPLVs Containing Both Gentamicin and Nafcillin
   7.4. SPLVs Containing Gentamicin and Clindamycin
   7.5. SPLVs Containing Other Membrane Constituents
   7.6. SPLVs Containing Pilocarpine
   7.7. SPLVs Prepared With and Without BHT
8. Example: SPLV Mediated Delivery In Vitro
9. Example: Treatment of Intracellular Infections
   9.1. Effect of a Single Treatment of B. Canis Infection Using SPLV-entrapped Entibiotic
   9.2. Effect of Multiple Treatment of B. Canis Infection Using SPLV-entrapped Antibiotic
   9.3. Effectiveness of Treatments Using MLVs as Compared to SPLVs
   9.4. Effect of Various SPLV-entrapped Antibiotics On Treatment of Infection
   9.5. Treatment of Dogs Infected with B. Canis
   9.6. Treatment of B. Abortus in Guinea Pigs
   9.7. Treatment of B. Abortus Infection in Cows
10. Example: Treatment of Systemic Infection
    10.1. Effect of Single Treatment of S. Typhimurium Infection Using SPLV-entrapped Antibiotics
    10.2. Effect of Multiple Treatment of S. Typhimurium Infection Using SPLV-entrapped Antibiotics
    10.3. Example: Enhancement of Antibacterial Activity in Treating Salmonella Typhimurium Infections Using SPLVs Containing Gentamicin and Nafcillin
    10.4. Example: Enhancement of Antibacterial Activity in Treating Salmonellosis Using SPLVs Containing Gentamicin and Nafcillin
    10.5. Example: Enhancement of Antibacterial Activity in Treating Salmonella Typhimurium Infections Using SPLVs Containing Gentamicin and Nafcillin
11. Example: Treatment of Ocular Afflictions
    11.1. Treatment of Infectious Keratoconjunctivitis in Mice
    11.2. Treatment of Rabbit Conjunctiva Using SPLV-entrapped Antibiotic
    11.3. Treatment of Keratoconjunctivitis Resulting From Subcutaneous Infections
    11.4. Evaluation of the Effectiveness of SPLVs as Compared to Liposome Preparations in the Treatment of Ocular Infections
12. Example: Treatment of Viral Infections
    12.1. Treatment of Lethal Lymphocytic Chorio-Meningitis Virus Infections in Mice
13. Example: Enhancement of Antibacterial Activity in Treating Corynebacterium Renale Pyelonephritis Using SPLVs Containing Gentamicin and Nafcillin
    13.1. Preparation of SPLVs
    13.2. Infection of Mice Using Corynebacterium Renale
    13.3. Treatment of Infected Mice
14. Example: Enhancement of Antibacterial Activity in Treating Pseudomonas Aeruginosa Pyelonephritis Using SPLVs Containing Tobramycin and Ticarcillin
    14.1. Treatment of Infected Rats
    14.2. Effects of Different Treatments of Infected Rats
15. Example: Enhancement of Antibacterial Activity Against Clostridium Novyi Using SPLVs Containing Gentamicin and Clindamycin
    15.1. Infection of Mice Using Clostridium Novyi
    15.2. Treatment of Infected Mice

1. FIELD OF THE INVENTION

This invention relates to liposomes and their uses as carriers. More specifically, it relates to a new type of lipid vesicle having unique properties which confer special advantages such as increased stability and high entrapment efficiency.

The compositions and methods described herein have a wide range of applicability to fields such as carrier systems and targeted delivery systems. The practice of the present invention is demonstrated herein by way of example for the treatment of brucellosis, the treatment of a systemic Salmonella infection, the treatment of ocular infections, the treatment of pyelonephritis and the treatment of lymphocytic meningitis virus infections.

2. BACKGROUND OF THE INVENTION

2.1. Liposomes

Liposomes are completely closed bilayer membranes containing an entrapped aqueous phase. Liposomes may be any variety of unilamellar vesicles (possessing a single membrane bilayer) or multilamellar vesicles (onion-like structures characterized by concentric membrane bilayers each separated from the next by a layer of water).

The original liposome preparations of Bangham et al. (1965, J. Mol. Biol. 13:238–252) involved suspending phospholipids in an organic solvent which was then evaporated to dryness leaving a waxy deposit of phospholipid on the reaction vessel. Then an appropriate amount of aqueous phase was added, the mixture was allowed to "swell", and the resulting liposomes which consisted of multilamellar vesicles (hereinafter referred to as MLVs) were dispersed by mechanical means. The structure of the resulting membrane bilayer is such that the hydrophobic (non-polar) "tails" of the lipid orient toward the center of the bilayer while the hydrophilic (polar) "heads" orient towards the aqueous phase. This technique provided the basis for the development of the small sonicated unilamellar vesicles (hereinafter referred to as SUVs) described by Papahadjapoulos and Miller (1967, Biochim. Biophys. Acta. 135:624—638). These "classical liposomes" (MLVs and SUVs), however, had a number of drawbacks not the least of which was a low entrapment of aqueous space markers.

Efforts to increase the entrapped volume involved first forming inverse micelles or liposome precursors, i.e., vesicles containing an aqueous phase surrounded by a monolayer of lipid molecules oriented so that the polar head groups are directed towards the aqueous phase. Liposome precursors are formed by dispersing the aqueous solution to be entrapped in a solution of polar lipid in an organic solvent. The liposome precursors are then added to an aqueous medium and evaporated in the presence of excess lipid. The resultant liposomes, consisting of an aqueous phase entrapped by a single lipid bilayer are dispersed in aqueous phase (see U.S. Pat. No. 4,224,179 issued Sept. 23, 1980 to M. Schneider).

In another attempt to maximize the efficiency of entrapment Papahadjopoulos (U.S. Pat. No. 4,235,871 issued Nov. 25, 1980) describes a "reverse-phase evaporation process" for making unilamellar and oligolamellar lipid vesicles also known as reverse-phase evaporation vesicles (hereinafter referred to as REVs). According to this procedure, the aqueous material to be entrapped is added to a mixture of polar lipid in an organic solvent. Then a homogeneous water-in-oil type of emulsion is formed and the organic solvent is evaporated until a gel is formed. The gel is then converted to a suspension by dispersing the gel-like mixture in an aqueous media. The REVs produced consist mostly of unilamellar vesicles (large unilamellar vesicles or LUVs) and some oligolamellar vesicles which are characterized by only a few concentric bilayers with a large internal aqueous space. Certain permeability properties of REVs were reported to be similar to those of MLVs and SUVs (see Szoka and Papahadjopoulos, 1978, Proc. Natl. Acad. Sci. U.S.A. 75:4194–4198).

Liposomes which entrap a variety of compounds can be prepared, however, stability of the liposomes during storage is invariably limited. This loss in stability results in leakage of the entrapped aqueous soluble compound from the liposomes into the surrounding media, and can also result in contamination of the liposome contents by permeation of materials from the surrounding media into the liposome itself. As a result the storage life of traditional liposomes is very limited. Attempts to improve stability involved incorporating into the liposome membrane certain substances (hereinafter called "stabilizers") which affect the physical properties of the lipid bilayers (e.g., steroid groups). However, many of these substances are relatively expensive and the production of such liposomes is not costeffective.

In addition to the storage problems of traditional liposomes a number of compounds cannot be incorporated into these vesicles. MLVs can only be prepared under conditions above the phase-transition temperature of the lipid membrane. This precludes the incorporation of heat labile molecules within liposomes that are composed of phospholipids which exhibit desirable properties but possess long and highly saturated side chains.

2.2. Uses of Liposomes

Much has been written regarding the possibilities of using liposomes for drug delivery systems. In a liposome drug delivery system the medicament is entrapped during liposome formation and then administered to the patient to be treated. Typical of such disclosures are U.S. Pat. No. 3,993,754 issued on Nov. 23, 1976, to Rahman and Cerny, and U.S. Pat. No. 4,145,410 issued on Mar. 20, 1979, to Sears, U.S. Pat. No. 4,235,871 issued Nov. 25, 1980, to Papahadjopoulos and Szoka and U.S. Pat. No. 4,224,179, issued Sept. 23, 1980 to Schneider.

Desirable features of drug delivery systems depend upon the condition being treated. For example, when treating conditions which require maintenance doses of medication, resistance to rapid clearance of the drug accompanied by a sustained release of the drug which will prolong the drug's action increases the effectiveness of the drug and allows the use of fewer administrations. However, if one is treating an intracellular infection, the maintenance of stability in biological fluids, until the point that the liposome is internalized by the infected cell, is critical as is release of the liposome entrapped drug in its bio-active form. Some of the problems encountered in using liposome preparations in vivo include the following:

(1) Liposome-entrapped materials leak when the liposomes are in contact with body fluids. This has been attributed to the removal of the liposomal phospholipids by plasma lipoproteins, or to the degradation of the liposome membrane by phospholipases, among other reasons. A result of the degradation of the liposomes in vivo is that almost all the liposomal contents are released in a short period of time, therefore, sustained release and resistance of the drug to clearance are not achieved.

(2) On the other hand, to effect a time release of the entrapped material, if a very stable liposome is used in vivo (i.e., liposomes which do not leak when in contact with body fluids in vivo or in vitro), then the liposomal contents will not be released as needed. As a result, these stable liposomes are ineffective as time-release carriers of therapeutic substances in vivo because the sustained release or the ability to release the liposomal contents when necessary is not accomplished.

(3) Liposomes are internalized by the phagocytic cells of the reticuloendothelial system (RES), and, therefore, are cleared from the system rapidly, rendering the entrapped drug largely ineffective against diseases involving cells other than the RES. On the other hand, because cells of the RES phagocytose liposomes, liposome entrapped drugs may be very useful in treating intracellular infections of the RES. However, after phagocytosis, the liposomal contents are packaged within lysosomes of the phagocytic cell and very often the degradative enzymes contained within the lysosome will degrade the entrapped compound or render the compound inactive by altering its structure or modifying the compound at its active site.

(4) The liposome carriers normally used in delivery systems are expensive and production is not cost-effective. For example, an improved method for the chemotherapy of leishmanial infections using liposome encapsulated anti-leishmanial drugs has been reported by Steck and Alving in U.S. Pat. No. 4,186,183 issued on Jan. 29, 1980. The liposomes used in the chemotherapy contained a number of stabilizers which increased the stability of the liposomes in vivo. However, as previously mentioned, these stabilizers are expensive and the production of liposomes containing these stabilizers is not cost-effective.

(5) Ultimately, the problem encountered in the use of liposomes as carriers in drug delivery systems is the inability to effect a cure of the disease being treated. In addition to rapid clearance and degradation of the entrapped compound, a number of other explanations for the inability to cure diseases are possible. For instance, the liposomes may not deliver a dose which is effective due to the low percentage of entrapment of active compound into the vesicles when prepared.

3. SUMMARY OF THE INVENTION

This invention presents a new and substantially improved type of lipid vesicles which hereinafter will be referred to as stable plurilamellar vesicles (SPLVs). Aside from being structurally different from conventional liposomes (i.e., MLVs, SUVs and REVs or LUVs), SPLVs are also prepared differently, possess unique properties, have very different pharmacological and pharmacokinetic effects, and present a variety of different advantages when compared to conventional liposomes. As a result of these differences, SPLVs overcome many of the problems presented by conventional lipid vesicles heretofore available.

A heterogeneous mixture of plurilamellar lipid vesicles is realized when SPLVs are synthesized. Evidence indicates that the lipids in the SPLVs are organized in a novel supramolecular structure. Many of the lipid vesicles possess a high number of bilayers, occasionally in excess of one hundred.

Contrary to current assumptions regarding the distribution of solutes within MLVs, experimental evidence presented herein demonstrates that there is an uneven distribution of solutes in the vesicle compartments such that an osmotic gradient exists in MLVs (i.e., solute is depleted in some of the compartments of the MLV). This gradient causes a stress on the bilayers which creates what we call a compressed vesicle. This compression and stress may be responsible for many of the problems associated with MLVs such as leakage of entrapped compounds, instability during storage, ineffectiveness when used to deliver entrapped compounds in vivo, etc. In complete contrast to MLVs, the SPLVs of the present invention are characterized by lipid bilayers enclosing aqueous compartments containing one or more entrapped solutes, the concentration of such solutes in each aqueous compartment being substantially equal to the concentration of solute used to prepare the SPLV. As a result the SPLVs are not under an appreciable osmotic stress and, therefore, are not compressed.

The properties of SPLVs include: (1) a concentration of entrapped solute in each of the aqueous compartments of SPLVs which is substantially equal to the concentration of solute used to prepare the SPLVs; (2) substantially non-compressed bilayers; (3) the entrapment of materials at a high efficiency; (4) X-ray diffraction signatures that differ from that of MLVs; (5) the ability to cure certain diseases which other drug-vesicle combinations cannot cure; (6) greatly increased stability of the SPLVs during storage in buffer; (7) the increased ability of SPLVs to withstand harsh physiologic environments; (8) the ability to stick to tissues and cells for prolonged periods of time; (9) the ability to release entrapped material slowly in body fluids; (10) the delivery and ultimate dispersal of the liposomal contents throughout the cytosol of the target cell; (11) the release of compounds in their bioactive forms in vivo and (12) improved cost-effectiveness in preparation.

Stable plurilamellar vesicles of this invention may contain a phosphatidylcholine as a major component of the vesicles.

Stable plurilamellar vesicles of this invention may contain an anti-oxidant such as butylated hydroxytoluene as a component of the vesicles.

Stable plurilamellar vesicles of this invention may contain a protein entrapped within the vesicle.

Stable plurilamellar vesicles of this invention may contain an antibacterial compound, antifungal compound, antiparasitic compound, and antiviral compound entrapped within the vesicle.

Stable plurilamellar vesicles of this invention may contain a tumoricidal compound, toxin, cell receptor binding molecule, or immunoglobulin entrapped within the vesicle.

Stable plurilamellar vesicles of this invention may contain an anti-inflammatory compound, anti-glaucoma compound, mydriatic compound, or local anesthetic entrapped within the vesicle.

Stable plurilamellar vesicles of this invention may contain an enzyme, hormone, neurotransmitter, immunomodulator, nucleotide, or cyclic adenosine monophosphate entrapped within the vesicle.

Stable plurilamellar vesicles of this invention may contain a dye, fluorescent compound, radioactive compound, or radio-opaque compound entrapped within the vesicle.

Stable plurilamellar vesicles of this invention may contain a cosmetic preparation, a fragrance or a flavor entrapped within the vesicle.

Due to the unique properties of SPLVs they are particularly useful as carriers in delivery systems in vivo. Methods for the use of SPLVs for the delivery of bioactive compounds in vivo and the treatment of pathologies, such as infections, are described.

4. BRIEF DESCRIPTION OF THE FIGURES

FIG. 1 graphically demonstrates the difference in membrane stability (as reflected by % leakage) between MLVs and SPLVs treated with varying concentrations of urea.

FIG. 2 The ratio of captured volume ($\mu l | \mu$mole) to moles of lipid used is shown for (a) MLVs and (b) SPLVs. For MLVs, this ratio varies little over the range of lipid used. For SPLVs, the ratio rises sharply for small amounts of lipid. In both case, the solute was sodium$^{51}$chromate; unentrapped material was removed by centrifugation.

Figure 3:
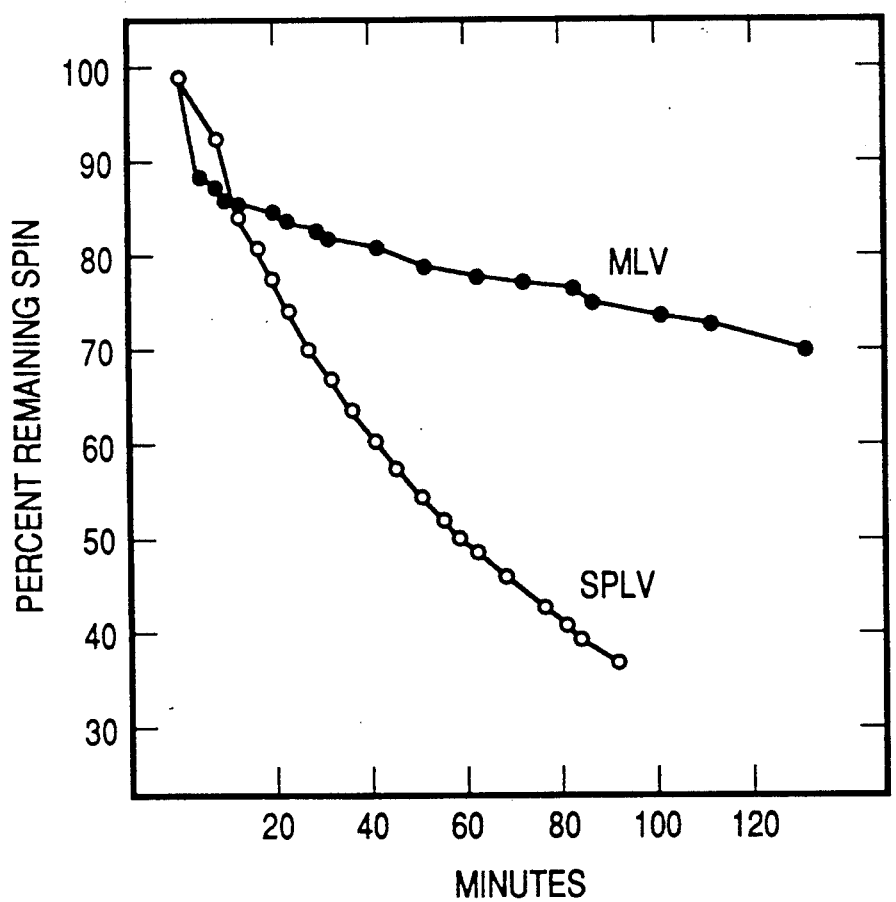

FIG. 3 graphically demonstrates the difference in the ability of ascorbate to reduce doxyl spin probes in SPLVs and in MLVs.

Figure 4:
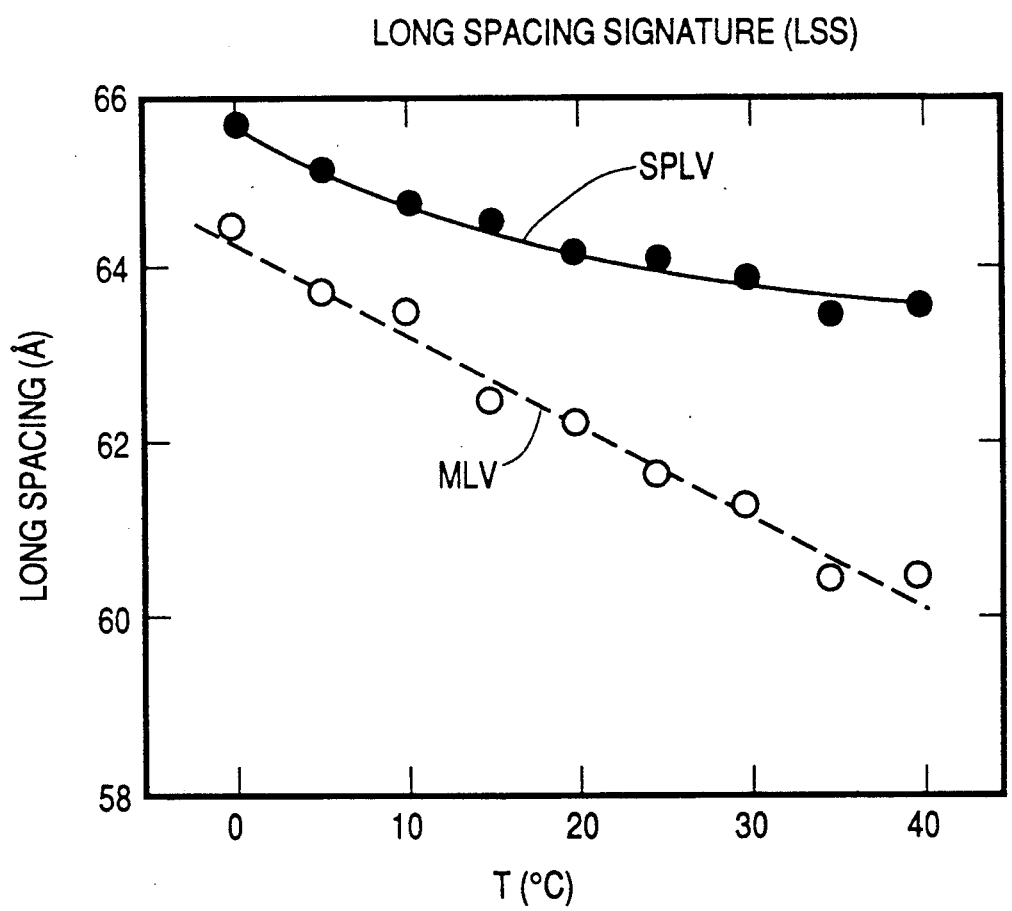

FIG. 4 represents the X-ray long spacing versus temperature for MLVs and SPLVs composed of egg phosphatidylcholine. The characteristic forms of the MLV and SPLV curves constitute the Long Spacing Signature, or LSS (see text). The LSS curve for SPLVs prepared by the emulsification process is the same as the LSS curve for SPLVs prepared by the monophasic solvent system process.

Figure 5:
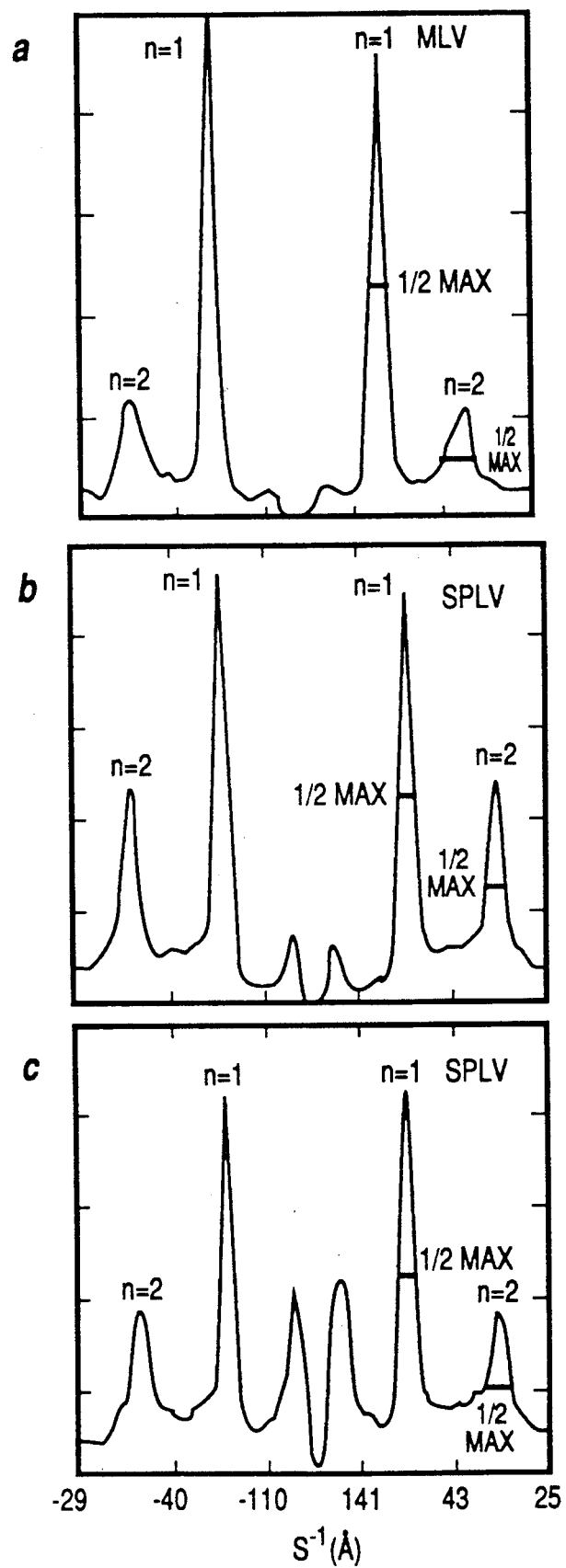

FIG. 5 represents the small-angle X-ray diffraction intensity (arbitrary units) versus inverse reciprocal distance for the following liposomes composed of egg phosphatidylcholine: (a) MLVs; (b) SPLVs prepared by the emulsification process; and (c) SPLVs prepared by the monophasic solvent system process. The first and second orders on either side of the beam stop shadow (dip near the center) are relatively sharp. However, the second order MLV diffraction (n=2) is wider than for SPLVs and often asymmetric. Horizontal bars indicate the full width at half maximum for the first and second order diffraction. This is the second X-ray signature (the Bragg Peak Signature) which distinguishes MLVs from SPLVs. T =40° C.

FIG. 6 The Wide-Angle X-ray diffraction Signature is shown for the following liposomes composed of egg phosphatidylcholine (a) SPLVs prepared by the emulsification process and MLVs; and (b) SPLVs prepared by the monophasic solvent system process. The signatures of MLVs and SPLVs differ as shown, however, this X-ray signature is more variable than the LSS. The low-angle camera geometry is unsuitable for diffraction for s$^{-1}$ less than 3.7 Å T=10° C.

Figure 7:
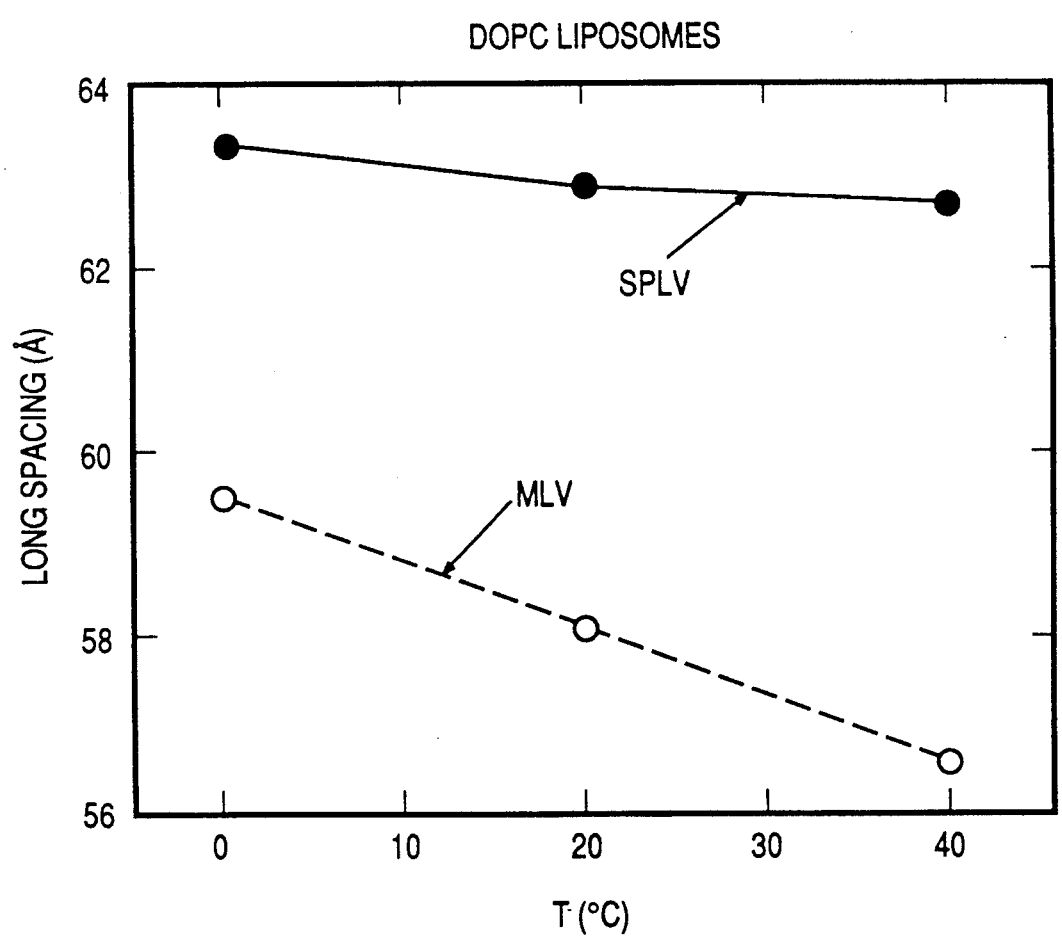

FIG. 7 The LSS for DOPC liposomes. In this and subsequent figures of the LSS, data points were acquired at 40° C., 20° C., and 0° C. (in that order). These data points are connected by straight lines to guide the eye. However, it is important to realize that the true shape of the SPLV curve is smooth, as seen in FIG. 4.

Figure 8:
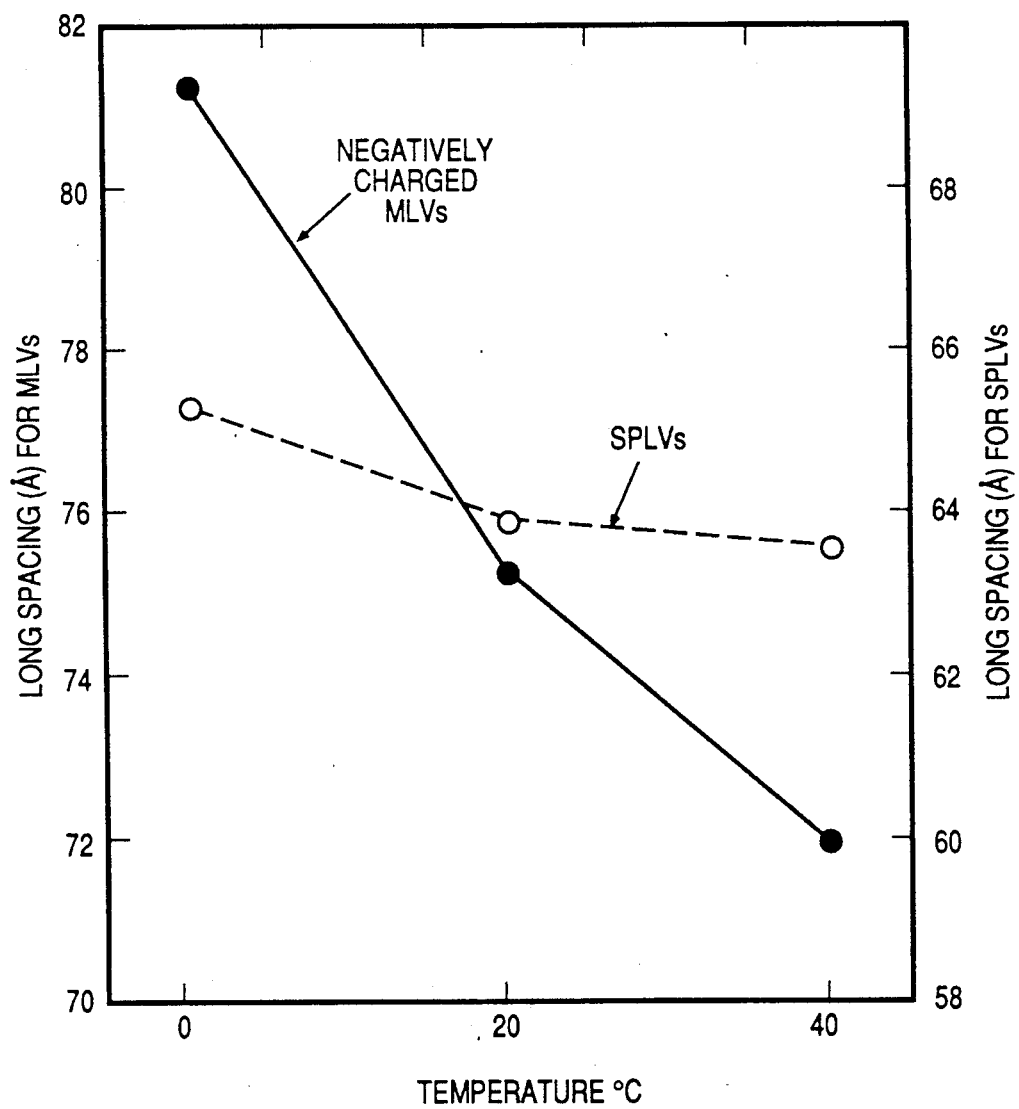

FIG. 8 The LSS for SPLVs composed of egg phosphatidylcholine and for negatively charged MLVs. Negatively charged MLVs were prepared using egg phosphatidylcholine and phosphatidic acid in a molar ratio of 8:2.

Figure 9:
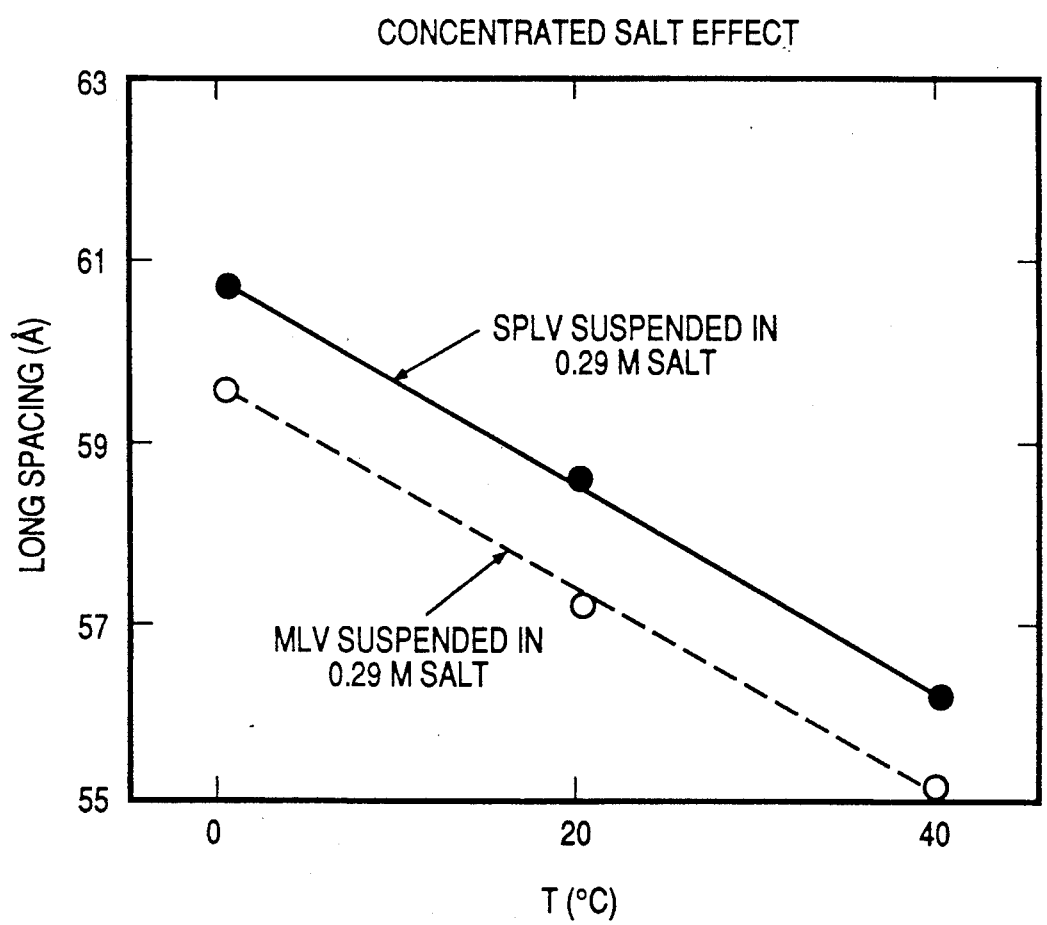

FIG. 9 The effect of preparing egg phosphatidylcholine liposomes in 0.145 M salt but suspending them in 0.29 M salt is to make the LSS curve of SPLVs look like the LSS curve of MLVs; however both curves differ as to the absolute values.

Figure 10:
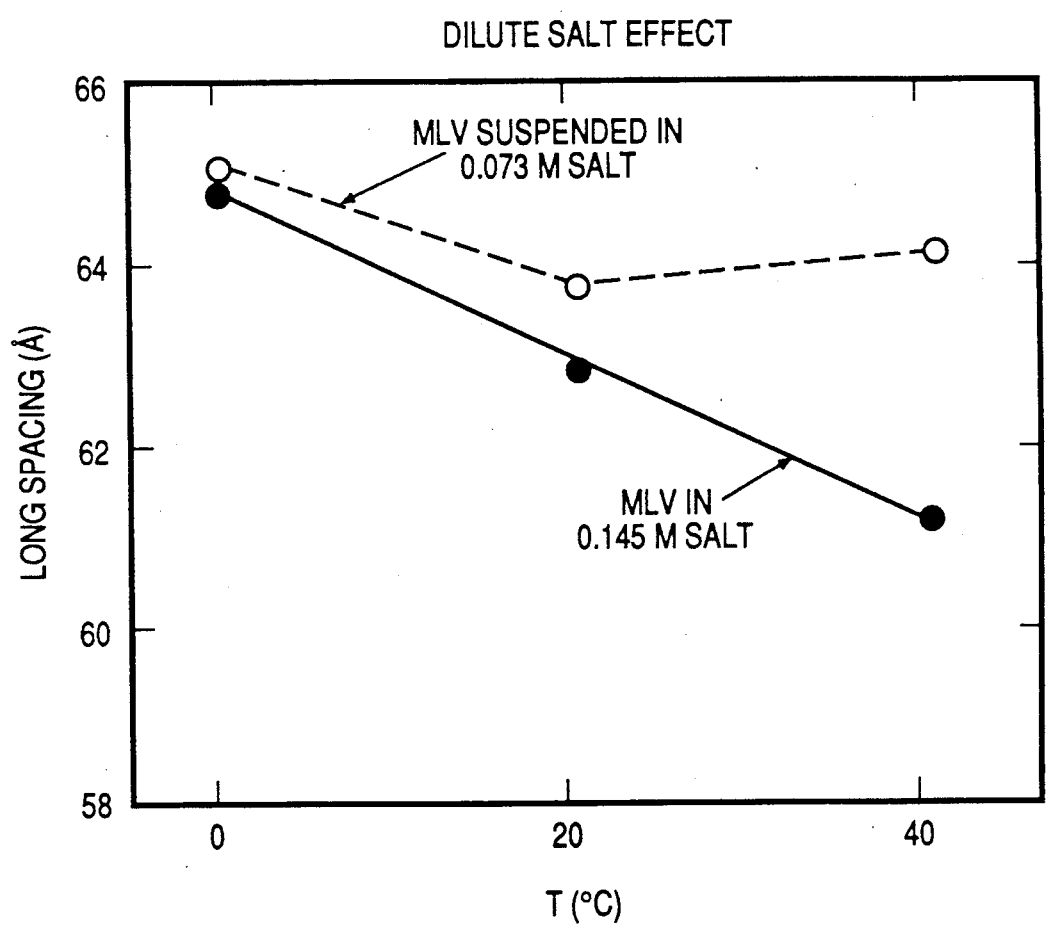

FIG. 10 The effect of preparing egg phosphatidylcholine MLVs in 0.145 M salt but suspending them in 0.073 M salt is to make the LSS look similar to the LSS of SPLVs.

Figure 11:
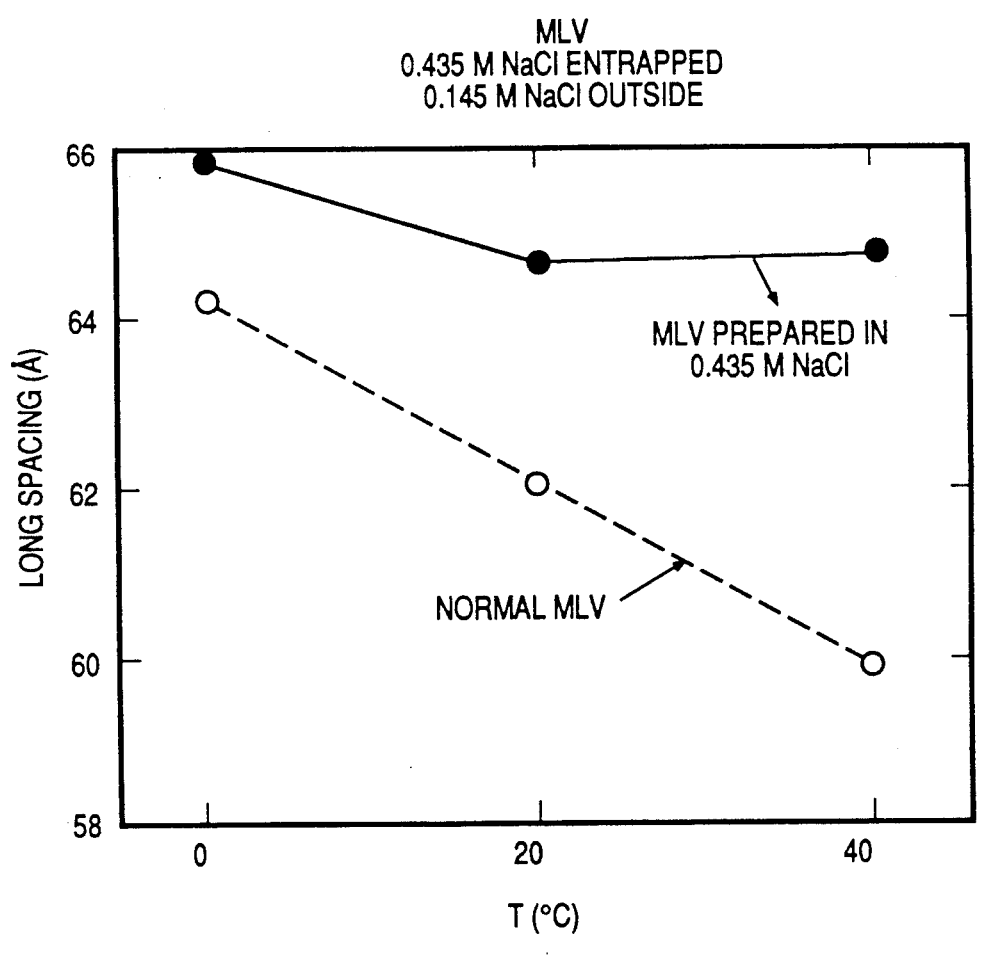

FIG. 11 Egg phosphatidylcholine MLVs which are prepared in 0.435 M salt, but suspended in 0.145 M salt yield an SPLV-like LSS. This is another way of enforcing a concentration gradient of the same sign as FIG. 12.

Figure 12:
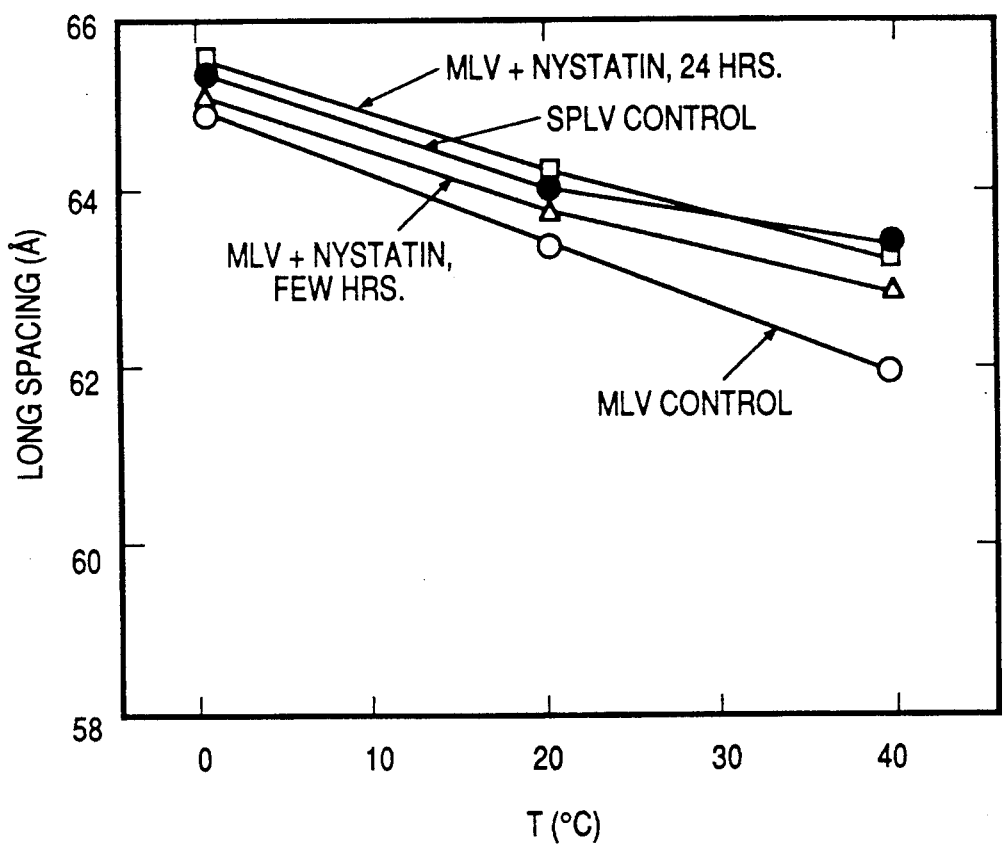

FIG. 12 Nystatin in the presence of cholestrol is known to be a non-specific ionophore. MLVs were prepared using egg phosphatidylcholine , 6.6 mole % cholesterol and 1 mole % nystatin. The MLV LSS is shown after a few hours and after 24 hours. Note that the MLV LSS relaxes to the LSS of the SPLV control. The MLV and SPLV controls contained cholesterol but no nystatin. The LSS of these controls did not change over the 24 hours period. As seen in the MLV control, cholesterol affects the LSS but at low concentrations, the effects are small.

Figure 13:
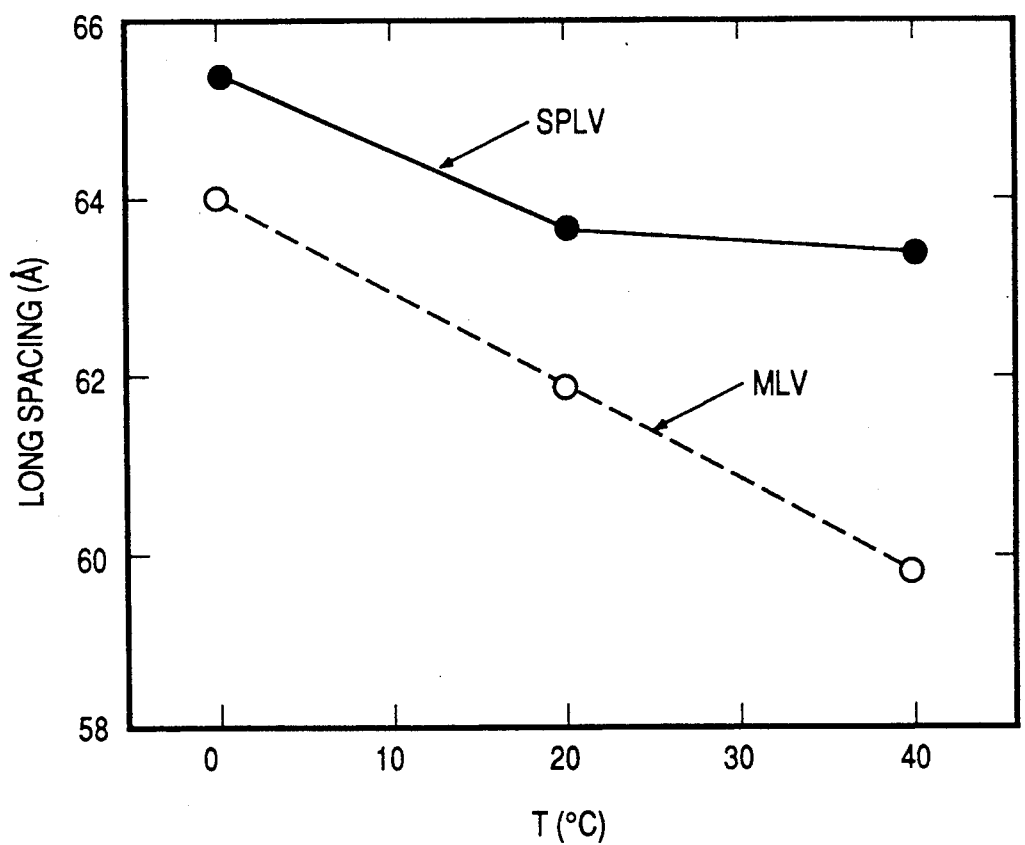

FIG. 13 SPLVs and MLVs which were prepared using egg phosphatidylcholine and suspended in a sucrose solution without any salt also yield the familiar distinct LSS for each type of liposome.

Figure 14:
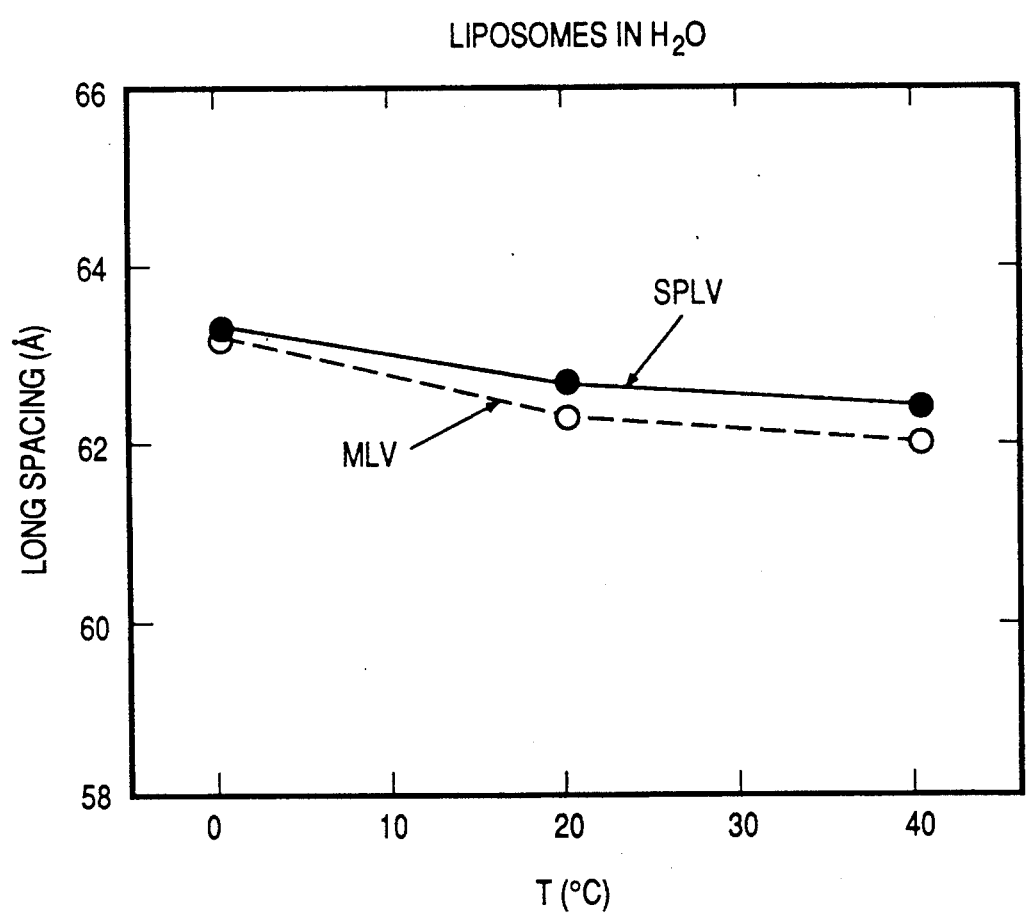

FIG. 14. The LSS for egg phosphatidylcholine liposomes prepared and suspended in distilled water. The two curves demonstrate an SPLV-like LSS.

Figure 15:
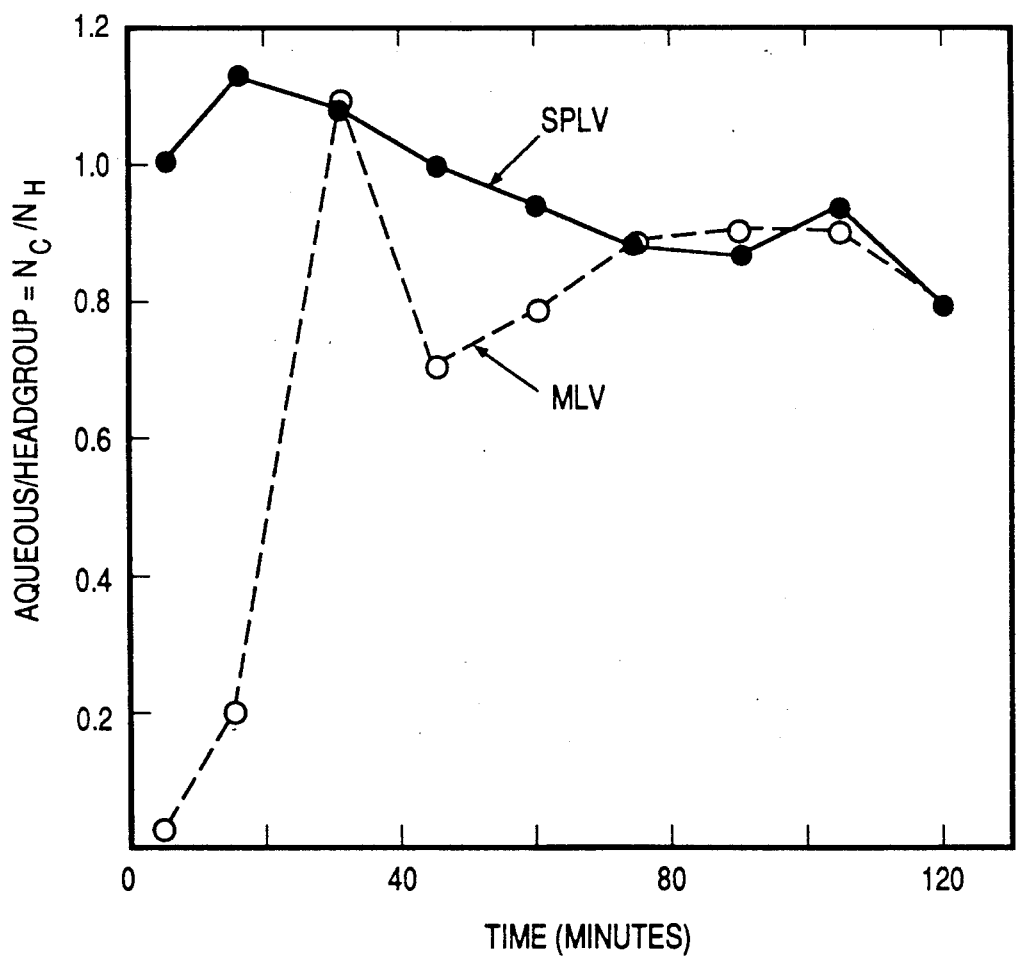

FIG. 15 The ratio of release of $^{14}$C aqueous marker counts (NC) to $^3$H membrane headgroup counts (N$_H$) is shown as a function of time as the liposomes are enzymatically digested. The steep rise of the MLV curve suggests that the outer aqueous compartments of the MLVs have a relatively low concentration of the aqueous marker solute molecules. At 120 minutes, each of the liposomes tested had released about 30% of the total headgroup counts. The MLV curve has been scaled by the factor $(N_C/N_H)_{SPLV\ TOT.} \times (N_H/N_C)_{MLV\ TOT.}$ to allow a direct comparison of the two curves.

Figure 16:
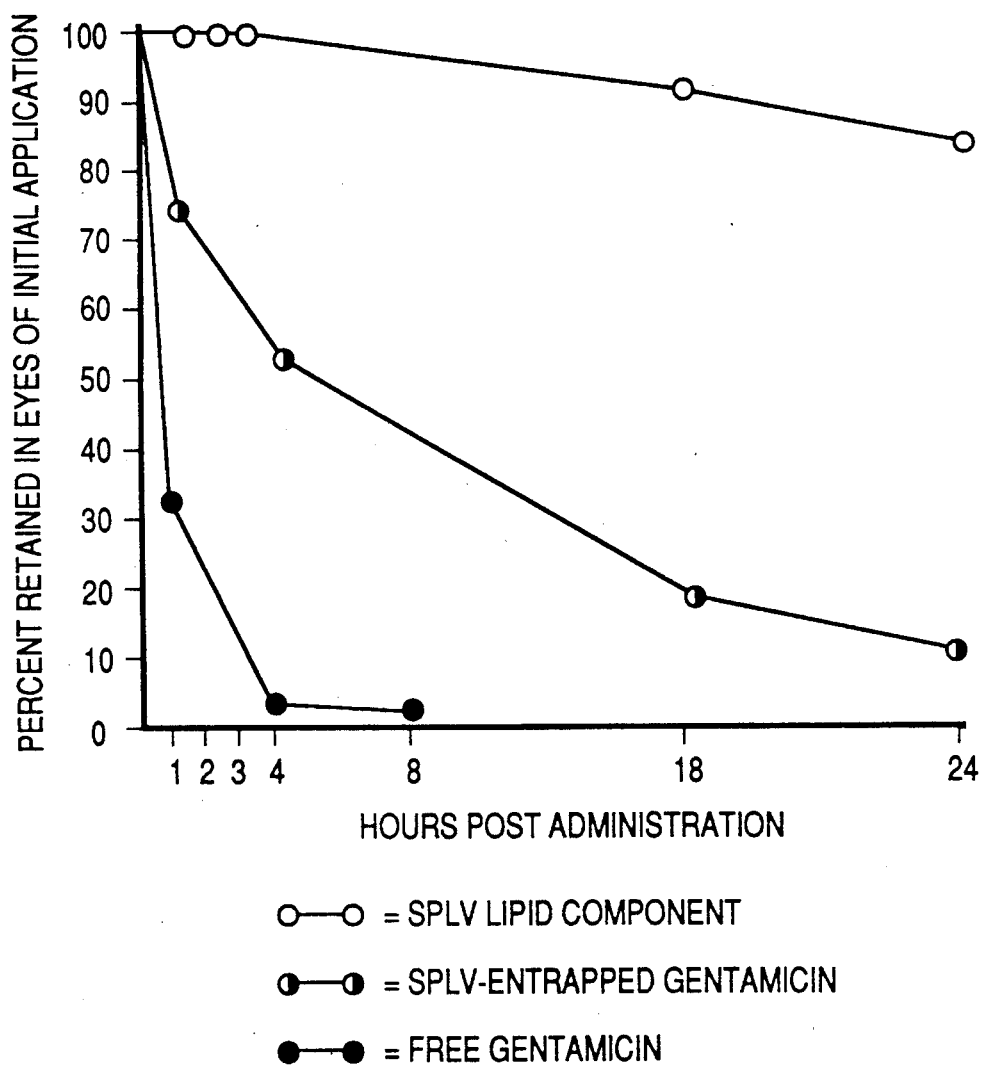

FIG. 16 graphically represents the retention of both the lipid and aqueous phases of SPLVs in the eyelid tissues of mice, and the sustained release of $^{125}$I-gentamicin from the SPLVs in vivo.

FIG. 17 represents the pharmacokinetics of gentamicin entrapped in MLVs or SPLVs administered intraperitoneally in mice. Antibiotic activity retrieved from the liver (a) and spleen (b) are plotted versus time in days.

Figure 18:
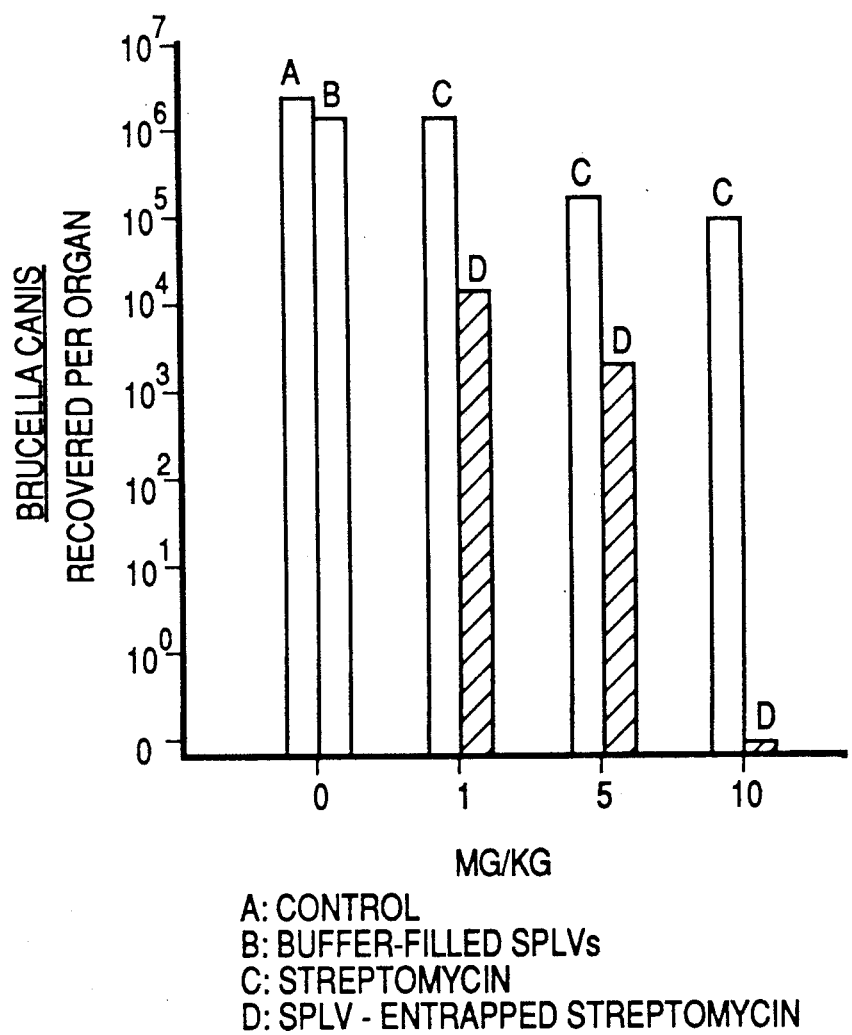

FIG. 18 graphically represents the effectiveness of a two stage treatment of *Brucella canis* infections in mice using SPLV-entrapped streptomycin based on *B. canis* recoverable from spleens of infected mice.

FIG. 19 graphically represents the effectiveness of a two stage treatment of *B. canis* infections in mice using SPLV-entrapped streptomycin based on *B. canis* recoverable from organs of infected mice.

FIG. 20 graphically represents the effectiveness of a two stage treatment of *Brucella abortus* in guinea pigs using SPLV-entrapped streptomycin.

5. DETAILED DESCRIPTION OF THE INVENTION

SPLVs are lipid vesicles, the lipid bilayers of which are characterized by a supramolecular organization which differs from that of conventional liposomes. Many of the lipid vesicles possess a high number of bilayers, occasionally in excess of one hundred. The membrane bilayer is composed of a bimolecular layer of an amphipathic lipid in which the non-polar hydrophobic hydrocarbon "tails" point inward towards the center of the bilayer and the polar, hydrophilic "heads"

point towards the aqueous phase. Occluded by the bilayers is an aqueous compartment, part of which makes up the lumen of the vesicle, and part of which lies between adjacent layers. Unlike other multilamellar lipid vesicles, the concentration of solutes entrapped in each of the aqueous compartments of SPLVs are substantially equal to the concentration of solute used to prepare the SPLVs and the bilayers are substantially noncompressed. Complexed with the lipid bilayers can be a variety of proteins, glycoproteins, glycolipids, mucopolysaccharides, and any other hydrophobic and/or amphipathic substance.

5.1. Preparation of SPLVs

SPLVs may be prepared by any process that results in a substantially equal concentration of entrapped solutes in each aqueous compartment of a plurilamellar lipid vesicle that is substantially equal to the concentration of solutes used to prepare the SPLVs. SPLVs can be advantageously prepared by the processes described below which result in a liposome product unique from any other liposome previously described.

5.1.1. Monophasic Solvent System Process

Monophasic solvent system process: a lipid or a mixture of lipids and an aqueous component are added to an organic solvent or a combination of organic solvents in amounts sufficient to form a monophase. The solvent or solvents are evaporated until a film forms. Evaporation may be accomplished by various methods, including but not limited to vacuum (e.g., by rotoevaporation or by passing an inert gas (e.g., nitrogen) over the monophase. Then an appropriate amount of aqueous component is added, and the film is resuspended and agitated in order to form the SPLVs.

The organic solvent or combination of solvents used in the process must be miscible with water and once mixed with water should solubilize the lipids used to make the SPLVs.

For example, an organic solvent or mixture of solvents which satisfies the following criteria may be used in the process: (1) 5 ml of the organic solvent forms a monophase with 0.2 ml of aqueous component and (2) the lipid or mixture of lipids is soluble in the monophase.

Solvents which may be used in this process of the present invention include but are not limited to ethanol, acetone, 2-propanol, methanol, tetrahydrofuran, glyme, dioxane, pyridine, diglyme, 1-methyl-2-pyrrolidone, butanol-2 butanol-1, isoamyl alcohol, isopropanol, 2-methoxyethanol, or a combination of chloroform:methanol (e.g., in a 1:1 ratio).

According to the present embodiment of the process of the invention the evaporation should be accomplished at suitable temperatures and pressures which maintain the monophase and facilitate the evaporation of the solvents. In fact, the temperatures and pressures chosen are not dependent upon the phase-transition temperature of the lipid used to form the SPLVs. The advantage of this latter point is that heat labile products which have desirable properties can be incorporated in SPLVs prepared from phospholipids such as distearoylphosphatidycholine, which can be formed into conventional liposomes only at temperatures above the phase-transition temperature of the phospholipids. This process usually allows more than 30–40% of the available water-soluble material to be entrapped during evaporation and 2–15% of the available water-soluble material to be entrapped during resuspension; and up to 70–80% of the available lipid-soluble material can be entrapped if the lipid:drug ratio is increased significantly. With MLVs the entrapment of the aqueous phase, which only occurs during the rehydration step since no aqueous phase is present during the drying step, usually does not exceed 10%.

The following is an illustrative example of the proportions that may be used in SPLV synthesis using the monophasic solvent system process: SPLVs may be formed by adding 127 micromoles of phospholipid to 5 ml of ethanol and then adding 0.2 m$\pm$of aqueous component containing the active substance to be encapsulated. The resultant solution which comprises the material to be entrapped and the entrapping lipid is sonicated (sonication is an optional step) while streaming an inert gas over the mixture, thus removing most of the solvent and forming a film. To the resulting film is added 5–10 ml of aqueous component. The resuspended film is agitated in order to produce SPLVs. In order to entrap one or more agents in SPLVs, the agent or agents may be added to the monophase prior to evaporation and formation of the film. Alternatively, the agent or agents may be added with the aqueous component used to resuspend the film and form the SPLVs. In fact, to obtain a high entrapment efficiency, the agent or agents may be added to both the monophase and to the aqueous component used to resuspend the film. Two or more agents can also be entrapped in one SPLV preparation by adding one agent to the monophase and the other to the aqueous component used to resuspend the film. See U.S. Application Ser. No. 633,481, filed July 25, 1984 and U.S. Application Ser. No. 518,912, filed Aug. 1, 1983 which are incorporated by reference herein.

5.1.2. Emulsification Process

Emulsification process: An amphipathic lipid or mixture of lipids is dissolved in an organic solvent. Many organic solvents are suitable, but diethyl ether, methylene chloride, fluorinated hydrocarbons and mixtures of fluorinated hydrocarbons and ether are preferred. To this solution are added an aqueous phase and the active ingredient to be entrapped. This biphasic mixture is converted to SPLVs by emulsifying the aqueous material within the solvent while evaporating the solvent, using any evaporative technique, e.g., evaporation by passing a stream of inert gas over the mixture, by heating, or by vacuum. The volume of solvent used must exceed the aqueous volume by a sufficient amount so that the aqueous material can be completely emulsified in the mixture. In practice, a minimum of roughly 3 volumes of solvent to 1 volume of aqueous phase may be used. In fact the ratio of solvent to aqueous phase can vary to up to 100 or more volumes of solvent to 1 volume aqueous phase. The amount of lipid must be sufficient so as to exceed that amount needed to coat the emulsion droplets (about 40 mg of lipid per ml of aqueous phase). The upper boundary is limited only by the practicality of cost-effectiveness, but SPLVs can be made with 15 gm of lipid per ml of aqueous phase.

According to this embodiment of the present invention, the entire process can be performed at a temperature range of 4°–60° C. regardless of the phase transition temperature of the lipid used. The advantage of this latter point is that heat labile products which have desirable properties, for example, easily denatured proteins, can be incorporated in SPLVs prepared from phospholipid such as distearoylphosphatidylcholine, but can be formed into conventional liposomes only at temperatures above their phase-transition-temperature. The process usually allows more than 20% of the available water soluble material to be encapsulated and more than 40% of the available lipid soluble material to be encapsulated. With MLVs the entrapment of aqueous phase usually does not exceed 10%.

The following is an example of the proportions that may be used in SPLV synthesis using the emulsification process: SPLVs may be formed by adding 50 micromoles of phospholipid to 5 ml of diethyl ether containing 5 micrograms of BHT (butylatedhydroxytoluene) and then adding 0.3 ml of aqueous phase containing the active substance to be encapsulated. The resultant solution which comprises the material to be entrapped and the entrapping lipid is sonicated while streaming an inert gas over the mixture thus removing most of the solvent. This embodiment produces particularly stable SPLVs partially because of the incorporation of BHT into the vesicles.

See also Lenk et al., 1982, Eur. J. Biochem. 121:475-482 which describes a process for making liposome-encapsulated antibodies by sonicating and evaporating a solution of cholesterol and phosphatidylcholine in a mixture of chloroform and ether with aqueous phase added, but does not set forth the relative proportions of lipid to aqueous phase.

5.1.3. SPLV CONSTITUENTS

Most amphipathic lipids may be constituents of SPLVs. Suitable hydrophilic groups include but are not limited to: phosphato, carboxylic, sulphato and amino groups. Suitable hydrophobic groups include but are not limited to: saturated and unsaturated aliphatic hydrocarbon groups and aliphatic hydrocarbon groups substituted by at least one aromatic and/or cycloaliphatic group. The preferred amphipathic compounds are phospholipids and closely related chemical structures. Examples of these include but are not limited to: lecithin, phosphatidylethanolamine, lysolecithin, lysophatidylethanolamine, phosphatidylserine, phosphatidylinositol, sphingomyelin, cardiolipin, phosphatidic acid and the cerebrosides, ether lipids and phytanols.

Specific examples of suitable lipids useful in the production of SPLVs are phospholipids which include the natural lecithins (e.g., egg lecithin or soybean lecithin) and synthetic lecithins, such as saturated synthetic lecithins (e.g., dimyristoylphosphatidylcholine, or dipalmitoylphosphatidylcholine or distearoylphosphatidylcholine) and unsaturated synthetic lecithins (e.g., dioloyl-phosphatidylcholine or dilinoloylphosphatidylcholine. The SPLV bilayers can contain a steroid component such as cholesterol, coprostanol, cholestanol, cholestane and the like. When using compounds with acidic hydrophilic groups (phosphato, sulfato, etc.) the obtained SPLVs will be anionic; with basic groups such as amino, cationic liposomes will be obtained; and with polyethylenoxy or glycol groups neutral liposomes will be obtained. The size of the SPLVs varies widely. The range extends from about 100 nm to about 10,000 nm (10 microns) and usually about 100 nm to about 1500 nm.

Virtually any bioactive compound can be entrapped within a SPLV (entrapped is defined as entrapment within the aqueous compartment or within the membrane bilayer). Such compounds include but are not limited to nucleic acids, polynucleotides, antibacterial compounds, antiviral compounds, antifungal compounds, anti-parasitic compounds, tumoricidal compounds, proteins, toxins, enzymes, hormones, neurotransmitters, glycoproteins, immunoglobulins, immunomodulators, dyes, radiolabels, radio-opaque compounds, fluorescent compounds, polysaccharides, cell receptor binding molecules, anti-inflammatories, antiglaucomic agents, mydriatic compounds, local anesthetics, etc.

Also suitable for entrapment are combinations of incompatible drugs. Concurrent therapy with certain antimicrobial agents can be complicated because some agents which are particularly effective when used together in vitro cannot be formulated in a single mixture at therapeutic concentration for use in vivo due to a number of constraints. For example, mixtures of gentamicin and nafcillin at therapeutic concentrations result in the formation of complexes that precipitate out of solution, and therefore, are not administered in vivo simultaneously. In fact, certain drug combinations are not recommended for use in vivo due to drug incompatibility (i.e., either inactivation of the drug or formation of a precipitate). For example, it has been recommended that the following antibiotics not be mixed with any other drug: gentamicin, kanamycin, lincomycin, cephalothin, and ampicillin (Davis and Abbitt, 1977, JAVMA 170(2): 204-207). Moreover, certain agents cannot be solubilized in the same medium due to chemical restraints (e.g., a lipid soluble compound and a water soluble compound). These limitations reduce the possible combinations of agents that may be used to obtain enhancement of biological activity in combined thereapy. For a review of the topic see Goodman and Gilman, 1980, *The Pharmacological Basis of Therapeutics* Sixth Edition, pp. 1080–1106 and Davis et al., 1980, *Microbiology*, pp. 574–583. However, as seen from Examples, infra, incompatible drugs (i.e., nafcillin and gentamicin) can be combined in SPLVs to yield concurrent therapeutic results.

5.2. Characterization of SPLVs

SPLVs possess many and occasionally over one hundred bilayers, and as such are clearly distinct in their properties from liposomes with a single or few lamellae (e.g., SUVs and LUVs or REVs). Freeze-fracture electron microscopy indicates that SPLV preparations are substantially free of SUVs, LUVs or REVs. They are, however, similar to MLVs by electron microscopic techniques although many of their physical properties and biological efficacies are different. Thus, the following detailed comparison is focused on distinguishing SPLVs from MLVs.

In the instant specification that follows, we have compared SPLVs with classical MLVs as to biological efficacy. At the same dose of antibiotic, SPLVs are far more effective than MLVs in treating an obligate intracellular bacterial infection (brucella), and a systemic infection (salmonella). Part of the explanation of these surprising findings may lie in the differences in the pharmacokinetics of drugs administered via the two types of liposomes: whereas MLV- delivered antibiotic is dramatically reduced in the spleen in about 4 days, the SPLV-delivered antibiotic is still present in high concentrations up to 5 weeks later. These remarkable results immediately prompted two lines of inquiry: 1) How do SPLVs and MLVs physically differ? and 2) How does the body recognize and react to the physical differences?

The idealized multilamellar liposome consists of a sequence of concentric lipid bilayer shells enclosing some central aqueous volume. For egg phosphatidylcholine (EPC) liposomes the bilayers are separated by aqueous layers of a well defined width (approximately 20 Å thick) which is a compromise between the repulsive and attractive forces between the bilayers (Rand, 1981 Ann. Rev. Biophys. Bioeng. 10:277-314. Because liposomes are often intended to be used in vivo as drug carriers, the aqueous fluid normally contains buffered physiological saline, as well as other dissolved solutes. The standard method for producing MLVs involves vacuum drying lipid dissolved in a solvent, such as chloroform, to a thin film onto the bottom of a round-bottom flask. MLVs are formed by adding the aqueous solution and shaking or vortexing until the dry film is removed from the wall of the flask.

The exact details whereby the dry lipid film converts to MLVs is not well understood. Lipid bilayers are semipermeable membranes: water passes freely through them but solutes, such as salts, are retained (Bangham et. al., 1967 Chem. Phys. Lipids 1:25). It has been generally assumed that the aqueous solute concentration is uniform throughout the MLV. In the instant specification we demonstrate that in contrast to this general assumption, standard methods of producing MLVs result in vesicles with aqueous compartments which are depleted in solutes, i.e., that the MLV formation effects a separation of water from its dissolved solutes. This leads to an osmotic stress resulting in a compressed liposome.

By contrast, the SPLV processes disclosed in the present invention produce multilamellar liposomes characterized by a concentration of entrapped solutes in each of the aqueous compartments which is substantially equal to the concentration of solute used to prepare the SPLVs, relatively little osmotic gradient on the liposomes and, therefore, an uncompressed liposome. As explained infra, the state of osmotic stress on the liposomes affects a broad spectrum of physical properties of the vesicles and has profound implications on the understanding and use of lipid bilayers.

The subsections which follow report on the physical differences between SPLVs and MLVs which were prepared using the same ingredients. The method of preparation of the SPLVs and MLVs used in these studies is described below:

MLV Preparation

EPC (100 mg in chloroform, Sigma Chemical Co., type VIIe) was rotary evaporated at room temperature to a thin dry film in a 50 ml round bottom flask. Occasionally, as described in the text, other lipids and/or solvents were used. Two ml of an aqueous phase (typically, HEPES buffer consisting of 72.5 mM KCl, 72.5 mM NaCl, 10 mM HEPES, pH 7.4) was added to the flask. If a particular solute was to be entrapped, it was also mixed into the aqueous phase added to the flask. The flask was vortexed until the lipid film coating the flask was completely suspended. The suspension was then set on the bench to equilibrate for 2 hours after which it was washed four times. Each wash was done by mixing the suspension with buffer to a total volume of 20 ml, followed by centrifugation (10,000 ×g) to pellet the liposomes. The supernatant was removed and the pellet was then resuspended for further washes or to a designated final volume.

SPLV preparation using the emulsification process

EPC in chloroform (100 mg), or, occasionally, other lipids as described in this text, were rotary evaporated to dryness in 50 ml of round bottom flask. The lipid film was dissolved in 5 ml of ethyl ether. Then, 0.3 ml of the aqueous phase (typically HEPES buffer) was added to the ether-lipid solution. If a particular solute was to be entrapped it was dissolved in the aqueous phase prior to adding it to the ether-lipid solution. The two-phase mixture (aqueous and ether) was emulsified in a bath sonicator (Laboratory Supplies Co., model G1125P1G) during which time a gentle stream of nitrogen was passed over the mixture. This was continued for approximately 2 minutes until the ether was largely evaporated and ether could no longer be smelled. The resulting cake was resuspended in 10 m± of buffer, by swirling the fluid in the flask. This liposome suspension was pelleted and washed, as described for MLVs.

SPLV preparation using the monophasic solvent system process

An EPC film was prepared in a 50 ml round bottom flask by rotary evaporation from chloroform, as for SPLVS. Five ml of 95% ethanol and 0.2 ml of HEPES buffer were added to the flask and the flask was vortexed until the lipid film was dissolved. The result was a monophase solution of lipid, ethanol, and the buffer. The monophase was then rotary evaporated to dryness. The film contained the solutes which were dissolved in the buffer. This dry film was suspended and washed as described above in the MLV procedure.

5.2.1. Stability of SPLVS in Storage

Stability of a lipid vesicle refers to the ability of the vesicle to sequester its occluded space from the external environment over a long period of time. For a lipid vesicle to be useful it is paramount that it be stable in storage and handling. It will be seen that SPLVs made from natural lecithin demonstrate increased stability during storage in buffer when compared to MLVs made from the same ingredients.

There are two factors that cause vesicles to leak. One is auto-oxidation of the lipids whereby the hydrocarbon chains form peroxides which destabilize the bilayers. This oxidation can be drastically slowed down by the addition of antioxidants such as butylated hydroxy toluene (BHT) to the vesicle preparation. Vesicles can also leak because agents in the exterior environment disrupt the bilayer organization of the lipids such that the lipids remain intact, but the membrane develops a pore.

Preparations of lipid vesicles are white in color when first made. Upon auto-oxidation, the preparation becomes discolored (brownish). A comparison of MLVs to SPLVs prepared using the same lipid and aqueous components reveals that MLVs discolor within one to two weeks whereas SPLVs remain white for at least two months. This is supported by thin layer chromatography of the constituent lipids which showed degradation of the lipids in the MLVs but not of the lipids of the SPLVs. When these vesicles are prepared by adding BHT as well as the other constituents, then MLVs appear slightly discolored within one month whereas the SPLVs remain white and appear stable for at least 6 months and longer.

SPLVs and MLVs are also distinguished by the way they leak molecules entrapped in the aqueous compartments. In general, SPLVs maintain their entrapment dramatically longer than MLVs. Evidence indicates that SPLVs are able to sequester an encapsulated agent from molecules as small as calcium ions for more than six months. Arsenazo III is a dye which changes color from red to blue with the slightest amount of divalent cation present. By encapsulating the dye in SPLVs and adding calcium chloride to the storage buffer it is possible to measure the stability of the vesicles by looking for a color change. This was demonstrated by mixing the calcium sensitive dye Arsenazo III (3 mM) in the buffer used to prepare the liposomes. The liposomes were then washed to remove any unentrapped Arsenazo III, suspended in HEPES buffer with 500 mM $CaCl_2$, purged with $N_2$, sealed in screw top vials and stored at room temperature. Leakage of the Arsenazo III can be readily detected by eye by the color change with occurs when the dye contacts $Ca^{++}$. Whereas MLVs leaked within a few days, the SPLVs have not leaked after 15 months at 4° C.

A number of antibiotics have also been tested and the results also demonstrated the stability of SPLV entrapment. When placed in a buffer containing isotonic saline at neutral pH, SPLVs containing antibiotic are stable for more than four months, as demonstrated in Table I. These data indicate that none of the antibiotic originally encapsulated within the SPLVs leaked out in the period of the experiment.

TABLE I

STABILITY OF EGG PHOSPHATIDYLCHOLINE SPLVS AFTER STORAGE IN SEALED CONTAINERS AT 4° C. FOR 4½ MONTHS[a]

| Entrapped Drug | Initial Entrapment % | Leakage Into Supernatant[b] | Bioavailability of Entrapped Drug (%) |
|---|---|---|---|
| Streptomycin Sulfate | 34.1 | 0 | 97 |
| Spectinomycin | 37.2 | 0 | 84 |
| Chloramphenicol | 35.2 | 0 | 89 |
| Oxytetracycline | 18.8 | 0 | 91 |

[a]SPLVs were prepared using 127 μM egg phosphatidylcholine (EPC) and 25 μM drug. At the end of 4½ months storage at 4° C. the SPLVs were separated from storage buffer by centrifugation. Serial dilutions of the SPLV contents and the supernatant were applied to bacterial lawns in order to determine bioactivity as compared to standard dilutions of antibiotic.
[b]0 indicates below detectable levels as determined by bioactivity.

In the following experiments vesicles were prepared which contained radioactive tracer molecules within the occluded aqueous compartments. When placed in a buffer containing isotonic saline at neutral pH, SPLVs containing antibiotic exhibit prolonged stability in storage. The vesicles were prepared, each containing one of the following radio-labeled drugs: $^{125}I$-p-hydroxypropionic acid-derived gentamicin sulfate, $^{14}C$-indomethacin, and $^3H$-inulin. After storage at various temperatures for 14 days the vesicles were separated from the medium by centrifugation, and the relative amount of radioactivity that escaped from the vesicles into the medium was determined. The results demonstrated that SPLVs were more stable during storage than were MLVs.

These experiments demonstrate that SPLVs are sufficiently stable to withstand storage and handling problems. Although it is possible to make MLVs which are stable for this long, they must be made from synthetic lipids such as DSPC and thus become prohibitively expensive and are not useful in many in vivo applications.

5.2.2. Stability of SPLVS in Other Environments

Placing lipid vesicles in a medium which contains membrane perturbing agents is a way to probe different molecular organizations. Depending on how the membrane is organized, different vesicles will respond differently to such agents.

In the following experiments vesicles were prepared which contained a radioactive tracer molecule ($^3H$-inulin) within the occluded aqueous compartment. Inulin, a polysaccharide, partitions into the aqueous phase, and thus when radiolabeled may be used to trace the aqueous contents of lipid vesicles. After an appropriate interval of exposure to a given agent, the vesicles were separated from the medium by centrifugation, and the relative amount of radioactivity that escaped from the vesicles into the medium was determined. These results are reported in Table II; values are expressed as percent leaked, meaning the proportion of radioactive material in the surrounding medium relative to the starting amount encapsulated in the vesicles.

SPLVs are more stable than MLVs in hydrochloric acid. Table II illustrates that both MLVs and SPLVs, when made from egg lecithin, are destabilized when exposed to 0.125 N hydrochloric acid for one hour. However, it is noteworthy that the SPLVs are considerably less susceptible to the acid than MLVs. Presumably this different response reflects an intrinsic difference in the way the lipids interact with their environment.

TABLE II

STABILITY OF SPLVS IN OTHER ENVIRONMENTS

| | % LEAKAGE | |
|---|---|---|
| Incubating Medium[a] | MLVs | SPLVs |
| Hydrochloric Acid | | |
| 0.125M | 90.5 | 55.2 |
| Urea | | |
| 1M | 21.7 | 44.8 |
| Guanidine | | |
| 0.5M | 5.7 | 7.4 |
| 1.0M | 8.3 | 10.1 |
| Ammonium Acetate | | |
| 0.5M | 27.0 | 67.0 |
| 1.0M | 25.9 | 54.7–63.1 |
| Serum | 76.2 | 57.8 |

[a]Incubation time is 2 to 4 hours except incubation in HCl was for 1 hour at room temperature.

SPLVs also respond differently than MLVs when exposed to urea (FIG. 1 and Table II). Urea is a molecule with both a chaotropic effect (disrupts the structure of water) and a strong dipole moment. It is observed that SPLVs are far more susceptible to urea than they are to an osmotic agent such as sodium chloride at the same concentration (FIG. 1). MLVs do not leak significantly more in urea than they would in sodium chloride. Although the explanations for this different behavior are theoretical, it would appear that the response is due to the dipole effect, rather than a chaotropic property, since guanidine, a molecule similar to urea, does not destabilize SPLVs (Table II). Although guanidine is also strongly chaotropic, it does not possess a strong dipole moment.

SPLVs are also susceptible to ammonium acetate, while MLVs are not (Table II). However, neither ammonium ion (in ammonium chloride) nor acetate (in sodium acetate) are particularly effective in causing SPLVs to destabilize. Thus it would appear that it is not the ion itself, but the polarity of the ammonium acetate which is responsible for inducing leakage.

Initially these results seem surprising because SPLVs are more stable than MLVs when incubated in body fluids such as sera or blood. However a theoretical explanation for these results can be proposed (of course other explanations are possible). If the stability of the SPLV is due to the unique structure of its uncompressed or unstressed membrane bilayers such that the polar groups of the membrane lipids are hydrated by a cloud of oriented water molecules, or hydration shell, then it is possible that any agent which disrupts or interferes with such hydration shells would promote changes in structural membrane integrity, and therefore, leakage.

Independent of the theoretical explanations for the destabilization of SPLVs in urea the results serve to demonstrate characteristic differences between the structure of MLVs and SPLVs. This difference serves a very useful purpose in application. As described infra, SPLVs become slowly leaky when applied to the eye. Presumably this desired slow release of contents is due to a similar destabilization of the SPLVs when exposed to tear fluid.

SPLVs are more stable in serum than MLVs. Many applications of lipid vesicles include administering them intraperitoneally, such as for the treatment of brucellosis. To be effective, the vesicles must survive for a sufficient time to reach their desired target. SPLVs and MLVs, both made from egg lecithin, were exposed to fetal bovine serum which contained active complement, (Table II). After 48 hours exposure at 37° C., SPLVs are demonstrably more stable than MLVs.

5.2 3. Entrapment of Active Material by SPLVs

One measure which distinguishes between liposomes is the efficiency with which an aqueous solute may be entrapped. Entrapment efficiency (or encapsulation efficiency) is defined as the fraction of the aqueous compartment sequestered by bilayers.

As a prime example of the superiority of SPLVs over traditional MLVs, SPLVs entrap a larger percentage of the available active material thereby conserving material (see Table III). Entrapment is measured herein as the fraction of initial solute remaining with the liposomes after four washes.

TABLE III

COMPARISON OF MLVS AND SPLVS

| Encapsulation of: | % Available Material Entrapped[a] | | |
|---|---|---|---|
| | MLVs | Emulsification Method | Monophasic Solvent System Method[b] |
| inulin (aqueous space marker) | 2–6 | 20–37 | 37 |
| bovine serum albumin | 15 | 20–50 | ND[c] |
| streptomycin | 12–15 | 20–40 | ND |
| polyvinylpyrrolidone (aqueous space) | 5 | 25–35 | ND |
| $^{125}$I-Gentamicin | ND | 33 | 38 |

TABLE III-continued

COMPARISON OF MLVS AND SPLVS

| Encapsulation of: | % Available Material Entrapped[a] | | |
|---|---|---|---|
| | MLVs | Emulsification Method | Monophasic Solvent System Method[b] |
| $^{14}$C-Indomethacin | ND | 22 | 15 |

[a]Values are expressed as percent entrapped meaning the proportion of radioactive material in the liposome pellet (cpm) relative to the starting amount (cpm) added to the preparation.
[b]Radiolabeled material to be entrapped was added to the monophase. After evaporation to a film and resuspension with aqueous buffer to form SPLVs, the preparation was pelleted and the radioactivity of the supernatant was determined.
[c]Not determined.

5.2.4. Effect of Varying the Initial Lipid to Aqueous Ratio

Another parameter used to characterize liposomes, called captured volume, is defined as the volume enclosed by a given amount of lipid and is expressed as units of liters entrapped per mole of total lipid (1 mol $^{-1}$). To gain insight as to the formation kinetics we examined the dependence of the processes for preparing MLVs and SPLVs on the initial amount of lipid used. The ratio of solute entrapped to the amount of lipid used in preparing the liposomes (i.e. captured volume) versus the starting amount lipid was determined by entrapping trace quantities of radioactively labeled water soluble markers. The amounts of lipid used to prepare the liposomes were varied from 15 to 658 μmoles. Sodium $^{51}$chromate ($^{51}$Cr) was entrapped in MLVs and SPLVs which were washed by centrifugation and then placed in a gamma counter to determine the amount of entrapped $^{51}$Cr.

As shown in FIG. 2, the ratio of solute entrapped to lipid used was essentially constant for MLVs. The simplest interpretation of this result is that the use of more lipid resulted in the formation of more MLVs without changing the entrapped $^{51}$Cr to lipid ratio of individual liposomes. By contrast, SPLVs entrapped more efficiently (FIG. 2) at high aqueous to lipid ratios, suggesting that the SPLV composition changed as the initial lipid concentration was increased.

5.2.5. Volume of SPLVs

Furthermore, when collected in a pellet by centrifugation from 1,000 to 100,000 ×g, SPLVs form a pellet that is substantially larger than MLVs, given the same phospholipid concentration. At a force of 16,000 ×g, the SPLVs form a pellet approximately one third larger than MLVs.

As shown in Table III (supra) if $^{14}$C-inulin is dissolved in the water used to prepare the liposomes, MLVs typically entrapped 2% of he inulin whereas SPLVs entrapped 37%. If one assumes that 2% ×2 ml =40 μl=of the inulin solution is entrapped in MLVs and that 37% of 0.3 ml =111 ul is entrapped in SPLVs then the latter should contain 111/40 =2.8 times as much fluid. In fact, upon centrifugation, SPLVs yielded pellets which were larger than MLVs, but only by about 30%. Consequently, the difference in entrapment efficiency cannot be simply due to the difference in the volume of the initially entrapped aqueous fluid. When the experiment was done with $^{22}$NaCl, the MLVs entrapped 2% and the SPLVs entrapped 27%.

MLV and SPLV pellets behaved quite differently. After centrifugation (10,000 ×g), and upon pouring off the supernatant, the MLV pellet remained intact in the bottom of the test tube. By contrast, the SPLV pellet was soft and tended to run out of the tube with the last of the supernatant. This difference was apparant even after the first preparative wash.

5.2.6. Buoyant Density of SPLVs

Additionally, SPLVs have a lower buoyant density than MLVs. This is measured by banding in a ficol gradient in which SPLVs layer above 0.5% ficol whereas MLVs layer above 1% ficol.

5.2.7. Osmotic Properties of SPLVs

Since phospholipid bilayers are permeable to water, placing liposomes in a hypertonic environment drives the occluded water out due to osmotic force. When placed in a hypertonic environment, SPLVs shrink more than MLVs. In addition, after shrinking 16 hours in a buffer that is twenty times higher than the internal salt concentration, SPLVs do not shrink to the same final volume as MLVs (SPLV pellets remain ⅓ larger than MLV pellets). This indicates that the difference in pellet size is not due to differences in aqueous enclosed volume.

In fact, the osmotic properties of MLVs greatly differ from those of SPLVs. The unequal concentrations of solute in the aqueous compartments of the MLV and the solute depletion in its outer layers creates an osmotic gradient that compresses the MLV. In contrast, the concentration of solute in each aqueous compartment of the SPLVs which is substantially equal to the concentration of solute used to prepare the SPLVs results in uncompressed lipid vesicles. This is discussed in more detail infra.

5.2.8. Electron Spin Resonance

Although SPLVs and MLVs appear similar by electron microscopy, ESR (electron spin resonance) spectroscopy reveals differences in their supramolecular structure. SPLVs can be distinguished from MLVs on the basis of their molecular architecture as evidence by greater penetrability to ascorbate. It is possible that these differences in molecular architecture contribute to their different biological effects.

In electron spin resonance spectroscopy a spin probe such as 5-doxyl stearate (5DS) is incorporated into the lipid bilayer. The unpaired electron of the doxyl group absorbs microwave energy when the sample is inserted into a magnetic field. Both SPLVs and MLVs were labeled with 5-doxyl stearate as follows: SPLVs and MLVs were made as previously described, except that 1 mole percent of 5-doxyl stearate (Molecular Probes, Junction City, Oregon) was added to 40 mg of EPC in chloroform prior to the initial rotary evaporation step. After the formation of liposomes, the preparations were washed again and ESR spectra of both samples were recorded.

An illustration of the differences between SPLVs and MLVs resides in the ability of ascorbate to reduce doxyl spin probes. It has been known for some time that ascorbate reduces doxyl moieties presumably to their hydroxylamine analogs which do not absorb microwave energy in a magnetic field In aqueous solutions the reduction occurs rapidly with concomitant loss of ESR signal. If the spin probe is in a protected environment such as a lipid bilayer it may be reduced more slowly or not at all by the hydrophilic ascorbate. Thus the rate of nitroxide reduction can be used to study the rate of penetration of the ascorbate into lipid bilayers. FIG. 3 shows the percentage remaining spin versus time for SPLVs and MLVs suspended in an ascorbate solution. Following the addition of ascorbate (10 mM final concentration), spectra were recorded at regular intervals in order to follow reduction of signal as a function of time. At 90 minutes the ascorbate has reduced 25% of the probe embedded in MLVs but 60% of the probe embedded in SPLVs. The simplest interpretation is that SPLVs allow for a dramatically greater penetrability of ascorbate than do MLVs.

5.2.9. X-Ray Diffraction

X-ray diffraction was applied in an attempt to define signatures which could be used to distinguish MLVs from SPLVs. Three different such X-ray diffraction signatures were found and are referred to herein as the Long Spacing Signature (LSS), the Bragg Peak Signature and the Wide Angle X-ray Signature.

5.2.9.1. X-Ray Diffraction Methods

X-rays were generated on a Rigaku RU-200 X-ray generator using a 0.2 x 2 mm focus cup and a loading of 50 KV, 60 mA. The beam was focussed horizontally via single-mirror Franks optics and collimated vertically as described in Gruner, 1977, The application of an efficient X-ray detector to diffraction from retinal rod outer segment membranes, Ph.D. Thesis, Princeton University, Princeton, N.J. X-rays were detected using a quantum-limited 2-dimensional slow-scan TV detector (Gruner, ibid.; Reynolds et al., 1978, Rev. Sci. Instr. 49:1241–1249), yielding the X-ray intensity in each of 240 x 240 adjacent areas or pixels. Typical X-ray exposure times were 5–30 seconds.

The small angle diffraction consisted of concentric rings of Bragg orders arising from the liposome multilayer repeat spacing. X-ray patterns were real-time reduced to 1-dimensional traces of intensity vs. scattering angle by radial integrations over 20-50° of the 2-dimensional pattern. Multilayer repeat spacings were determined by a least-square fit to the peak positions of the Bragg orders, where the peak positions were taken as the centers of parabolas least-squares fit to the peak profiles.

Wide-angle X-ray patterns were acquired via the TV-detector and reduced to 1-dimensional traces via radial integration. As opposed to the small-angle patterns the high-angle integrations at each radius were divided by the length of the arc integrated at that radius.

A typical X-ray run consisted of diffraction patterns taken at several temperatures with 2 minute equilibration times after temperature changes.

5.2.9.2. X-Ray Diffraction Signatures

In the small-angle regime, both SPLVs and MLVs exhibit three lamellar orders of diffraction which arise from the radial stacking of membranes in the liposome. If the X-ray repeat spacing (defined as the sum of the thicknesses of a lipid bilayer and of the inter-bilayer aqueous space) is graphed versus temperature, the curves for MLVs and SPLVs made using phosphatidylcholine (or any zwitterionic lipid) were seen to differ in characteristic ways (FIG. 4):

a) MLVs exhibited a repeat spacing which fell linearly with increasing temperature. By contrast, the SPLV curve flattened out at a higher temperatures.
b) The MLV curve fell below the SPLV curve.
c) The two curves approached one another at 0° C.

These three characteristics constitute the first of the diffraction signatures, hereinafter referred to as the Long Spacing Signature, or LSS. The LSS is the most reliable and easily quantified of the three X-ray signatures to be discussed for a given type of liposomal preparation the curves are repeatable to within 0.5 Å. Variation of the liposomal parameters (e.g., lipid or buffer composition) may cause the absolute values of the curves to shift but, in so far as the liposomes are phenomenologically distinguishable as SPLVs and MLVs, the LSS appears to distinguish between the two types of liposomes. Furthermore, the area detector that was used can generally acquire the needed small-angle X-ray exposures in 5–30 seconds. Moreover, the thermal kinetics of the LSS were at least as fast as our ability to slew over temperature (0.3° C./S) and acquire the data. Consequently, it was an experimentally convenient signature in that it could be acquired in a few minutes.

A second signature (herein referred to as the Bragg Peak Signature) which distinguished MLVs from SPLVs was the width and asymmetry of the Bragg peaks (FIG. 5a, b & c). When interpreting Bragg peaks of liposomes, one should compare the full width at half maximum of the peaks obtained for each order (this is indicated by horizontal bars in FIG. 5). The difference between the full width at half maximum of the first and second order peaks is greater for MLVs than for SPLVs. Furthermore, MLVs (FIG. 5a) exhibit peaks which are broader and often asymmetric. This may readily be interpreted as arising from a larger statistical variation of repeat spacings in the MLVs. The angle of diffraction, $2\theta$, for a given order, n, follows from the Bragg relation $$n\lambda = 2D \sin \theta, \quad \text{(Eq. 1)}$$
where $\lambda$ = X-ray wavelength
and $D$ = repeat spacing of the lattice.

Suppose the sample contains a distribution of repeat spacings characterized by a width, D. Then, for $\sin\theta \simeq \theta$, the spread in scattering angle is simply $$|\Delta\theta| \simeq \left| \frac{d\theta}{d\theta} \Delta D \right| \simeq n\lambda \frac{\Delta D}{\Delta D^2} \quad \text{(Eq. 2)}$$

Note that $|\Delta\theta|$ increases with the order number, n. This is why the peak asymmetry in FIG. 5a is only apparent in the second order peak (n=2); the asymmetry of the first order peak is hidden by the instrumental line width due to the X-ray camera. The use of this X-ray signature requires careful measurement of the instrumental line width which, in practice, is harder to measure than the repeat spacing. This signature also is more variable than the LSS. For these reasons, the LSS is the preferred signature to aid in identification purposes.

The third X-ray signature was in the wide-angle regime ($2/2\theta < 10$ Å) and is referred to herein as the Wide-angle X-ray Signature. Melted-chain lipids exhibit a broad peak at about 4.4 to 4.6 Å due to correlations in the hydrocarbon region (Luzzati, 1968, X-ray diffraction studes of lipid water systems; in Biological Membranes, Vol. 1., D. Chapman, ed., Academic Press, N.Y.; Costello & Gulik-Krywicki, 1976 Biochim. Biophys. Acta 445:412–434). As shown in FIG. 6 the MLVs yielded a well-defined peak at 4.4–4.6 Å but SPLVs exhibit diffraction which extends to much higher angles. This indicates that SPLVs have electron-density correlations which vary over a wider range of distances; in particular, over distances smaller than 4 Å. This signature requires a rearrangement of the X-ray detector geometry, tended to vary, and is harder to quantify than the LSS.

Of the three signatures, the width and asymmetry of the small-angle diffracted orders (i.e., the Bragg Peak Signature shown in FIG. 5) is most easily understood. For liposomes consisting of many layers, the shape of the diffracted orders is a direct reflection of the width and asymmetry of the distribution of membrane repeat spacings. (N.B., Unlike SPLVs, unilamellar and oligolamellar vesicles will not demonstrate a Bragg Peak Signature because there is no respective lattice which can be detected by X-ray diffraction.) MLVs exhibit relatively wide, asymmetric peaks indicative of a repeat spacing whose distribution mode and mean differ. This is consistent with the data of FIG. 5a since a nonuniform distribution of solutes would lead to non-uniform osmotic forces between the layers and result in a slight variation in the repeat spacings.

The LSS (FIG. 4) is relatively insensitive to the repeat spacing distribution; rather, by definition, it maps out the variation in the mean repeat spacing as the temperature is varied. Since the repeat spacing is the sum of the thicknesses of the bilayer and of the inter-bilayer aqueous space, both these component widths may be expected to be thermally sensitive. As the temperature is raised, more gauche rotamers are excited in the bilayer hydrocarbon, resulting in a thinner membrane and an increase in the area per molecule (Reiss-Husson, 1967, J. Mol. Biol. 25:363). In the presence of excess water, the thickness of the fluid space is set by a complicated balance of Van der Waals, hydration, membrane tension, and osmotic forces. In particular, the strong hydration force is likely to be coupled to the area/molecule, since it is known that the area/molecule changes as membranes are rehydrated (Small, 1967, J. Lipid Res. 8: 551–557). In addition, although there has been little investigation of the thermal variation in the hydration force at a fixed area/lipid molecule, it would be surprising if the force coefficients were thermally insensitive. Thus, there is a complicated interaction between the thicknesses of the water and lipid layers such that forces which act laterally in the lipid plane also affect both the lipid and water thicknesses. Our understanding of the statistical mechanics of the hydrocarbon, of the interactions in the lipid polar region, and of the hydration force is not yet sufficiently sophisticated to completely predict the LSS. (N.B., because the LSS maps the mean repeat spacing against temperature, the LSS is directly related to the Bragg peak signature. If there are no peaks in the Bragg signature, no LSS can be obtained. Therefore, unlike SPLVs, unilamellar and oligolamellar vesicles will not demonstrate an LSS.)

The Wide-angle X-ray Signature (FIG. 6) is also poorly understood. Broad, diffuse diffraction in the 4.6 to 3.5 Å range arises primarily from density correlations in the lipid hydrocarbon, although we cannot exclude the possibility that the wide-angle SPLV signal arises, in part, from water associated with the bilayers. The wide-angle signature may be expected to be less sensitive to changes in the aqueous region than the LSS.

5.2.9.3. Long Spacing Signature

The text below describes the use of the LSS to examine the liposomes which resulted when the normal procedures for preparing MLVs and SPLVs were altered.

It was first hypothesized that the differences between the signatures of MLVS and SPLVs may have resulted from contamination by the solvents used in the liposome preparations. When the liposomes were made, both chloroform and ethyl ether were used. These solvents, like many anesthetics, alter membrane properties (Janoff & Miller, 1982, a critical assessment of the lipid theories of general anesthetic action, in Biological membranes, Vol. IV., D. Chapman, ed., Academic Press, London). To address whether residual ether contamination was important, SPLV ether was measured via gas chromatography using a Beckman GC72-E gas chromagraph equipped with a flame ionization detector and a Spectra Physics "minigrator" electronic integrator. The column was a Waters Associates copper 6:×¼" poropak P. The carrier flow was 60 cc/min. The detection limit was 50 $\mu$M.

After 1 wash, 13 mole % ether remained; after the 2nd wash, 0.5 mole % was left; after the 3rd wash, the remaining ether was below the detectable limit of 0.1 mole %. Even so, ether was added to the chloroform-lipid stock solution used to prepare MLVs to see if this affected the MLVs. The resulting liposomes were indistinguishable from MLVs made without ether as indicated by the LSS (data not shown). Consequently, it was concluded that ether cannot account for the differences between the signatures obtained for MLVs and SPLVs.

Even though both MLVs and SPLVs were prepared from a lipid film dried from chloroform, it is possible that SPLVs would not contain the same concentration of residual chloroform because residual chloroform may have evaporated with the ether. To test if residual chloroform was involved, the lipid films used to produce MLVs and SPLVs were vacuum pumped for 72 hours and then washed 8 times in double the normal volume of wash buffer. The resulting LSS for each was indistinguishable from that of normal MLVs and SPLVs. We conclude that chloroform cannot be responsible for the differences between the signatures obtained for the liposomes.

Another hypothesis was that the SPLV process produced bilayers which differed in acyl chain composition in the inner and outer leaflets. This was conceivable because EPC is a mixture of lipids and contains a spectrum of acyl chains. To test this hypothesis, the liposomes were made out of pure DOPC (dioleoylphosphatidylcholine, Avanti Polar Lipids, Birmingham, Ala.), which contained only oleoyl chains. The LSS (FIG. 9) demonstrated DOPC MLVs and SPLVs to be distinct, thereby ruling out membrane asymmetry.

To determine whether the LSS of MLVs can be made to look like that of SPLVs simply by putting a charge on the membrane, MLVs composed of egg phosphatidylcholine and phosphatidic acid in a molar ratio of 8:2 were made and examined by X-ray diffraction. The results shown in FIG. 8 show that negatively charged MLVs do not have the same LSS as SPLVs.

5.2.9.4. Relation of Long Spacing Signature to the Osmotic Properties of SPLVS and MLVS Besides lipids and water, the remaining major constituents of liposomes were the salts dissolved in the buffers used to prepared the vesicles.

When an osmotic stress is imposed upon a multi-layered liposome many aspects of the structure of the vesicle are affected. As previously discussed the three X-ray signatures each probe different, although related, parts of the liposome structure. In principle, it is possible to stress bilayers in different ways so as to affect some parts of the structure more than others. The result is that a change in one of the X-ray signatures need not necessarily be reflected by simple changes in the others.

Experiments demonstrated that the salt concentration gradient across the liposomes, as opposed to the amount of the entrapped salt, is important in affecting the LSS. For example, FIG. 9 shows that if SPLVs were prepared in 0.145 M salt (i.e., physiological concentration), but suspended in 0.290 M salt, the resulting LSS resembles that of MLVs. Thus it appeared that a MLV-like LSS resulted if an osmotic gradient was imposed on SPLVs by increasing the salt concentration outside the liposomes (i.e., by exposing the SPLVs to a hypertonic environment). The LSS typical of SPLVs could similarly be achieved by suspending MLVs in a solution of low salt concentration (i.e., by exposing the MLVs to a hypotonic environment). FIG. 10 demonstrates, indeed, that MLVs prepared in 0.145 M salt but suspended in 0.073 M salt exhibit a SPLV-like LSS. The fact that the salt gradient is important is also seen in FIG. 11, which shows the LSS of MLVs prepared with 0.435 M salt and then suspended in 0.145 M salt; the LSS is again seen to be typical of that of that of SPLVs.

FIGS. 9–11 established that a salt concentration gradient (salt depleted inside the liposome) was sufficient to cause SPLVs to reveal a MLV-like LSS and that relaxing or reversing this gradient yielded a SPLV-like LSS. A further test of this hypothesis was to prepare liposomes with a non-specific ionophore, such as nystatin (Andreoli & Monahan, 1968, J. Gen. Physiol. 52:300–325; Holz & Finkelstein, 1970, J. Gen. Physiol. 56: 125–145), incorporated into the bilayers. In the presence of cholesterol, this ionophore allows passage of salt ions and would gradually relax a salt gradient. As would be predicted, the LSS of MLVs containing nystatin gradually converted to the LSS of SPLVs (prepared without nystatin) as the salts leaked through the nystatin pores (FIG. 12).

To investigate whether the differences between the liposomes were due to an osmotic gradient or an ionic gradient associated with a salt gradient, liposomes were prepared in 0.290 M sucrose, which is a non-ionic solute and a first approximation to the osmolarity of the 0.145 M salts that are normally used. FIG. 13 shows that the LSS differences between MLVs and SPLVs are preserved, suggesting that an osmotic gradient is sufficient.

The fact that an osmotic gradient is important in affecting the LSS may be seen in FIG. 14 which shows the LSS of liposomes prepared and suspended in distilled water. Note that under these conditions, the LSS of both MLVs and SPLVs yielded SPLV-like curves.

It should be noted that a SPLV-like LSS resulted if SPLVs were either prepared with no osmotic stress (FIG. 14) or with solutions which were somewhat more concentrated than the buffer outside the liposome. The latter statement follows from the fact that the 0.145 M salt used to prepare SPLVs lost about 10% of its water when the ether was evaporated during the SPLV formation process, thereby concentrating solutes.

The LSS is subject to variation which depends upon the osmotic conditions of the buffer used in suspending the liposomes. The ability to adjust conditions such that the LSS of a liposome can be manipulated to be MLV-like or SPLV-like does not mean that SPLVs and MLVs are the same. As previously mentioned, the LSS measures only one parameter of SPLVs. For instance, an MLV placed in a hypotonic solution will swell resulting in a change in its LSS, however the other X-ray signatures may not be affected. Furthermore, a change in the LSS of the MLV due to swelling of the MLV in a hypotonic solution does not indicate a change in the entrapment or distribution of solute molecules in the MLV. As is explained in detail below, in contrast to SPLVs, the MLV remains solute-depleted regardless of the change in its LSS when placed in a hypotonic solution.

5.2.9.5. Solute Distribution in SPLVS vs. MLVS

The hypothesis that MLVs are solute depleted was also tested directly via NMR. It is known that the $^{31}$P-NMR signal that is associated with phosopholipid is quenched by $Mn^{++}$. *If MLVs and SPLVs are prepared and suspended with a buffer containing $Mn^{++}$, one expects the integrated $^{31}$P-NMR signal to be less (per unit of lipid) for SPLVs then for MLVs.* The reason for this is that the SPLVs should have $Mn^{++}$ entrapped between the bilayers and, thus, accessible to all the $^{31}$P; consequently, the $^{31}$P-NMR signal should be strongly quenched. By contrast, if MLVs are solute and $Mn^{++}$ depleted, less of the lipid signal should be quenched.

SPLVs and MLVs were prepared and suspended in HEPES buffer containing 2 mM $MnCl_2$. $^{31}$P-NMR spectra were collected at 20° C. employing a Bruker WP 200 Fourier transform NMR spectrometer operating at 81 MHz for $^{31}$P. Accumulated free induction decays (FID's) from 5,000 transients were obtained using a 20 KHz sweepwidth, a 7μsec 90° radio frequency pulse and a 1 sec interpulse time in the presence of gated broad band proton decoupling. An exponential multiplication corresponding to 50 Hz line broadening was applied to the FID prior to Fourier transformation.

MLV and SPLV signals were accumulated under identical samples were run immediately after each other so that the relative signal intensities were accurate. The integrated $^{31}$P-NMR spectra were normalized by the SPLV and MLV concentrations (84.2 mg/ml and 109.9 mg/ml, resp.) so as to be directly comparable. The integrated SPLV signal intensity was found to be 72% that of MLVs; thus, as expected, the SPLV signal was strongly quenched.

The data thus far presented suggests that SPLVs have a concentration of solute in each of the aqueous compartments of the liposomes that is substantially equal to the concentration of solute used to prepare the SPLVs but that MLVs are solute depleted. It is likely during the hydration of the dry lipid film used to make MLVs water gains access to the space between the bilayers but most of the solutes were excluded. If it were possible to deposit a dry lipid film with solutes already between the layers, then the resultant liposomes might be expected to behave like SPLVs even though the dry lipid film is hydrated by the MLV process. This, in fact, is the monophasic solvent system process described in section 5.1.1. A solute-containing lipid film can be prepared by solubilizing lipid in a solvent (e.g., ethanol) which is also miscible with water, drying the mixture under vacuum, and then rehydrating the resulting film in buffer. Note that this final hydration step is identical to that used to prepare MLVs; only the lipid film with which one starts is different. The LSS of SPLVs prepared by the monophasic solvent system process is similar to that of SPLVs prepared by the emulsification process, as were the other two X-ray signatures (see FIGS. 4-6). This, again, suggested that MLVs are solute depleted.

Information about the distribution of solute within liposomes (i.e., the solute concentration profile) can be obtained via enzymatic digestion of the lipid. To this end liposomes were prepared with a radioactive marker incorporated in the lipid headgroups and a different isotopic marker incorporated in the aqueous solution. The liposomes were slowly degraded by exposure to phospholilpase C, an enzyme which cleaves the lipid headgroup from the glycerol backbone. The amount of headgroup marker released by the enzyme is a measure of the number of lipid molecules digested, which should also be proportional to the area of the lipid bilayer involved. As a layer of the liposome breaks down, the aqueous marker entrapped beneath that layer should also be released. Consequently, the ratio of the amount of headgroup to aqueous markers released measures the ratio of bilayer area to aqueous marker entrapped beneath that layer. The sharp X-ray diffraction peaks indicate that, even for MLVs, the aqueous space between the bilayers is constant to within a small fraction of an Angstrom. Because all the aqueous layers are essentially of fixed width, the amount of aqueous marker released per unit area of membrane is proportional to the aqueous marker solute concentration in that layer. Mathematically, if $dN_H/dt$ and $dN_A/dt$ are the rates of release of the headgroup and aqueous markers, respectively, then $$(dN_A/dt)/(dN_H/dt) = dN_A/dN_H = \alpha c \qquad \text{(Eq. 3)}$$

where $c$ = concentration of aqueous marker
and $\alpha$ = a proportionality constant.

If the aqueous marker concentration varies with depth in the liposome, then the ratio of marker release (the left hand side of Eq. 3) will vary over time as the enzyme degrades deeper and deeper layers of the liposomes. If, for example, the aqueous marker concentration between the outer bilayers is of lower concentration than that between the deeper bilayers then one expects the ratio $N_A/N_H$ to initially rise and then level out as the liposomes degrade.

This experiment was performed by incorporating a small amount of $^3$H-DPPC ($^3$H-dipalmitoylphosphatidylcholine) as a headgroup marker and entrapping $^{14}$C-sucrose as an aqueous marker dividing the liposome suspensions into 9 aliquots and adding Phospholipase C. Periodically over the course of the enzyme digestion, aliquots were centrifuged to settle the liposomes and the supernatant was scintillation counted to determine the amount of released headgroup and aqueous marker counts. The method is described in detail below:

MLVs and SPLVs were made containing a $^3$H-label in the membranes and a $^{14}$C-label in the aqueous spaces by mixing trace quantities $^3$H-DPPC with the EPC and by preparing the liposomes in buffer containing traces of $^{14}$C-sucrose. The $^3$H-DPPC had the label on the choline head groups. These double labeled liposomes were washed 4 times and divided into nine 0.5 ml aliquots so that each aliquot contained 5.0 mg of lipid. Phospholipase C (0.2 units) was added to each fraction and timing was initiated. Immediately, and every 15 minutes thereafter for 2 hours, one fraction from each group was removed, centrifuged at 10,000 $\times$ g and 50 $\mu$l of the aqueous supernatant recovered and the counts/minute of each label was determined by liquid scintillation counting. Phospholipase C digests phosphatidylcholine by cleaving the phosphorylcholine head groups which contain the $^3$H-label Thus, the two reaction products are $^3$H-phosphorylcholine and mixed diglycerides. Since neither of these compounds are capable of maintaining membrane integrity the $^{14}$C-sucrose entrapped within the aqueous space circumscribed by a bilayer will be released as the bilayer is digested. Upon centrifugation, three distinct layers are seen: a layer of diglycerides floating on the surface, a clear aqueous supernatant, and a pellet composed of undigested liposomes. Since both $^{14}$C-sucrose and $^3$H-phosphorylcholine are water soluble, counting the supernatant layer will indicate the amount of membrane digested, as well as the amount of solute ($^{14}$C-sucrose) which indicates the amount of membrane digested/amount of solute released.

The results are shown in FIG. 15. Note that the relative initial aqueous marker concentration of the MLVs is very low and then rises slowly while the aqueous marker concentration of the SPLVs is much more nearly constant. The simplest interpretation of FIG. 15 is that MLVs are especially solute depleted in the outer layers while SPLVs are of essentially uniform concentration throughout. Note that this interpretation is dependent on assumptions of sequential degradation of the liposome layers and is also complicated by heterogeneity (size, number of layers, etc.) in the liposomes. We note in passing that both MLVs and SPLVs were digested at roughly comparable rates.

5.2.9.6. IDENTIFICATION OF SPLVS

In view of the foregoing results, the following criteria may be used to identify an SPLV:
1) the lipid vesicle should be multilamellar and therefore have a demonstrable LSS and peaks in its Bragg Signature;
2) the lipid vesicle should have a high entrapment efficiency;
3) the lipid vesicle should be characterized by a concentration of solute in each aqueous compartment that is substantially equal to the concentration of solute used to prepare the SPLVs;
4) the lipid vesicle should be characterized by substantially non-compressed bilayers;
5) the LSS of a vesicle composed of zwitterionic lipids should be substantially as depicted for SPLVs in FIG. 4, provided the vesicles are suspended in a buffer that is isosmotic to the aqueous medium which was used to prepare the vesicles;
6) the Bragg Peak Signature of a vesicle composed of zwitterionic lipids should be substantially as depicted for SPLVs in FIG. 5, provided the vesicles are suspended in a buffer that is isosmotic to the aqueous medium which was used to prepare the vesicles; and
7) the Wide-angle X-ray Signature of a vesicle composed of zwitterionic lipids should be substantially as depicted for SPLVs in FIG. 6, provided the vesicles are suspended in a buffer that is isosmotic to the aqueous medium which was used to prepare the vesicles.

5.2.9.7. Interpretation of Results

Although not wishing to be limited or bound to any model or theory of operation of the present invention, we believe it will be helpful in interpreting the data to offer a possible theoretical explanation which can be summarized by the following model that may explain the differences between SPLVs and MLVs: the critical physical difference between SPLVs and other multilamellar lipid vesicles seems to be that SPLVs are characterized by a concentration of entrapped solute in each aqueous compartment that is substantially equal to the concentration of solute used to prepare the SPLVs and that unlike MLVs, SPLVs do not have an osmotic stress and, therefore, the bilayers are not under compression.

Knowledge of the internal composition of MLVs has been hampered by a lack of detailed information about how a dry lipid film reacts when exposed to solute-containing water. The prevailing view point has been summarized by Bangham et al. (1974, Meth. Membr. Biol. 1:1-68), who have written in a review about liposomes that "their usefulness as a model system derived from the fact that, as the dry phospho- and/or other lipids of biological origin undergo their sequence of molecular rearrangments, there is an opportunity for unrestricted (emphasis added) entry of solutes, e.g., isotopically labeled salts and proteins, between the planes of hydrophilic headgroups before an unfavorable entropy situation of an oil-water interface intervenes." They go on to say that there is a subsequent sealing of membranes into concentric, closed compartments, sequestering water and solutes which can thereafter only diffuse across compartments by crossing the bilayer walls. It was realized shortly after the development of the MLV procedure by Bangham and colleagues (1965, J. Mol. Biol. 13: 238-252), that lipid bilayers are highly permeable to water and relatively impermeable to alkali metal salts and a host of other solutes (Bangham et al., 1967, Chem. Phys. Lipids 1:225). This being the case, one may ask if the sealing of the outermost bilayer wall, upon hydration of a dry film, occurs prior to, or after the enclosed lipid has been fully hydrated If the sealing were to occur before full hydration, then water will continue to enter, via diffusion, because lipid headgroups have a high natural affinity for water (Parsegian et al., 1979, Proc. Natl, Acad. Sci. U.S.A. 76:2750-2754). However, salts and other such solutes may be excluded because of the relative impermeability of the outermost bilayer wall to these substances. The result would be a liposome in which the internal concentration of solute in the aqueous layers would be less than in the external bulk water. However, we know of no place in the literature where the question of the last four sentences is posed and discussed. We also know of no study which has examined the distribution of solute within liposomes formed by the MLV procedure . In the absence of such discussion it has generally been implicitly assumed that the aqueous solute concentration inside the liposomes is the same as the concentration of the fluid in which the liposomes are formed. For example, in an elegant study of the osmotic and swelling properties of liposomes, Bangham et al. (1967 supra) prepared liposomes in 50 mM KCl. "Aliquots (0.5 m$\pm$) were then pipetted into test tubes containing 1.5 ml of 250, 117, 50 and 17 mM tracer-free KCl and 1.5 ml water, respectively. These solutions represented osmotic stresses calculated to quarter, halve, leave unaltered and quadruple the osmotically active spaces inside . . . " The quantities involved reveal the authors to be assuming that the initial inner concentration is 50 mM, the same as the solution in which the liposomes were prepared.

In attempting to understand the differences between SPLVs and MLVs, one is forced to question if the internal MLV solute concentration is the same as that of the fluid used to prepare the liposomes. The high solute entrapment efficiency of SPLVs relative to MLVs raised the questions of where the entrapped solute was being held within the liposome. In the past, the low entrapment efficiency of MLVs seemed reasonable in view of an inadequate knowledge of specific adsorption by the bilayers, and the wide heterogeneity in the number of bilayers and sizes of the central aqueous volumes the liposomes. However, when MLVs and SPLVs were compared, these reasons were rapidly seen to be inadequate to explain the differences in entrapment efficiency. Electron microscopy of freeze-fractured liposomes and histogram analysis revealed similar size distribution. Specific adsorption could not account for the differences because both types of liposomes were made of the same lipid. X-ray diffraction revealed the repeat spaces to differ by only about 2 Å(25° C.). Using an established bilayer thickness of roughly 40 Å(Small, 1967, J. Lipid Res. 8: 551-557; Worcester, 1976, Neutron beam studies of Biological Membranes and membrane components; in biological membranes, vol. 3., Chapman and Wallach, eds., Academic Press.), this implied that the aqueous thickness between the bilayers differed by only 10-15%. Large differences in the central aqueous volume or in the number of layers could not be reconciled with the fact that the SPLV and MLV pellet volumes per unit mass of lipid were comparable to within 30%. It appeared that MLVs were somehow diluting the solutes or SPLVs were concentrating them.

The X-ray signatures described herein provided a rapid means of evaluating hypotheses as to the differences between the two types of liposomes. It was seen that an X-ray diffraction signature characteristic of MLVs could be obtained from SPLVS by increasing the external salt concentration and vice versa for MLVs by decreasing the external salt concentration relative to the concentration of the solution used to prepare the liposomes. This suggested that the X-ray signatures were sensitive to a concentration gradient. The LSS was reproduced with sucrose suggesting that the different X-ray signatures were primarily due to osmotic, as opposed to ionic, effects. Although changing the salt composition has strong effects on the LSS, MLVs and SPLVs still always differ. For example, the entrapment efficiency of MLVs is lower than that of SPLVs; this parameter would not change despite the change in the LSS. When liposomes were prepared in distilled water to remove any concentration gradients, both MLVs and SPLVs yielded an SPLV-like LSS, suggesting that MLVs had lower internal solute concentration. The ionophore, enzyme digestion and NMR experiments all supported the picture of an MLV which is under osmotic compression.

We have already discussed how the early sealing of a bilayer skin which excludes solute may lead to low solute concentrations in MLVs. By contrast, we envision SPLVs are resulting from the dynamics of coalescence of inverted water-in-ether droplets in which the lipid acts as a surfactant.

Importance of Osmotic Stress

The liposome literature is large. There are so many different ways to prepare liposomes, and so many lipids from which to prepare them, that it is fair to ask: what variables are important? Obviously, the answer to this question depends on the use which is intended for the liposomes. However, one of the most often stated reasons for studying liposomes is for the use as an in vivo drug carrier. We were alerted to the differences between MLVs and SPLVs by their vastly different pharmacokinetics. SPLVs are highly effective in curing infectious diseases, whereas MLVs are not. SPLVs are also far more stable than MLVs. Given these important differences, let us now consider the variables whose investigation forms the vast bulk of the liposome literature.

Literally speaking, both SPLVs and MLVs are multilamellar. Much of the literature is concerned with the differences between multilamellar and unilamellar liposomes. These differences are important but do not differentiate MLVs from SPLVs. One of the reasons given for using unilamellar liposomes is that they can have a high entrapment efficiency (e.g., Szoka and Papahadjopoulos, 1978, Proc. Natl. Acad. Sci. U.S.A. 79: 4194-4198). While this is true, in light of the results presented herein, this is not a compelling argument against the use of multilamellar vesicles, since SPLVs also have a high entrapment efficiency.

Another highly discussed variable is the size of the liposomes. Again, this is important but does not differentiate MLVs from SPLVs. Yet another variable involves purity of the lipids and reagents. We certainly would never imply that this is an unimportant variable. However, the studies described herein were done with EPC straight from the bottle, without additional purification steps; solvents were of reagent grade and used without additional purification. Exposure to air was minimized but by no means eliminated. Yet the reproducibility of the distinctions between MLVs and SPLVs has been excellent. Again, we do not mean to belittle problems of contamination. We only wish to emphasize that this variable is secondary with respect to the structural distinctions between SPLVs and MLVs. It cannot for instance, account for the storage stability differences between the two types of liposomes.

The lipid composition of liposomes is the concern of an enormous literature. But both MLVs and SPLVs can be made of EPC. Review of the experiments discussed Section 5.2 will show that, within narrow limits, the lipid composition can be varied without erasing the distinction between MLVs and SPLVs. Neither the buffering system, nor the specific ionic composition is of paramount importance. The most important variable appears to be the sign and magnitude of the osmotic stresses exerted upon liposomes. Although numerous studies have used the osmotic properties of liposomes, this osmotic stress has not been recognized as a variable, perhaps the most important variable, with which to differentiate certain liposomal types.

Why is the osmotic stress important? More fundamentally, what do the differences in the X-ray signature tell us? We only know partial answers to these questions. Recent research in osmotically induced fusion (Cohen et al., 1980, J. Gen. Physiol. 75:251-270; and 1982 Science 217:458-460; Zimmerberg et al., 1980) has empirically demonstrated the importance of understanding osmotic stress across bilayers. The bulk of the liposome literature deals with the chemical properties of bilayers; relatively little emphasis has been placed on the material properties of lipid bilayers when stressed in various ways. Consider an MLV under osmotic stress of a sign such as to make the liposome expand. This is the case for FIG. 10. One sees that the LSS of MLVs under this type of stress looks like the LSS of a normal SPLV. The liposome has surely dilated when suspended in the hypotonic buffer. In doing so the bilayer shell must increase their area. In so far as lipids are constrained to a given bilayer shell, this means the area per molecule must also increase. This has enormous implications because once the area per molecule changes then the interaction of all the forces in the system must change. In the various models of the statistical mechanics of membranes, an order parameter that has a profound effect is the area per molecule. This has been emphasized, for example by Nagle (1980, Ann. Rev. Phys. Chem. 31:157-195), by Israelachvili et al. (1980 Biophys. 13:121-200), by Pink (1982 Theoretical models of phase changes in one- and two- component lipid bilayers; in Biological Membranes, vol. 4, D. Chapman, ed., Academic Press, N.Y. pp. 131-178),and by Kirk et al., (1984), Biochem. 23:1093-1102). As the area/molecule changes, the hydrocarbon order parameter must also change. Several studies (see Israelachivili et al., 1980 supra) have examined the hydrocarbon order parameter state of inclination from the membrane normal) vs. carbon number down the chain. We know of no studies which have done this for stressed bilayers. The Wide-angle X-ray signature (FIG. 6), suggests this order parameter profile changes under stress. In fact, in most statistical mechanical models, the area/molecule is introduced as a fundamental constraint or as a parameter derived from an independent calculation of the head-group interactions. The change in the area/molecule is likely to affect the hydrogen bonding and steric interactions between head-groups. It must also affect the magnitude of the interaction with water: it is known that the thickness of a bilayer is coupled to the hydration of the multilameter lattice. The area/molecule decreases as water is withdrawn from the lattice (Luzzati, 1968 X-ray diffraction studies of lipid water systems; in Biological membranes, Vol 1., D. Chapman, ed., Academic Press, N.Y. pp. 71-123; Rand, 1981 Ann. Rev. Biophys Bioeng. 10:277-314). We suggest the coupling may be reversible, i.e., that expanding or shrinking the area/molecule may affect the interaction with water. In sum, the entire molecular basis of the bilayer is affected by the osmotic stress. As a result, osmotically compressed liposomes behave differently than unstressed liposomes even though both are composed of the same species of lipids. Note, incidentally, in FIGS. 9-11 that it is the direction and magnitude of the osmotic gradient, which seem most important.

An MLV is a many layered vesicle with one small core. Assume this core is either iso-osmotic to the suspending buffer or, where bent, is bent into radii so small that it is constrained against collapse (recall that unilamellar vesicles have a minimum size of roughly a few hundred Å (Mason & Huang, 1978, Annals N.Y. Acad. Sci. 308: 29-49. Further assume, as we believe is the case for MLVs, that the outer layers are solute depleted. The osmotic stress is of a direction such as to collapse the outer layers by withdrawal of water. However, as opposed to a unilamellar vesicle, the outer layers cannot collapse because they are wrapped around a "rigid" core. The thickness of the water layers between the bilayers cannot shrink appreciably because, as Parsegian, Rand and coworkers have shown (see Rand, 1981, Ann. Rev. Biophys. Bioeng. 10:277-314 for a review) very strong repulsive hydration forces keep the bilayers apart. Parsegian et al. (1979, Proc. Natl. Acad. Sci. U.S.A. 76: 2750-2754) have measured the repeat spacing for EPC in pure water at 25° C.; they obtain a value of 62.5 Å. Reference to FIG. 4 shows the MLV value to be 61.7 Å, indicating that the MLV layers are collapsed against the "hard-wall" of the hydration force. (Note, incidentally, that the repeat spacing of either MLVs or SPLVs in pure water, i.e., unstressed bilayers, as shown in FIG. 14, is about 62.5 Å at 25° C.). The outer layers of the MLV, in fact, are under a stress which has hitherto been rarely considered in liposomes: the bilayers are under compression. In complete contrast, the bilayers of SPLVs are uncompressed.

Solute depletion of the outer and possibly many inner layers of MLVs has many other implications. For example, one of the solutes most commonly involved is NaCl. The Nernst equations states that an imbalance of the concentrations, $C^1$ and $C^2$, of an ionic species across a membrane gives rise to an electrical potential $$\Delta\phi = -(RT/zF) \ln (c_2/C_1) \quad \text{(Eq. 4)}$$

Where $R$ = the gas constant
$T$ = temperature
$z$ = ionic charge
$\Delta\phi$ = electrical potential
and $F$ = Faraday's number.

Now the bilayer permeability coefficient for $Na^+(10^{-12}$ cm/S) is almost 2 orders of magnitude smaller than for $Cl^-$. This means that the $Na^+$ gradient cannot relax in weeks; the $Cl^-$ gradient relaxes almost 100 times faster, leading to a Nernst potential across the bilayer of MLVs. The biological implications of this are hard to access but may be significant. The potential may be responsible for the rheological differences between MLV and SPLV pellets.

10 5 3. USES OF SPLVS

SPLVs are particularly useful in systems where the following factors are important: stability during storage and contact with body fluids; a relatively high degree of encapsulation; cost-effectiveness; and the preservation of the biologically active form of the entrapped compound.

Furthermore, depending upon the mode of administration in vivo, SPLVs can be resistant to rapid clearance (e.g., wherein sustained delivery is important) or can be delivered to the cells of the RES.

As a result, the SPLVs of the invention are usefully employed in a wide variety of systems. They may be used to enhance the therapeutic efficacy of medications, to cure infections, to enhance enzyme replacement, oral drug delivery, topical drug delivery, for introducing genetic information into cells in vitro and in vivo, for the production of vaccines, for the introduction of recombinant deoxyribonucleic acid segments into cells, or as diagnostic reagents for clinical tests following release of entrapped "reporter" molecules. The SPLVs can also be employed to encapsulate cosmetic preparations, pesticides, compounds for sustained slow release to effect the growth of plants and the like.

The methods which follow, while described in terms of the use of SPLVs, contemplate the use of SPLVs or any other liposome or lipid vesicle having functional characteristics similar to those of SPLVs.

5.3.1. DELIVERY OF BIOACTIVE COMPOUNDS

SPLVs demonstrate a number of characteristics which make them particularly suitable as carriers for delivery systems in vivo:

(A) When administered by a non-intravenous or non-intraperitoneal route, SPLVs are resistant to clearance. When SPLVs are administered to an organism by routes including but not limited to subcutaneously, topically, intramuscularly, and the like, both the lipid component and the entrapped active ingredient are retained in the tissues and by the cells to which they are administered;

(B) SPLVs can be engineered to provide sustained release. The stability of SPLVs is "adjustable" in that SPLVs are very stable during storage and are stable in the presence of body fluids but when administered in vivo a slow leakage of the active ingredient permits the sustained release of the active ingredient;

(C) Because of the high level of entrapment and stability when administered, effective doses of the active ingredient are released; and (D) The production of SPLVs is very cost effective in that stability of the vesicles is achieved without incorporating expensive stabilizers into the bilayers.

5.3.1.1. Delivery in Vitro

Delivery of compounds to cells in vitro (e.g., animal cells, plant cells, protists, etc.) generally requires the addition of the SPLVs containing the compound to the cells in culture. Still another benefit of SPLVs is that SPLVs interact with cells such that a relatively large portion of the materials encapsulated inside the vesicle is dispersed throughout the cytoplasm of the cells rather than being limited to phagocytic vesicles. When SPLVs are mixed with cells the two appear to coalesce. By coalescence, SPLVs, unlike MLVs, interact with cells in vitro so that all the cells contain at least some of the materials originally entrapped in the SPLVs. This material appears to be distributed throughout each cell and not limited to just the phagocytic vesicles. This can be demonstrated by incorporating ferritin in the aqueous phase of a SPLV preparation. After coalescence with a cell in culture, ultrastructural analysis reveals that the ferritin is distributed throughout the cytosol and is not bound by intracellular membranes. While this phenomenon can be shown to occur with MLVs a greater quantity of material can be transferred by SPLVs.

5.3.1.2. Delivery in Vivo

SPLVs, however, can also be used to deliver compounds in vivo in animals (including man), plants and protists. Depending upon the purpose of delivery, the SPLVs may be administered by a number of routes: in man and animals this includes but is not limited to injection (e.g., intravenous, intraperitoneal, intramuscular, subcutaneous, intraarticular, intraauricular, intramammary, intraurethrally, etc.), topical application (e.g., on afflicted areas), and by absorption through epithelial or mucocutaneous linings (e.g., ocular epithelia, oral mucosa, rectal and vaginal epithelial linings, the respiratory tract linings, nasopharyngeal mucosa, intestinal mucosa, etc.); in plants and protists this includes but is not limited to direct application to organism, dispersion in the organism's habitat, addition to the surrounding environment or surrounding water, etc.

The mode of application may also determine the sites and cells in the organism to which the compound will be delivered. For instance, delivery to a specific site of infection may be most easily accomplished by topical application (if the infection is external). Delivery to the circulatory system (and hence reticuloendothelial cells), may be most easily accomplished by intravenous, intraperitoneal, intramuscular, or subcutaneous injections.

Since SPLVs allow for a sustained release of the compound, doses which may otherwise be toxic to the organism may be utilized in one or more administrations to the organism.

The following experiments demonstrate some of these characteristics of SPLVs when administered topically onto the eyes of test animals. The SPLVs used in these experiments were prepared as previously described except that the lipid bilayer and the active ingredient were each radiolabeled in order to trace these components in the eye tissues over a period of time.

SPLVs were prepared using 100 mg egg phosphatidylcholine (EPC) and 100mg gentamicin sulfate. The lipid component was radiolabeled by the incorporation of trace amounts of $^{125}$I-phosphatidylethanolamine ($^{125}$I-PE) into the bilayers, whereas the active ingredient in the aqueous phase was radiolabeled by the addition of $^{125}$I-gentamicin sulfate ($^{125}$I-GS). The SPLVs were washed with buffer repeatedly in order to effectively remove unincorporated or unencapsulated materials.

An aliquot of the SPLV preparation was removed and extracted in order to separate the organic phase from the aqueous phase. The radioactivity of each phase was measured in order to determine the initial ratio of $^{125}$I-PE:$^{125}$I-GS (cpm (counts per minute) in the lipid phase:cpm in the aqueous phase) which was incorporated into the SPLVs.

The extraction was done as follows: 0.8 ml of 0.4M NaCl (aqueous), 1 ml chloroform, and 2 ml methanol were mixed to form a homogeneous phase. Then 4 µl of the radiolabeled SPLVs were added and mixed; as the SPLV components dissolved into the organic phase and into the aqueous phase, the mixture, which was initially turbid, became clear. The phases were separated by adding and mixing 1 ml 0.4M NaCl (aqueous) and 1 ml chloroform, which was then centrifuged at 2,800×g for 5 minutes. An aliquot (1ml) of each phase was removed and the radioactivity (in cpm) was measured. (The initial ratio of $^{125}$I-PE:$^{125}$I-GS was 1.55:1).

Fifteen adult female Swiss Webster mice were anesthetized and restrained (in order to prevent them from wiping their eyes). Equal aliquots (2µl) of the radiolabeled SPLVs in suspension were topically applied to each eye. Groups of three animals were then sacrificed at each of the following points: 1, 2, 3, 18, and 24 hours. Nine female Swiss Webster mice (controls) were treated identically except that equal aliquots (2 µl) of an aqueous solution of radio-labeled gentamicin sulfate were applied topically to each eye. Groups of three control animals were sacrificed at the end of 1, 4, and 8 hours.

Immediately after sacrifice the eyelids of the animals were removed, minced, and extracted (using the procedure previously described) in order to separate the aqueous components from the lipid components. The radioactivity of each phase was determined (as well as the total number of radioactive counts recovered). The radioactivity measured in the lipid phase is an indication of the retention of SPLV lipids by the eye tissue, whereas the radioactivity measured in the aqueous phase is an indication of the retention of gentamicin in the eye tissue. FIG. 16 graphically demonstrates the retention of each component in the eyelid tissue (expressed as the percent of the original number of cpm applied to the eye).

FIG. 16 clearly demonstrates the retention of the SPLV lipid component in the eyelid tissue over a 24 hour period, and the sustained release of gentamicin from the SPLVs over a 24 hour period (as reflected by the percent gentamicin retained in the eyelid tissue during this time). FIG. 17 also demonstrates that unencapsulated gentamicin (aqueous gentamicin administered topically) is rapidly cleared from the eyelid tissue. For example, gentamicin in solution (control) was cleared from the eyelid tissue within 4 hours (less than 5% of the gentamicin remained in the eyelid tissue). On the other hand, more than 50% of the SPLV-encapsulated gentamicin was retained by the eyelid tissue in this 4 hour period; in fact, at the end of 24 hours more than 15% of the SPLV-encapsulated gentamicin was retained by the eyelid tissue. This indicates that approximately 85% of the SPLV-encapsulated gentamicin was released over a 24 hour period whereas 95% of the unencapsulated gentamicin sulfate was cleared within a 4 hour period.

Table IV compares the ratio of the SPLV lipid phase:aqueous phase retained in the eyelid tissue at each time point. An increase in this ratio indicates release of gentamicin from the SPLVs.

TABLE IV

SUSTAINED RELEASE OF SPLV-ENCAPSULATED GENTAMICIN AFTER TOPICAL APPLICATION IN EYES OF MICE

| Time Post-Application | Total SPLV Components Recovered from Eyelids (% Initial Dose) | Ratio of SPLV Lipid: Aqueous Phase Retained In Eyelids ($^{125}$I-PE:$^{125}$I-GS) |
| --- | --- | --- |
| 0 | 100 | 1.55 |
| 1 hr | 100 | 2.1 |
| 3 hr | 100 | 2.82 |
| 18 hr | 94 | 6.89 |
| 24 hr | 85.1 | 7.17 |

The bioactivity of the SPLV-encapsulated gentamicin sulfate which was retained by the eyelid tissue was also evaluated. Gentamicin sulfate was recovered from the eyelid tissues by removing an aliquot from the aqueous phase of the eyelid extracts prepared 3 hours after the SPLV-encapsulated gentamicin sulfate was applied to the eye. The aqueous phase was serially diluted and 2 µl aliquots were placed onto *Staphylococcus aureus* lawns on agar plates; after 24 hours incubation the zones of inhibition were measured. The gentamicin sulfate recovered from the eyelid tissue extracts of animals treated with SPLV-encapsulated gentamicin sulfate fully retained its bioactivity.

The difference in the behavior of SPLVs and MLVs in vivo can best be seen by examining the pharmacokinetics of drugs entrapped within each type of vesicle. We have entrapped gentamicin in MLVs and SPLVs and studied the pharmacokinetics of that drug within the liver and spleen following intraperitoneal injection in mice (FIG. 17a and b). The results demonstrated in FIG. 17a and b demonstrate that these two vesicles are handled in drastically different ways. Actually, in other experiments active antibiotic administered in SPLVs has been found in the spleen 5 weeks after injection. Little antibiotic given in MLVs can be observed past 7 days.

The sections which follow describe some overall schemes in which SPLVs may be used and demonstrate but do not limit the scope of the present invention.

5.3.2. Treatment of Pathologies

A number of pathological conditions which occur in man, animals and plants may be treated more effectively by encapsulating the appropriate compound or compounds in SPLVs. These pathologic conditions include but are not limited to infections (intracellular and extracellular), cysts, tumors and tumor cells, allergies, etc.

Many strategies are possible for using SPLVs in the treatment of such pathologies; a few overall schemes are outlined below which are particularly useful in that they take advantage of the fact that SPLVs when administered in vivo are internalized by macrophages.

In one scheme, SPLVs are used to deliver therapeutic agents to sites of intracellular infections. Certain diseases involve an infection of cells of the reticuloendothelical system, e.g., brucellosis. These intracellular infections are difficult to cure for a number of reasons: (1) because the infectious organisms reside within the cells of the reticuloendothelial system, they are sequestered from circulating therapeutic agents which cannot cross the cell membrane in therapeutically sufficient concentrations, and, therefore, are highly resistant to treatment; (2) often the administration of toxic levels of therapeutic agents are required in order to combat such infections; and (3) the treatment has to be completely effective because any residual infection after treatment can reinfect the host organism or can be transmitted to other hosts.

According to one mode of the present invention, SPLVs containing an appropriate biologically active compound are administered (preferably intraperitoneally or intravenously) to the host organism or potential host organism (e.g., in animal herds, the uninfected animals as well as infected animals may be treated). Since phagocytic cells internalize SPLVs, the administration of an SPLV-encapsulated substance that is biologically active against the infecting organism will result in directing the bioactive substance to the site of infection. Thus, the method of the present invention may be used to eliminate infection caused by a variety of microorganisms, bacteria, parasites, fungi, mycoplasmas, and viruses, including but not limited to: *Brucella sop., Mycobacterium spp., Salmonella spp., Listeria spp., Francisella spp., Histoplasma spp., Corynebacterium spp., Coccidiodes spp., Pseudomonas spp.*, and lymphocytic choriomeningitis virus.

The therapeutic agent selected will depend upon the organism causing the infection. For instance, bacterial infections may be eliminated by encapsulating an antibiotic or combinations of antibiotics. The antibiotic can be contained within the aqueous fluid of the SPLV and/or inserted into the vesicle bilayer. Suitable antibiotics include but are not limited to: penicillin, ampicillin, hetacillin, carbencillin, ticarcillin, nafcillin, tetracycline, tetracycline hydrochloride, oxytetracycline hydrochloride, chlortetracycline hydrochloride, 7-chloro-6-dimethyltetracycline, doxycycline monohydrate, methacycline hydrochloride, minocycline hydrochloride, rolitetracycline, dihydrostreptomycin, streptomycin, gentamicin, kanamycin, tobramycin, neomycin, erythromycin, carbomycin, oleandomycin, troleandomycin, Polymyxin B collistin, cephalothin sodium, cephaloridine, cephaloglycin dihydrate, and cephalexin monohydrate.

We have demonstrated the effectiveness of such treatments in curing brucellosis, salmonellosis and pyelonephritis (see Examples, infra). By the procedure of this invention, the effectiveness and duration of action are prolonged. It is surprising that this system is effective for treating infections which do not respond to known treatments such as antibiotics entrapped in MLVs. Successful treatment is unexpected since any small remaining infections will spread and the infectious cycle will commence again. We have also demonstrated success in treating lymphocytic choriomeningitis virus infection.

Of course, the invention is not limited to treatment of intracellular infections. The SPLVs can be directed to a variety of sites of infection whether intracellular or extracellular. For instance, in another embodiment of the present invention, macrophages are used to carry an active agent to the site of a systemic extracellular infection. According to this scheme, SPLVs are used to deliver a therapeutic substance to uninfected macrophages by administering the SPLVs in vivo (preferably intraperitoneally or intravenously). The macrophages will coalesce with the SPLVs and then become "loaded" with the therapeutic substance; in general, the macrophages will retain the substance for approximately 3 to 5 days. Once the "loaded" macrophages reach the site of infection, the pathogen will be internalized by the macrophages. As a result, the pathogen will contact the therapeutic substance contained within the macrophage, and be destroyed. This embodiment of the invention is particularly useful in the treatment of pyelonephritis.

If the site of infection or affliction is external or accessible the SPLV-entrapped therapeutic agent can be applied topically. A particularly useful application involves the treatment of eye afflictions. In the case of ocular afflictions, SPLVs containing one or more appropriate active ingredients may be applied topically to the afflicted eye. A number of organisms cause eye infections in animals and man. Such organisms include but are not limited to: *Moraxella spp., Clostridium spp., Corynebacterium spp., Diplococcus spp., Flavobacterium spp., Hemophilus spp., Klebsiella spp., Leptospira spp., Mycobacterium spp., Neisseria spp., Propionibacterium spp., Proteus spp., Pseudomonas spp., Serratia spp., Escherichia spp., Staphylococcus spp., Streptococcus spp.* and bacteria-like organisms including *Mycoplasma spp.* and *Rickettsia spp.* These infections are difficult to eliminate using conventional methods because any residual infection remaining after treatment can reinfect through lacrimal secretions. We have demonstrated the use of SPLVs in curing ocular infections caused by *Moraxella bovis* (see examples, *infra*).

Because SPLVs are resistant to clearance and are capable of sustained release of their contents, SPLVs are also useful in the treatment of any affliction requiring prolonged contact with the active treating substance. For example, glaucoma is a disorder characterized by a gradual rise in intraocular pressure causing progressive loss of peripheral vision, and, when uncontrolled, loss of central vision and ultimate blindness. Drugs used in the treatment of glaucoma may be applied topically as eyedrops. However, in some cases treatment requires administering drops every 15 minutes due to the rapid clearing of the drug from the eye socket. If an affliction such as glaucoma is to be treated by this invention therapeutic substances as pilocarpine, Floropryl, physostigmine, carcholin, acetazolamide, ethozolamide, dichlorphenamide, carbachol, demecarium bromide, diisopropylphosphofluoridate, ecothioplate iodide, physostigmine, or neostigmine, etc. can be entrapped within SPLVs which are then applied to the affected eye.

Other agents which may be encapsulated in SPLVs and applied topically include but are not limited to: mydriatics (e.g., epinephrine, phenylepinephrine, hydroxy amphetamine, ephedrine, atropine, homatropine, scopolamine, cyclopentolate, tropicamide, encatropine, etc.); local anesthetics; antiviral agents (e.g., idoxuridine, adenine arabinoside, etc.); antimycotic agents (e.g., amphoteracin B, natamycin, pimaricin, flucytosine, nystantin, thimerosal, sulfamerazine, thiobendazole, tolnaftate, grisiofulvin, etc.); antiparasitic agents (e.g., sulfonamides, pyrimethamine, clindamycin, etc.); and anti-inflammatory agents (e.g., corticosteriods such as ACTH, hydrocortisone, prednisone, medrysone, beta methasone, dexamethasone, fluoromethalone, triamcinalone, etc ).

The following Examples are given for purposes of illustration and not by way of limitation on the scope of the invention.

6. EXAMPLE: PREPARATION OF SPLVS BY THE MONOPHASIC SOLVENT SYSTEM PROCESSES

In the subsections which follow, SPLVs were prepared by solubilizing a phospholipid in ethanol or other appropriate solvent, adding an aqueous phase and the material to be entrapped, sonicating the mixture at 54° C. while drying under nitrogen until a film formed. The film containing both the lipid and the material to be entrapped was resuspended in an aqueous buffer and agitated in order to form the SPLVs.

6.1. SPLVs Containing Tetracyclines

A sample containing 127 micromoles of egg phosphatidylcholine (EPC) in chloroform was taken to dryness in a round bottom flask. A 5 ml aliquot of ethanol was added to the flask to resuspend the lipid. A solution (0.5 ml) containing 100 mg of doxycycline monohydrate at approximately pH 7 in physiologic saline was pipetted into the glass vessel containing the ethanol solution of lipid. The monophase was placed in a bath sonicator type 10536 (Laboratories Supplies Co., Inc.) for several minutes, (80 kHz frequency; output 80 watts), at 54° C., while being dried to a film by passing thereover a gentle stream of nitrogen.

To the film remaining 0.3–10.0 ml of physiologic saline was added and the mixture was vortexed while being dried under nitrogen in order to suspend the film and form the SPLVs. The preparation was centrifuged at 10,000 ×g for 10 minutes to remove the non-entrapped doxycycline. This wash was repeated three times. The resulting pellet was suspended in 10 ml of physiologic saline.

The same procedure was used to prepare SPLVs containing tetracycline by substituting tetracycline for doxycycline.

6.2. SPLVs Containing Gentamicin and Nafcillin

SPLVs containing both gentamicin and nafcillin were prepared as described above with the following modifications: a 5 ml ethanol solution containing 100 mg EPC was prepared and the following two solutions were added to the lipidethanol solution simultaneously: 100 mg gentamicin sulfate in 0.15 ml PBS$^-$(phosphate buffered saline lacking divalent cations) and 100 mg nafcillin in 0.15 ml PBS. The mixture was evaporated at 54° C. and the SPLVs were formed as described above.

6.3. SPLVs Containing Gentamicin

SPLVs containing gentamicin (without nafcillin) were prepared by the same procedure described in Section 6.2 except that 200 mg gentamicin sulfate in 0.3 ml PBS was added to the 5 ml ethanol-EPC solution.

6.4 SPLVs Containing Chloramphenicol

SPLVs containing chloramphenicol were prepared as described in Section 6.1. except that chloramphenicol (crystalline) was substituted for doxycycline.

6.5. SPLVs Containing Tobramycin

SPLVs containing tobramycin were prepared as follows: 300 mg EPC in chloroform rotoevaporated to dryness and resuspended in 30 ml ethanol. 300 mg tobramycin were suspended in PBS$^-$(PBS without divalent cations) to a final volume of 0.9 ml. The two solutions were mixed together by vortexing and then rotoevaporated to dryness in a water bath at 50°-55° C. The final film was reususpended in 10 ml PBS$^-$, washed three times at 10,000 ×g for 10 minutes centrifugation. Each supernatant was discarded and the pellet resuspended in 10 ml fresh PBS$^-$. After the third wash, the final pellet was resuspended to a final volume of 10 ml, yielding a final tobramycin concentration of 0.8 mg/ml as determined by standard microbiological assay techniques.

6.6. SPLVs Containing Ticarcillin

SPLVs containing ticarcillin were prepared as follows: 2 grams EPC in chloroform was rotoevaporated to dryness and resuspended in 200 m±ethanol. 2 grams ticarcillin sodium was added to the EPC-ethanol mixture to form a solution. 6 ml PBS$^-$ were then added to the solution and the solution rotoevaporated to dryness in a water bath at 50°-55° C. The final film was resuspended in 30 ml PBS$^-$ and diluted to 100 ml in PBS$^-$. The preparation was washed three times at 10,000 ×g for 10 minutes centrifugation. Each supernatant was discarded and the pellet resuspended in fresh PBS$^-$. After the final wash, the pellets were pooled and the final volume adjusted to 10 ml, yielding a final Ticarcillin concentration of 10 mg/ml as determined by standard microbiological assay techniques.

6.7. SPLVs Containing Ticarcillin and Tobramycin

SPLVs containing both ticarcillin and tobramycin were prepared as follows: 200 mg EPC in chloroform was rotoevaporated to dryness and resuspended in 20 ml ethanol. 200 mg ticarcillin sodium salt was dissolved in this solution. 200 mg tobramycin was dissolved in 0.6 ml PBS$^-$ and mixed with the above solution by vortexing. The mixture was rotoevaporated to dryness in a water bath at 50°-55° C. The final film was resuspended in 10 ml PBS$^-$ and the preparation washed three times at 10,000 ×g for 10 minutes centrifugation. Each supernatant was discarded and the pellet resuspended to a final volume of 10 ml fresh PBS$^-$. After the final wash, the pellet was resuspended to a final volume of 10 ml in PBS$^-$, yielding a final tobramycin concentration of 0.8 mg/ml and ticarcillin concentration of 0.8 mg/ml as determined by standard microbiological assay techniques.

6.8. Alternative Methods of Preparing SPLVs

SPLVs were prepared as follows: 127 micromoles of EPC in chloroform was taken to dryness by rotoevaporation. The lipid was resuspended in 5 m±of ethanol and to this was added 0.2 ml water containing $^3$H-inulin. The resulting preparation was treated as follows to examine the encapsulation efficiency of the resulting liposomes:

(1) Vortexing the preparation while drying under nitrogen;
(2) Hand-shaking the preparation while drying under nitrogen;
(3) Drying under nitrogen with no concurrent agitation;
(4) Rotoevaporating under vacuum with no agitation;
(5) Sonicating while drying under nitrogen.

All techniques were carried out at a temperature range of between 50°-60° C. To the dried preparations were added 10 m±of water containing $^{14}$C-sucrose. All preparations were centrifuged at 10,000 ×g for 10 minutes with three washes.

Final entrapment was determined by liquid scintillation counting techniques using double channel counting. Values expressed as percent entrapment means the perentage of radioactive material in the pelleted liposomes (cpm) relative to the initial amount of radioactive material in the preparation (cpm). The results are shown in Table V.

TABLE V

| | Encapsulation Efficiency[a] | |
|---|---|---|
| Procedure | $^3$H-Inulin | $^{14}$C-Sucrose |
| (1) Vortexing while drying under nitrogen | 31.0 | 2.3 |
| (2) Hand-shaking while drying under nitrogen | 29.7 | 2.4 |
| (3) Stationary drying under nitrogen | 32.6 | 2.2 |
| (4) Rotoevaporation | 32.2 | 2.2 |
| (5) Sonicating while drying under nitrogen[b] | 44.5 | 2.4 |

EFFICIENCY OF ENTRAPMENT IN SPLVS MADE BY ALTERNATIVE METHODS

[a]Figures presented represent percent entrapment of the starting volumes used.
[b]Preferred embodiment.

6.9. Preparation of SPLVs Using Various Solvent Systems

The following example shows the encapsulation efficiency of SPLVs that are prepared in different solvent systems. The criteria used for the evaluation of the solvents tested in this example were the following: (1) 5 ml of the organic solvent must form a monophasic solution with 0.2 ml aqueous solvent and (2) EPC must be soluble in the monophase. Of course if less lipid is used to make the SPLVs the volumes used in the test would be adjusted accordingly.

Seven organic solvents were evaluated according to the above criteria and the results are shown in Table VI.

TABLE VI

| SELECTION OF SOLVENTS | | |
|---|---|---|
| Solvent | Criterion 1<br>5 ml of solvent are miscible with 0.2 ml H$_2$O | Criterion 2<br>At 50°-60° C., solvent, lipid and H$_2$O are miscible |
| Ethanol | Yes | Yes |
| Acetone | Yes | Yes |
| Dimethylformamide | Yes | No |
| DMSO | Yes | No |
| Acetonitrile | No | Not Done |
| 2-Propanol | Yes | Yes |
| Methanol | Yes | Yes |

These results indicate that four of the solvents examined are suitable to use as solvent for preparation of SPLVs (i.e., ethanol, acetone, 2-propanol or methanol).

In order to determine the encapsulation efficiencies achieved when using the four solvent systems, a sample of 127 micromoles of EPC in chloroform was rotoevaporated to dryness in a round bottom flask, then resuspended in one of the following organic solvents: ethanol, acetone, 2-propanol, or methanol. to this preparation was added 0.2 ml of an aqueous phase containing $^3$H-inulin. This monophase was sonicated at 50°-60° C., and dried under nitrogen. The resulting film was resuspended in 10 ml of water containing $^{14}$C-sucrose after being subjected to centrifugation three times at 10,000 ×g. Final entrapment of $^3$H-inulin and $^{14}$C-sucrose sucrose were determined by dual channel liquid scintillation technique (Dual Beckman LS 6800). The results are shown in Table VII.

TABLE VII

| ENCAPSULATION EFFICIENCIES OF VARIOUS SOLVENT SYSTEMS | | |
|---|---|---|
| | Encapsulation Efficiency$^a$ | |
| Organic Solvent | $^3$H-Inulin$^b$ | $^{14}$C-Sucrose$^c$ |
| Ethanol | 45.8 | 2.8 |
| Acetone | 38.3 | 2.3 |
| 2-Propanol | 23.7 | 1.3 |
| Methanol | 44.5 | 2.4 |

$^a$Values are expressed as percent entrapped meaning the proportion of radioactive material in the pelleted liposomes (cpm) relative to the starting amount of radioactive material (cpm) added to the preparation.
$^b$Added to the monophase.
$^c$Added to the aqeous resuspension buffer.

7. EXAMPLE: PREPARATION OF SPLVS BY THE EMULSIFICATION PROCESSES

As explained in Section 5.1.2. one basic process for preparing SPLVs involves dissolving a lipid or mixture of lipids into an organic solvent, adding an aqueous phase and the material to be encapsulated, and sonicating the mixture while sonicating by any evaporative technique. The SPLVs used in all of the examples contained herein were prepared as described in the following subsections (however any process which yields SPLVs may be used).

7.1. SPLVs Containing Antibiotics

A 5 ml diethyl ether solution of 100 mg lecithin was prepared. The mixture was placed in a round-bottom flask. Then a solution (0.3 ml) containing 100 mg of streptomycin sulfate at pH 7.4 in 5 mM HEPES (4-[2-Hydroxyethyl]piperazino 2-ethane sulfonic acid)/0.0725 M NaCl/0.0725 M KCl was pipetted into the glass vessel containing the diethyl ether solution of lipid. The mixture was placed in a bath sonicator (Laboratory Supplies Co., Inc.) type 10536 for several minutes, (80 kHz frequency:output 80 watts) while being dried to a viscous paste by passing thereover a gentle stream of nitrogen.

To the viscous paste remaining was added 10 ml of 5 mM HEPES. The resulting SPLV preparation, containing streptomycin, was suspended in the buffer solution, shaken for several minutes on a vortex mixer, and freed of nonencapsulated streptomycin by centrifuging at 12,000 ×g for 10 minutes at 20° C. The resulting cake was suspended in 0.5 ml of 5 mM HEPES.

The procedure described above was followed except that streptomycin was substituted by each one of the following: dihydrostreptomycin, gentamicin sulfate, ampicillin, tetracyline hydrochloride, clindamycin and kanamycin.

7.2. Preparation of SPLVs Containing Gentamicin or Nafcillin

A 5 ml diethyl ether solution of 100 mg egg phosphatidylcholine (EPC, or egg lecithin) was prepared. The mixture was placed in a round bottom flask. Then a solution (0.3 ml) containing 200 mg of gentamicin or nafcillin in phosphate buffered saline (PBS, pH 7.2) was pipetted into the flask containing the deithyl ether solution of lipid. The mixture was placed in a bath sonicator (Laboratory Supplies Co., Inc., type 10536) for several minutes (80 kHz frequency; output 80 watts) while being dried to a viscous paste by passing a gentle stream of nitrogen over the mixture.

To the viscous part remaining, 10 ml of PBS was added. The resulting SPLV preparation containing either nafcillin (SPLV/Naf) or gentamicin (SPLV/Gent) was suspended in PBS, shaken and freed of nonencapsulated antibiotic by centrifugation at 12,000 x g for 10 minutes at 20° C. The resulting pellet was washed one more time and resuspended in 0.5 ml PBS.

7.3. Preparation of SPLVs Containing Both Gentamicin and Nafcillin

In order to prepare SPLVs containing both nafcillin and gentamicin, the procedure described above was followed with the following modifications: after the EPC was dispersed in deithyl ether, two solutions, one of each antibiotic, were added quickly and simultaneously, each solution consisted of 100 mg antibiotic (nafcillin or gentamicin) dissolved in 0.15 ml PBS. After the addition of the two solutions, the preparation was sonicated, evaporated, and washed two times as previously described. The resulting SPLVs entrapped both gentamicin and nafcillin (SPLV/Gent-Naf).

7.4. SPLVs Containing Gentamicin and Clindamycin

SPLVs containing both gentamicin and clindamycin were prepared as described in Section 7.3 except 100 mg clindamycin was used in place of nafcillin.

7.5. SPLVs Containing Other Membrane Constituents

The process described in Section 7.1 was followed except that any one of the following was added with the egg lecithin: (1) phosphatidic acid to give a molar ratio of 8:2 (lecithin:dicetylphosphate); (2) stearylamine to give a molar ratio of 8:2 (lecithin: stearylamine); cholesterol and stearylamine to give a molar ratio of 7:2:1 (lecithin:cholesterol:stearylamine); and (3) phosphatidic acid and cholesterol to give a molar ratio of 7:2:1 (lecithin:phosphatidic acid:cholesterol).

7.6. SPLVs Containing Pilocarpine

The procedure of Section 7.1. was followed except that the antibiotic streptomycin was replaced with pilocarpine.

7.7. SPLVs Prepared With and Without BHT

Undistilled ether contains an anti-oxidant, 1 μg/ml butylhydroxytoluene (BHT), for storage purposes. The procedure described in Section 7.1. was following using undistilled ether as the solvent in order to incorporate BHT into the SPLV preparation.

In order to prepare SPLVs without incorporation of BHT, the procedure described in Section 7.1. was followed using distilled ether as the solvent.

8. EXAMPLE: SPLV MEDIATED DELIVERY IN VITRO

In the following example, SPLV mediated delivery of antibiotics to macrophages in culture was demonstrated.

Peritoneal macrophages were obtained by peritoneal lavage from C57BLK adult male mice and suspended in minimal essential medium (M.E.M.) pH 7.2 containing 10% heatinactivated fetal calf serum. Cells were suspended at a concentration of $1 \times 10^6$ cells per ml in 96-well tissue culture dishes. To cultures containing adherent peritoneal macrophages, were added B. canis at concentrations of $1 \times 10^6$ CFU (colony forming units) per ml. After 12 hours, bacteria not engulfed by peritoneal macrophages were removed by repeated washings with M.E.M. After washing of peritoneal macrophage cultures, they were divided into 5 groups, each containing 12 replicate cultures per group. Group 1, designated Controls, received no treatment. Group 2 received aqueous streptomycin sulfate at a concentration of 1 mg/ml. Group 3 received buffer-filled SPLVs. Group 4 received aqueous streptomycin sulfate (1 mg/ml) plus preformed buffer-filled SPLVs. Group 5 received SPLVs containing streptomycin sulfate (1 mg/ml). After 24 hours, supernatants were removed by repeated washings and peritoneal macrophages were disrupted by repeated freezing and thawing. Serial dilutions of disrupted macrophages were plated onto brucella agar and, after 4 days, surviving B. canis were determined by limiting dilution techniques. Results shown in Table VII indicate that SPLV-entrapped streptomycin was totally effective in killing and eliminating the intracellular B. canis infection in vitro.

The experiment was repeated with B. abortus exactly as described above except that peritoneal macrophages were obtained by peritoneal lavage from adult female albino guinea pigs. Results are also shown in Table VIII.

TABLE VIII

COLONY-FORMING UNITS OF INTRACELLULAR BRUCELLA ISOLATED AFTER TREATMENT OF INFECTED MACROPHAGES WITH SPLVS CONTAINING STREPTOMYCIN

| | *B. canis*[a] | *B. abortus*[b] |
|---|---|---|
| Controls | $2.6 \pm 1.13 \times 10^3$ | $3.1 \pm 0.81 \times 10^4$ |
| Buffer-filled SPLVs | $2.82 \pm 0.10 \times 10^3$ | $2.9 \pm 0.17 \times 10^4$ |
| Free Streptomycin[c] | $3.11 \pm 0.40 \times 10^3$ | $3.3 \pm 0.25 \times 10^4$ |
| Streptomycin Plus Buffer-filled SPLVs[c] | $2.76 \pm 0.20 \times 10^3$ | $2.8 \pm 0.42 \times 10^4$ |
| SPLV-Entrapped Streptomycin[c] | 0 | 0 |

[a]Colony forming units (CFU) of *B. canis* (mean + SD of 12 replicates) isolated from equal numbers of previously infected mouse (C57Blk) peritoneal macrophages.
[b]CFU of *B. abortus* (mean + SD of 12 replicates) isolated from equal numbers of previously infected guinea pig peritoneal macrophages.
[c]Concentration of streptomycin 1 mg/ml.

9. EXAMPLE: TREATMENT OF INTRACELLULAR INFECTIONS

The following examples demonstrate how SPLVs can be used in treating intracellular infections. The data presented demonstrates: (1) the effectiveness of using antibiotics encapsulated in SPLVs in the treatment of disease and (2) the greater efficiency which is obtained by administering multiple doses of the SPLV preparation. A comparison of MLVs to SPLVs as vehicles used in the protocols is described.

Brucellosis causes worldwide economic and public health problems. Brucellosis is caused by *Brucella spp.* It is adapted to many mammalian species, including man, domestic animals and a variety of wild animals. Six *Brucella spp.* cause brucellosis in animals; they are *B. abortus, B. canis, B. melitensis, B. neotomae, B. ovis* and *B. suis.* Both domestic and wild animals serve as reservoirs for potential spread of brucellosis to other animals and man.

Such infections cannot be cleared with antibiotics because the infectious organisms reside within the cells of the reticuloendothelial system and are highly resistant to bactericidal activities of antibiotics. The quantity of antibiotics required and the length of treatment results in either toxic effects on the animal or an unacceptably high concentration of the antibiotic in the tissues of the animal. The further difficulty in treating this disease is that the treatment has to be completely effective since any remaining infection will simply spread and the cycle commences once again. The economic impact of such diseases is demonstrated by the millions of dollars of valuable cattle which are lost each year due to spontaneous abortion. The only potential way to combat such infectious outbreaks is to quarantine and then slaughter the animals.

The examples which follow comprise incorporating an antibiotic into SPLVs, and then administrating the encapsulated active substance to the animals by inoculating the infected animals intraperitoneally.

9.1. EFFECT OF A SINGLE TREATMENT OF *B. CANIS* INFECTION USING SPLV-ENTRAPPED ANTIBIOTIC

In the following experiment, SPLVs were prepared by the emulsification process as described in Section 7. Eighty adult male Swiss mice were infected intraperitoneally (I.P.) with *B. canis* ATCC 23365 ($1\times10^7$ CFU) and divided into 8 groups of 10 mice each. Seven days post-inoculation with *B. canis*, groups were treated as follows: Group 1, designated Controls, received no treatment; Group 2 received buffer-filled SPLVs (0.2 ml I.P.); Group 3 received aqueous streptomycin sulfate (1 mg/kg body weight in a total administration of 0.2 ml I.P.); Group 4 received aqueous streptomycin sulfate (5 mg/kg body weight) in a total administration of 0.2 ml I.P.; Group 5 received aqueous streptomycin sulfate (10 mg/kg body weight) in a total administration of 0.2 ml I.P.; Group 6 received SPLVs containing streptomycin sulfate (1 mg/kg body weight) in a total administration of 0.2 ml I.P.; Group 7 received SPLVs containing streptomycin sulfate (5 mg/kg body weight) in a total administration of 0.2 ml I.P.; and Group 8 received SPLVs containing streptomycin sulfate (10 mg/kg body weight) in a total administration of 0.2 ml I.P.. On day 14 post-inoculation with *B. canis*, all animals were sacrificed and spleens were removed aseptically. Spleens were homogenized and serially diluted onto brucella agar to determine the number of surviving *B. canis* in spleens after treatment. Results after 4 days incubation are shown in Table IX.

TABLE IX

EFFECT OF A SINGLE TREATMENT[a] OF *B. CANIS* INFECTED MICE WITH VARIOUS CONCENTRATIONS OF FREE OR SPLV-ENTRAPPED STREPTOMYCIN

| | Colony-Forming Units *B. Canis* Per Spleen[b] | |
|---|---|---|
| | No Treatment | Buffer-Filled SPLVs |
| Control | $3.46 \times 10^6 \pm 2.7 \times 10^6$ | $4.1 \times 10^6 \pm 0.66 \times 10^6$ |
| Streptomycin Concentration (mg/kg body weight) | Free Streptomycin | SPLV-Entrapped Streptomycin |
| 1 | $1.5 \pm 0.45 \times 10^6$ | $1.01 \pm 0.25 \times 10^3$ |
| 5 | $2.12 \pm 1.71 \times 10^5$ | $1.52 \pm 0.131 \times 10^4$ |
| 10 | $9.66 \pm 3.68 \times 10^4$ | $1.32 \pm 1.00 \times 10^4$ |

[a]I.P. injection in total of 0.2 ml (sterile saline).
[b]Surviving *B. canis* was determined as the number of CFU isolated per spleen and is expressed as mean ± S.D. of 10 animals per experiment (triplicate experiments).

onstrate that in groups receiving aqueous streptomycin 7 and 10 days post-inoculation, very little reduction in surviving *B. canis* in spleens was observed. Only in groups receiving SPLV-entrapped streptomycin at a concentration of 10 mg/kg body weight administered on day 7 and 10 post-inoculation were all viable bacterial eliminated from spleens of infected animals.

In addition to the experiment described above, various tissues from *B. canis* infected mice after two treatments with SPLV-entrapped streptomycin were sampled as follows:

Thirty adult male Swiss mice were inoculated with *B. canis* ATCC 23365 ($1 \times 10^7$ CFU, I.P.). Seven days post-inoculation animals were divided into 3 groups of 10 mice each. Group 1, designated controls, received no treatment; Group 2 received (on days 7 and 10 post-inoculation) aqueous streptomycin sulfate (10 mg/kg body weight) in each administration of 0.2 m±), I.P.; Group 3 received (on days 7 and 10 post-inoculation) SPLVs containing streptomycin sulfate (10 mg/kg body weight) in each administration of 0.2 ml, I.P. On days 14 to 75 post-inoculation with *B. canis*, all animals were sacrificed and the following organs removed aseptically, homogenized and serially diluted onto brucella agar for isolation of *B. canis*: heart, lungs, spleen, liver, kidneys, testes. After 4 days incubation, results of surviving *B. canis* per organ are shown in FIG. 19.

Results of samplings of various tissues in *B. canis* infected mice after two treatment regimens with streptomycin presented in FIG. 19, demonstrated that in animals treated with SPLV-entrapped streptomycin, all tissues sampled from 14 to 75 days post-inoculation with *B. canis* were totally free of any viable *B. canis* organisms. In animals untreated or treated with aqueous streptomycin in concentrations and administration schedules identical to those receiving SPLV-entrapped streptomycin, viable *B. canis* organisms could be isolated in all tissues sampled from 14 to 75 days post-inoculation with *B. canis.*

In the following experiment, SPLVs were prepared by the monophasic solvent system method as described in Section 6.

Twenty adult female Swiss Webster mice were infected with *B. canis* ATCC 23365 ($5 \times 10^6$ colony forming units, CFU) intraperitoneally (I.P.) and divided into 2 groups of 10 mice each. Seven days and 10 days post-inoculation with *B. canis*, groups were treated as follows: Group 1, dsignated controls, received no treatment, Group 2 received SPLVs containing gentamicin (10 mg/kg body weight) in a total volume of 0.3 ml, I.P.

9.2. Effect of Multiple Treatment of B. Canis Infection Using SPLV-Entrapped Antibiotic In the following experiments, SPLVs were prepared by the emulsification process described in Section 7.

Eighty adult male Swiss mice were infected with *B. canis* ATCC 23365 ($1 \times 10^7$ CFU, I.P.) and divided into 8 groups of 10 mice each. Seven days and 10 days post-inoculation with *B. canis*, groups were treated as follows: Group 1, designated controls, received no treatment; Group 2 received buffer-filled SPLVs (0.2 ml, I.P.); Group 3 received aqueous streptomycin sulfate (1 mg/kg body weight) in a total administration of 0.2 m±, I.P.); Group 4 received aqueous streptomycin sulfate (5 mg/kg body weight) in a total administration of 0.2 m±, I.P.; Group 5 received aqueous streptomycin sulfate (10 mg/kg body weight) in a total administration of 0.2 ml, I.P.; Group 6 received SPLVs containing streptomycin sulfate (1 mg/kg body weight) in a total administration of 0.2 ml, I.P.; Group 7 received SPLVs containing streptomycin sulfate (5 mg/kg body weight) in a total administration of 0.2 ml, I.P.; and Group 8 received SPLVs containing streptomycin sulfate (10 mg/kg body weight) in a total administration of 0.2 ml, I.P. On day 14 post-inoculation with *B. canis*, all animals were sacrificed and spleens were removed aseptically. Spleens were homogenized and serially diluted onto brucella agar to determine the number of surviving *B. canis* in spleens after treatment. Results after 4 days incubation are shown in FIG. 18.

The results of various two-stage treatment regimens on *B. canis* infections *in vivo* presented in FIG. 18, dem- On day 17 post-inoculation with *B. canis*, all animals were sacrificed and spleens removed aseptically. Spleens were homogenized and serially diluted onto brucella agar to determine the number of surviving *B. canis* in spleens after treatment. Results after 3 day incubation are shown in Table X.

The results of the two-stage treatment regimens on *B. canis* infections *in vivo* presented in Table X, demonstrate that in groups receiving SPLV-entrapped gentamicin at a concentration of 10 mg/kg of body weight administered on days 7 and 10 post-inoculation all viable bacteria were eliminated from spleens of infected animals.

TABLE X

EFFECTIVENESS OF SPLVS CONTAINING GENTAMICIN ON KILLING OF *B. CANIS* IN VIVO AFTER TWO TREATMENTS[a]

| | Colony-Forming Units per Spleen[b] |
|---|---|
| Control | $2.20 \pm 0.26 \times 10^4$ |
| SPLVs[c] | 0 |

[a]Intraperitoneal injections, 10 mg/kg body weight, were spaced at 3 day intervals. Controls received no treatment.
[b]Surviving *B. canis* was determined as the number of CFU isolated per spleen and is expressed as the mean ± S.D. of 20 cultures.
[c]Egg phosphatidylcholine to gentamicin ratios were 100 mg lipid to 30 mg gentamicin.

9.3. Effectiveness of Treatments Using MLVs as Compared to SPLVs

In the following experiment, SPLVs were prepared by the emulsification process as described in Section 7. Fifteen adult male Swiss mice were inoculated with *B. canis* ATCC 23365 ($1 \times 10^7$ CFU, I.P.). Seven days post-inoculation animals were divided into 3 groups of 5 mice each. Group 1, designated Controls, received no treatment; Group 2 received (on days 7 and 10 post-inoculation) MLVs containing streptomycin sulfate (10 mg/kg body weight, I.P.). MLVs were prepared by conventional techniques using 100 mg egg phosphatidylcholine (EPC) and 2 ml of sterile HEPES containing streptomycin sulfate (100 mg/ml). The lipid to streptomycin sulfate ratio was 100 mg EPC to 28 mg streptomycin sulfate in the 2 ml final MLV suspension; Group 3 received (on days 7 and 10 post-inoculation) SPLVs containing streptomycin sulfate (10 mg/kg body weight, I.P.) prepared as described in Section 7.1. with the following modifications: 100 mg EPC were used, and 0.3 ml of HEPES containing 100 mg streptomycin sulfate. The lipid to streptomycin sulfate ratio in SPLVs was 100 mg EPC to 28 mg streptomycin sulfate in a 2 m±final suspension. On day 14 post-inoculation with *B. canis*, all animals were sacrificed and spleens were removed aseptically, homogenized and serially diluted onto brucella agar for isolation of *B. canis*. Results of surviving *B. canis* per organ after 4 days L-incubation are shown in Table XI.

TABLE XI

COMPARISON OF MLVS AND SPLVS CONTAINING STREPTOMYCIN SULFATE ON KILLING OF *B. CANIS* IN VIVO AFTER TWO TREATMENTS[a]

| | Colony-Forming Units *B. Canis* per Spleen[b] |
|---|---|
| Control | $2.7 \pm 1.0 \times 10^4$ |
| MLVs[c] | $1.8 \pm 0.4 \times 10^4$ |

TABLE XI-continued

COMPARISON OF MLVS AND SPLVS CONTAINING STREPTOMYCIN SULFATE ON KILLING OF *B. CANIS* IN VIVO AFTER TWO TREATMENTS[a]

| | Colony-Forming Units *B. Canis* per Spleen[b] |
|---|---|
| SPLVs[c] | 0 |

[a]Intraperitoneal injections, 10 mg/kg body weight, were spaced at 3 day intervals. Controls received no treatment.
[b]Surviving *B. canis* was determined as the number of CFU isolated per spleen and is expressed as the mean ± S.D. of 5 animals per group (duplicate determinations per animal).
[c]Egg phosphatidylcholine to streptomycin sulfate ratios were 100 mg lipid to 28 mg streptomycin sulfate.

9 .4. EFFECT OF VARIOUS SPLV-ENTRAPPED ANTIBIOTICS ON TREATMENT OF INFECTION

In the following experiment, SPLVs were prepared by the emulsification method as described in Section 7.

Fifty adult male Swiss mice were inoculated with *B. canis* ATCC 23365 ($1 \times 10^7$ CFU, I.P.). Seven days post-inoculation, animals were divided into 10 groups of 5 mice each. Group 1, designated controls, received no treatment; Group 2 received buffer-filled SPLVs (0.2 ml, I.P.) on days 7 and 10 post-inoculation; Groups 3, 4, 5 and 6 received aqueous injections (0.2 ml I.P.) of dihydrostreptomycin, gentamicin, kanamycin or streptomycin 10 mg/kg body weight, I.P. on days 7 and 10 post-inoculation (N.B. Each of these antibiotics have been shown to kill *B. canis* in vitro). Groups 7, 8, 9, and 10 received SPLVs containing dihydrostreptomycin, gentamicin, kanamycin, or streptomycin at 10 mg/kg body weight on days 7 and 10 postinoculation. On day 14 post-inoculation with *B. canis*, all animals were sacrificed and spleens were removed aseptically, homogenized and serially diluted onto brucella agar for at isolation of *B. canis*. Results of surviving *B. canis* per organ after 4 days incubation are as shown in Table XII.

The results from tests of various antibiotics on *B. canis* infected mice presented in Table XII demonstrate that antibiotics which are effective in killing *B. canis in vitro* (i.e., in suspension culture) are also only effective in killing *B. canis* infections *in vivo* when they are encapsulated within SPLVs. Animals receiving either aqueous antibiotics, buffer-filled SPLVs or no treatment were in no case cleared of surviving *B. canis* in isolated spleen tissues.

9.5. Treatment of Dogs Infected with B. Canis

In the following experiment, SPLVs were prepared by the emulsification process as described in Section 7. Adult female beagles were inoculated with *B. canis* ATCC 23365 ($1 \times 10^7$ CFU) orally and vaginally. Seven days post-inoculation dogs were divided into 3 groups. Group 1, designated control, received no treatment; Group 2 received (on days 7 and 10 post-inoculation) aqueous streptomycin sulfate at 10 mg/kg body weight (each administration was 5.0 ml, I.P.). Group 3 received (on days 7 and 10 post-inoculation) SPLVs containing streptomycin sulfate at 10 mg/kg body weight (each administration was 3.0 ml, I.P.).

TABLE XII

COMPARISON OF VARIOUS ANTIBIOTICS ON KILLING OF B. CANIS IN VIVO AFTER TWO TREATMENTS[a]

| | Colony-Forming Units B. Canis Per Spleen[b] | |
|---|---|---|
| | Aqueous Solutions | SPLV-Entrapped Antibiotic |
| Untreated Antibiotic[c] | $3.93 \pm 1.51 \times 10^6$ | $4.66 \pm 0.87 \times 10^6$ |
| Dihydro-streptomycin | $1.13 \pm 0.30 \times 10^5$ | 0 |
| Gentamicin | $7.06 \pm 2.53 \times 10^5$ | 0 |
| Kanamycin | $2.72 \pm 0.91 \times 10^5$ | 0 |
| Streptomycin | $1.01 \pm 0.17 \times 10^5$ | 0 |

[a]Intraperitoneal treatments. 10 mg/kg body weight, were spaced at 3 day intervals. Controls received no treatment.
[b]Surviving B. canis per organ was determined as the number of CFU isolated per spleen and expressed as the mean ± S.D. of 5 animals per groups (duplicate determinations per animal).
[c]Antibiotics effective in killing B. canis in suspension culture.

TABLE XIII

RESULTS OF CULTURES AND SEROLOGICAL TESTING IN B. CANIS INFECTED DOGS SUBJECTED TO A TWO TREATMENT ANTIBIOTIC REGIMEN[a]

| Days After Infection with B. Canis | Control | | | | Streptomycin[b] | | | | SPLV-Entrapped[c] Streptomycin | | | |
|---|---|---|---|---|---|---|---|---|---|---|---|---|
| | R | M | B | V | R | M | B | V | R | M | B | V |
| Pre-treatment | | | | | | | | | | | | |
| 0 | 0 | 0 | 0 | 0 | 0 | 0 | 0 | 0 | 0 | 0 | 0 | 0 |
| 2 | ND | ND | + | + | ND | ND | + | 0 | ND | ND | + | + |
| 4 | ND | ND | + | + | ND | ND | + | + | ND | ND | + | + |
| Post-treatment | | | | | | | | | | | | |
| 8 | 0 | 0 | 0 | + | 0 | 0 | + | 0 | 0 | 0 | 0 | 0 |
| 10 | 0 | 0 | 0 | + | 0 | 0 | 0 | + | 0 | 0 | 0 | 0 |
| 21 | 1.5 | 2 | + | + | 1 | 2 | + | + | 0 | 0 | 0 | 0 |

[a]R (rapid slide agglutination test) indicates the reciprocal of serum titer to B. canis antigen ($\times 10^2$); 0 = no detectable titer.
M (2-mercaptoethanol tube agglutination test) indicates the reciprocal of serum titer to B. canis antigen ($\times 10^2$); 0 = no detectable titer.
In B (blood culture) and V (vaginal culture) on brucella agar: + = detection of greater than or equal to 1 CFU; 0 = no colonies detected. Controls received no treatment.
[b]Streptomycin sulfate (aqueous) 10 mg/kg body weight, I.P.
[c]SPLVs containing streptomycin sulfate 10 mg/kg body weight, I.P.

Vaginal swabbings of dogs and heparinized blood samples were collected at regular intervals before, during, and at the termination of the study. These were cultured on brucella agar in order to isolate B. canis. Results are shown in Table XIII Serum samples were collected before, during, and at the termination of the study for determinations of serum antibody against B. canis. These results are also shown in Table XIII.

Twenty-one days post-inoculation with B. canis, all animals were euthanized. The following tissues were removed aseptically, homogenized and serially diluted onto brucella agar for isolation of B. canis: heparinized blood, vaginal exudate, lungs, spleen, synovial fluid, uterus, ovary, popliteal lymph nodes, salivary glands, tonsils, mediastinal lymph nodes, mesenteric lymph nodes, bone marrow, superficial cervical lymph nodes, and auxiliary lymph nodes. Results of surving B. canis per tissue after 4 days incubation are shown in Table XIV.

Results of culture and serologic tests of dogs infected with B. canis before, during, and after two-stage antibiotic administration are presented in Table XVI. All animals were serologically negative for previous exposure to B. canis as measured by negative serum titers, and were culture negative from blood cultures and cultures of vaginal swabbings. All animals were noted to be culture positive for both blood and vaginal cultures prior to treatments on days 7 and 10. Dogs treated with aqueous streptomycin or dogs receiving no treatment remained culture positive for blood and vaginal cultures during post-treatment periods prior to termination on day 21. Group 3, which received liposomes containing streptomycin, became culture negative one day after the first treatment and remained negative throughout post-treatment period.

TABLE XIV

RESULTS OF CULTURES FROM TISSUE SAMPLES IN B. CANIS INFECTED DOGS SUBJECTED TO A TWO TREATMENT ANTIBIOTIC REGIMEN[a]

| Tissue[b] | SPLVs Containing Streptomycin[c] | Streptomycin[d] | Control[e] |
|---|---|---|---|
| Whole blood | 0 | + | + |
| Vaginal swab | 0 | + | + |
| Lungs | 0 | + | + |
| Spleen | 0 | + | + |
| Synovial fluid | N.D. | 0 | 0 |
| Uterus | 0 | + | + |
| Ovary | 0 | + | + |
| Popliteal lymph nod | N.D. | + | + |
| Salivary gland | 0 | 0 | 0 |
| Tonsil | 0 | + | + |
| Mediastinal lymph node | 0 | N.D. | + |
| Mesenteric lymph node | N.D. | 0 | 0 |
| Bone marrow | 0 | + | + |
| Superficial cervical lymph node | N.D. | N.D. | + |
| Axillary lymph node | 0 | + | + |

[a]Animals treated on day 7 and 10 post-infection.
[b]Samples taken at necropsy were serially diluted on brucella agar; + = equal to or greater than 1 CFU; 0 = no colonies.
[c]SPLVs containing streptomycin sulfate, 10 mg/kg body weight I.P.
[d]Streptomycin sulfate (aqueous), 10 mg/kg body weight, I.P.
[e]Controls received no treatment.

Dogs which received no treatment or aqueous streptomycin developed detectable serum titers against B. canis antigens by day 21 post-inoculation, while those treated with SPLVs containing antibiotics on days 7 and 10 post-inoculation did not develop any detectable antibody to B. canis antigen.

Results from isolation of B. canis from infected dogs treated with two-stage antibiotic administration which are presented in Table XVII demonstrate that in dogs, only treatment with SPLVs containing streptomycin was effective in eliminating any viable B. canis in all tissues from all organ samples.

9.6. Treatment of B. Abortus in Guinea Pigs 7

In the following experiment, SPLVs were prepared by the emulsification method as described in Section 7.

Fifteen adult female guinea pigs were inoculated with *B. abortus* ATCC 23451 ($1 \times 10^7$ CFU, I.P.). Seven days post-inoculation animals were divided into 3 groups of 5 animals each. Group 1, designated Controls, received no treatment. Group 2 received aqueous streptomycin sulfate, I.P. injections (0.2 ml) at 10 mg/kg body weight on day 7 and 10 post-inoculation with *B. abortus*. Group 3 received SPLVs containing streptomycin sulfate I.P. injections (0.2 m±) at 10 mg/kg body weight on days 7 and 10 post-inoculation with *B. abortus*. On day 14 post-inoculation with *B. abortus*, all animals were sacrificed and spleens were removed, aseptically homogenized and serially diluted onto brucella agar for isolation of *B. abortus*. Results of surviving *B. abortus* per spleen after 4 days incubation, are shown in FIG. 20. Only SPLVs containing streptomycin were effective in eliminating *B. abortus* residing within guinea pig spleen. In animals receiving aqueous streptomycin or no treatment, viable *B. abortus* bacteria were be identified.

9.7. Treatment of B. Abortus Infection in Cows

In the following experiment, SPLVs were prepared by the emulsification process as described in Section 7.

Nine heavily infected animals were utilized in this experiment. *B. abortus* bacterial isolations from milk and vaginal swabbings became and remained negative for six weeks following treatment with SPLVs containing streptomycin. When infection reoccurred in these animals, bacterial isolations were found only in quadrants of the udder which were positive prior to treatment.

Nine cross-bred (Hereford-Jersey-Brangus), 22-month old, non-gravid, confirmed *B. abortus* culture-positive cows were used. At least 4 months prior to the initiation of the study, the animals were experimentally challenged *per conjunctivum* with $1 \times 10^7$ CFU of *B. abortus* Strain 2308 during mid-gestation, which resulted in abortion and/or *B. abortus* culture positive lacteal or uterine secretions and/or fetal tissues.

Cows were maintained in individual isolation stalls and separated into three groups. Treatment comprised a twodose regimen, spaced 3 days apart, as follows: (1) 3 cows were injected intraperitoneally with physiological saline. (2) 3 cows were injected intraperitoneally with aqueous antibiotic (streptomycin at 10 mg/kg body weight) plus preformed buffer-filled SPLVs. (3) 3 cows were injected intraperitoneally with SPLV-entrapped streptomycin (10 mg/kg body weight). The total volume per injection was 100 ml per animal.

During the first 2 months duplicate bacteriologic cultures of lacteal and uterine secretions were performed weekly providing secretions were obtainable. Then, all cows were euthanatized with an overdose of sodium pentabarbitol, and the following organs were collected in duplicate for bacteriologic cultures: (1) lymph nodes: left and right atlantal, left and right suprapharyngeal, left and right mandibular, left and right parotid, left and right prescapular, left and right prefemoral, left and right axillary, left and right popliteal, left and right internal iliac, left and right supramammary, left and right renal, bronchial, mediastinal, mesenteric, and hepatic; (2) glands: all four quarters of mammary gland, left and right adrenal glands and thymus (if present); (3) organs and other tissues: spleen, liver, left and right horn of uterus, cervix, vagina, kidney and tonsil.

After necropsy, all tissues were frozen and maintained at $-70°$ C. while in transport. Tissues were thawed, alcohol flamed, and aseptically trimmed prior to weighing. Once weights were recorded (0.2 to 1.0 grams), the tissue was homogenized in 1 ml of sterile saline and serially diluted with sterile saline to 1:10-10 of initial homogenate suspension. Aliquots (20 µl) of each dilution from serial suspensions were plated onto brucella agar and placed in 37° C. incubation. Duplicate determinations were performed for each tissue.

Plates were read daily and scored for bacterial growth. All colonies appearing prior to 3 days were isolated, passaged, and gram stained to determine identity. On days 5, 6 and 7 during incubation colonies with morphology, growth, and gram staining characteristics consistent with *B. abortus* were counted; the CFU per gram tissue was then determined. Representative colonies were repassaged for bacterial confirmation of *B. abortus*.

TABLE XV

RESULTS OF CULTURES FROM TISSUE SAMPLES OF *B. ABORTUS* INFECTED COWS

| Tissue | Untreated Control | SPLV-Entrapped Streptomycin | | |
|---|---|---|---|---|
| | | 1 | 2 | 3 |
| Adrenal gland L | 0 | 0 | 0 | 0 |
| Adrenal gland R | ++ | 0 | 0 | + |
| Atlantal LN R | ++ | + | 0 | + |
| Atlantal LN L | 0 | 0 | 0 | + |
| Axillary LN R | +++ | 0 | + | 0 |
| Axillary LN L | ++ | 0 | 0 | 0 |
| Bronchial LN | 0 | 0 | 0 | 0 |
| Cervix | 0 | 0 | 0 | 0 |
| Hepatic LN | ++++ | 0 | 0 | 0 |
| Horn of Uterus L | 0 | 0 | 0 | + |
| Horn of Uterus R | 0 | 0 | 0 | 0 |
| Int. Illiac LN R | ++ | 0 | 0 | 0 |
| Int. Illiac LN L | ++++ | 0 | + | 0 |
| Kidney | 0 | 0 | 0 | 0 |
| Liver | 0 | 0 | 0 | 0 |
| Lung | 0 | 0 | 0 | 0 |
| Mammary Gland LF | 0 | + | + | 0 |
| Mammary Gland LR | 0 | 0 | 0 | + |
| Mammary Gland RF | ++ | 0 | 0 | 0 |
| Mammary Gland RR | ++ | 0 | 0 | 0 |
| Mandibular LN R | +++ | 0 | 0 | 0 |
| Mandibular LN L | +++ | 0 | 0 | 0 |
| Mediastinal LN | ++ | 0 | + | 0 |
| Mesenteric LN | +++ | 0 | 0 | 0 |
| Parotid LN L | +++ | 0 | 0 | 0 |
| Parotid LN R | +++ | 0 | 0 | 0 |
| Popliteal LN L | + | 0 | 0 | 0 |
| Popliteal LN R | + | 0 | 0 | 0 |
| Prefemoral LN L | + | 0 | 0 | 0 |
| Prefemoral LN R | 0 | 0 | 0 | 0 |
| Prescapular LN L | 0 | 0 | 0 | + |
| Prescapular LN R | ++++ | 0 | 0 | 0 |
| Renal LN | 0 | 0 | 0 | 0 |
| Spleen | +++ | 0 | 0 | 0 |
| Supramammary LN L | +++ | + | 0 | 0 |
| Supramammary LN R | 0 | 0 | 0 | 0 |
| Suprapharangeal LN L | + | 0 | 0 | 0 |
| Suprapharangeal LN R | 0 | 0 | 0 | 0 |
| Thymus | 0 | 0 | 0 | 0 |
| Vagina | +++ | 0 | 0 | 0 |

0 No detectable bacteria by culture of 0.3-1 gm of tissue.
+ Less than 200 colonies/gm tissue.
++ More than 300 colonies/gm.
+++ More than 1,000 colonies/gm.
++++ More than 100,000 colonies/gm.

Bacteriologic isolations were done on all tissue samples and quantitation of bacteria per gram of tissue were calculated. The results from four animals—one placebo control and three animals treated with SPLV-entrapped streptomycin—are presented in Table XV.

10. EXAMPLE: TREATMENT OF SYSTEMIC INFECTIONS

The following examples demonstrate how SPLVs can be used in treating systemic infections.

10.1. Effect of Single Treatment of S. Typhimurium Infection Using SPLV-Entrapped Antibiotics The SPLVs used in the following experiment were prepared by the monophasic solvent system. SPLVs containing gentamicin, nafcillin or both were prepared as described in Section 6.2.

Ten adult female Swiss Webster mice were infected with *S. typhimurium* (O.D.$_{420}$ of 0.430 at approximately $5 \times 10^6$ CFU per mouse, I.P., and divided into 2 group each. One day post-inoculation with *S. typhimurium*, groups were treated as follows: Group 1, designated controls, received no treatment; Group 2 received SPLVs (prepared as described in section 6) containing nafcillin-gentamicin in a 1:1 ratio (100 mg/kg body weight) in a total volume of 0.3 ml I.P. (total dose 0.27 mg gentamicin per mouse in 0.3 ml and approximately 0.27 mg nafcillin per mouse based upon comparable encapsulation efficiencies for nafcillin and gentamicin). The animals were observed over 14 days for survival.

The results of the treatment are as follows: of the controls, after 2 days post-inoculation 2 mice survived, after 3 days no survivors were left; of Group 2, all animals survived until day 9 post-inoculation when one animal died, no other animal died during the 14 day period post-inoculation.

The results shown in Table XVI demonstrate the clinical effectiveness of the SPLV preparations. There were no survivors in both the control group and the groups treated with unentrapped antibiotics. However, 100% of the infected mice treated with gentamicin and nafcillin entrapped in SPLVs survived.

TABLE XVI

EFFECT OF A SINGLE TREATMENT OF
*S. TYPHIMURIUM* INFECTED MICE WITH
FREE OR SPLV-ENTRAPPED ANTIBIOTIC

| | Surviving Animals Group$^a$ | | |
|---|---|---|---|
| Day | 1 | 2 | 3 |
| 0 (infection) | 10 | 10 | 10 |
| 1 (treatment) | 10 | 10 | 10 |
| 2 | 3 | 6 | 10 |
| 3 | 2 | 5 | 10 |
| 4 | 0 | 1 | 10 |
| 5 | 0 | 1 | 10 |
| 6 | 0 | 0 | 10 |
| 7 | 0 | 0 | 10 |
| 8 | 0 | 0 | 10 |
| 9 | 0 | 0 | 10 |
| 14 | 0 | 0 | 10 |

$^a$Thirty mice divided into 3 groups were infected with *S. typhimurium*. The groups were treated as follows: (1) control; (2) nafcillin/gentamicin; (3) SPLVs containing nafcillin/gentamicin.

10.2. Effect of Multiple Treatment of S. Typhimurium Infection Using SPLV-Entrapped Antibiotics The SPLVs used in the following experiment were prepared by the monophasic solvent system method. SPLVs containing chloramphenicol were prepared as described in Section 6.4.

Twenty adult female Swiss Webster mice were infected with *S. typhimurium* (O.D.$_{420}$ of 0.430 at approximately $5.5 \times 10^6$, I.P., and divided into 2 groups of 10 mice each. One day post-infection and seven days post-infection groups were treated as follows: Group 1, designated controls, received no treatment; Group 2 received SPLVs containing chloramphenicol (100 mg/kg body weight) in a total volume of 0.1 ml I.P. The animals were observed over the following 14 day period for survival.

The results shown in Table XVII indicate that 90% of the infected animals treated with SPLV-entrapped chloramphenicol survived whereas none of the untreated animals survived.

These results demonstrate the therapeutic effectiveness of treatment of systemic infections with antibiotic-entrapped SPLVs.

TABLE XVII

EFFECT OF MULTIPLE TREATMENT MICE
INFECTED WITH *S. TYPHIMURIUM*

| | Surviving Animals | | |
|---|---|---|---|
| PAI Day | Controls | Free Chloramphenicol | SPLV/ Chloramphenicol |
| 0 (infection) | 10 | 10 | 10 |
| 1 (treatment) | 10 | 10 | 10 |
| 2 | 3 | 9 | 10 |
| 3 | 3 | 6 | 10 |
| 4 | 0 | 4 | 10 |
| 5 | 0 | 4 | 10 |
| 6 | 0 | 1 | 10 |
| 7 (treatment) | 0 | 0 | 9 |
| 14 | 0 | 0 | 9 |

10.3. Enhancement of Antibacterial Activity in Treating Salmonella Typhimurium Infections Using SPLVs Containing Gentamicin and Nafcillin In the following example, the antibacterial activity of various preparations of the aminoglycoside, gentamicin, and the pencillinase-resistant penicillin, nafcillin, are compared. The results demonstrate that of the preparations tested, treatment of lethal infections of *Salmonella typhimurium* (an intracellular infection) in mice is most effective using an SPLV preparation in which both gentamicin and nafcillin are incorporated into one SPLV preparation. SPLVs containing either gentamicin or nafcilin or both were prepared by the emulsification method as described in Sections 7.2 and 7.3

One hundred twenty-five mice were infected by intraperitoneal (I.P.) inoculation of a lethal dose (i.e., $3 \times 10^6$ colony forming units, CFU) of Salmonella typhimurium in order to establish septicemia. Twenty-four hours after inoculation the mice were divided into 8 groups of mice and each was treated as follows: Group 1 (controls) received no treatment; Group 2 received aqueous nafcillin (100 mg/kg body weight, I.P.); Group 3 received aqueous gentamicin (100 mg/kg body weight, I.P.); Group 4 received a single preparation containing both aqueous gentamicin (50 mg/kg body weight, I.P.) and nafcillin (50 mg/kg body weight, I.P.); Group 5 received SPLVs containing nafcillin (100 mg/kg body weight, I.P.); Group 6 received SPLVs containing gentamicin (100 mg antibiotic/kg body weight); Group 7 received a mixture of two SPLV preparations, one containing gentamicin (50 mg/kg body weight, I.P.) and the other SPLV preparation containing nafcillin (50 mg/kg body weight, I.P.); and Group 8 received one SPLV preparation containing both gentamicin (50 mg/kg body weight, I.P.) and nafcillin (50 mg/kg body weight, I.P.). Results are shown in Table XVIII.

The results shown in Table XVIII clearly indicate that the SPLVs containing both gentamicin and nafcillin were most effective in preventing mortality due to infection. In fact, the administration of the SPLV preparation containing both gentamicin and nafcillin was not only more effective in preventing mortality than was the administration of both drugs in an aqueous solution, but surprisingly treatment with the SPLV preparation containing both gentamicin and nafcillin was more effective in preventing mortality than was the simultaneous treatment with two populations of SPLVs, one containing gentamicin and the other containing nafcillin.

containing nafcillin were suspended to a total volume of 1 ml using physiological saline. A 0.5 ml aliquot of this suspension was resuspended to a final volume of 1 ml using physiological saline to which 20 mg gentamicin was added (SPLV/NAF in gentamicin, aq.); (d) SPLVs containing gentamicin were suspended to a total volume of 1 ml. A 0.5 ml aliquot of this suspension was resuspended to a final volume of 1 ml using physiological saline to which 20 mg nafcillin was added (SPLV/GENT in nafcillin, aq.); (e) the remaining 0.5 ml aliquot of SPLVs containing nafcillin in physiologic

TABLE XVIII

ENHANCED EFFECT OF SPLV-ENTRAPPED GENTAMICIN AND NAFCILLIN

| GROUP[a] | SURVIVAL DAYS ATER INFECTION DAYS POST TREATMENT | | | | | | | | | % SURVIVAL |
|---|---|---|---|---|---|---|---|---|---|---|
| | 1 | 2 | 3 | 4 | 5 | 6 | 7 | 8 | 14 | |
| GROUP 1 CONTROL (untreated) | | | 4/25 | 0/25 | 0/25 | 0/25 | 0/25 | 0/25 | 0/25 | 0% |
| GROUP 2 NAFCILLIN (aq.) | | | 0/15 | 0/15 | 0/15 | 0/15 | 0/15 | 0/15 | 0/15 | 0% |
| GROUP 3 GENTAMICIN (aq.) | 2/15[c] | 0/15 | 0/15 | 0/15 | 0/15 | 0/15 | 0/15 | 0/15 | 0/15 | 0% |
| GROUP 4 GENT/NAF (aq.) | | 9/10 | 5/10 | 1/10 | 0/10 | 0/10 | 0/10 | 0/10 | 0/10 | 0% |
| GROUP 5 SPLV/ NAFCILLIN | | | | 1/15 | 1/15 | 1/15 | 1/15 | 0/15 | 0/15 | 0% |
| GROUP 6 SPLV/ GENTAMICIN | | | | 1/15 | 1/15 | 1/15 | 1/15 | 0/15 | 0/15 | 0% |
| GROUP 7 SPLV/ NAFCILLIN AND SPLV/ GENTAMICIN | | | | 1/15 | 1/15 | 1/15 | 1/15 | 0/15 | 0/15 | 0% |
| GROUP 8 SPLV/ GENT-NAF | | | | 15/15 | 15/15 | 15/15 | 15/15 | 14/15 | 14/15 | 93% |

[a]Each group of mice received a total of 100 mg antibiotic/kg body weight (except for the control group which received no treatment) 24 hours after infection with a lethal dose of S typhimur (3 × 10⁶ CFU, I.P.).
[b]Survival is expressed as the number of mice alive divided by the total number of mice in the group.
[c]These mice died immediately after injection of gentamicin due to acute toxicity of the gentamicin.

10.4. Enhancement of Antibacterial Activity in Treating Salmonellosis Using SPLVs Containing Gentamicin and Nafcillin In this example, the antibacterial activity and clinical effectiveness of SPLVs containing both gentamicin and nafcillin are compared to a number of other preparations. The results indicate that of the preparations tested, treatment of *Salmonella typhimurium* is most effective when using an SPLV preparation in which gentamicin and nafcillin are both incorporated into one SPLV preparation.

SPLVs containing no drug and SPLVs containing either gentamicin or nafcillin, were prepared as by the emulsification method described in Section 7.2 using 200 mg EPC and 200 mg of drug. SPLVs containing both gentamicin and nafcillin were prepared as described in Section 7.3 using 200 mg EPC and 200 mg of each drug.

Each SPLV preparation was washed four times and resuspended in the following solutions: (a) SPLVs containing no drug were suspended to a total volume of 2 m±using physiological saline; (b) SPLVs containing both nafcillin and gentamicin (SPLV/NAF-GENT) in one liposome preparation were suspended to a total volume of 2 ml using physiological saline; (c) SPLVs saline (see (c) above) was added to a 0.5 ml aliquot of SPLVs containing gentamicin in physiologic saline (SPLV/NAF and SPLV/GENT). The resuspended SPLV preparations had the following compositions per 0.1 ml aliquot: (a) SPLVs = 20 mg EPC; (b) SPLV/NAF-GENT = 20 mg EPC, 2 mg nafcillin 2 mg gentamicin; (c) SPLV/NAF in gentamicin, aq. = 20 mg EPC, 2 mg nafcillin, 2 mg gentamicin; (d) SPLV/GENT in nafcillin, aq. = 20 mg EPC, 2 mg gentamicin, 2 mg nafcillin; and (e) SPLV/NAF and SPLV/GENT = 40 mg EPC, 2 mg nafcillin, 2 mg gentamicin.

Hilltop mice (20-30 mg each) were infected with *Salmonella typhimurium* by intraperitoneal injection of 0.3 ml of a culture of *S. typhimurium* in BHI broth (Brain Heart Infusion Media, BBL Microbiological Systems, Cockeysville, Md.) grown to an O.D.$_{420}$ of about 0.18.

Twenty seven hours after infection with *S. typhimurium* the mice were divided into 7 groups and each group was treated by inoculation of 0.1 ml (either I.P. or I.V., intravenous) as follows: Group 1 (controls) were untreated; Group 2 received SPLVs containing no drug (I.V.); Group 3 received SPLV/GENT in nafcillin, aq. (100 mg of each antibiotic/kg body weight, I.V.); Group 4 received SPLV/NAF in gentamicin, aq. (100 mg of each antiobiotic/kg body weight, I.V.); Group 5 received a mixture of two liposome populations, SPLV/NAF and SPLV/GENT (100 mg of each antibiotic/kg body weight, I.V.); Group 6 received SPLV/NAF-GENT (100 mg of each antiobiotic/kg body weight, I.V.); and Group 7 received SPLV/NAF-GENT (100 mg of each antibiotic per kg body weight, I.P.). Results are shown in Table XIX.

*typhimurium* is most effective when using an SPLV preparation in which gentamicin and nafcillin are incorporated into one liposome preparation. SPLVs containing either gentamicin or nafcillin or both were prepared by the monophasic solvent system process described in Sections 6.2 and 6.3.

Sixty-five mice were infected by intraperitoneal (I.P.) inoculation of a lethal dose (i.e., $5 \times 10^6$ CFU) of *S. typhimurium* in order to establish septicemia. Twenty-four hours after inoculation the mice were divided into

TABLE XIX

EFFECT ON SPLV ENTRAPPED GENTAMICIN AND NAFCILLIN ON *SALMONELLA TYPHIMURIUM* INFECTION IN MICE

| GROUP | SURVIVAL DAYS ATER TREATMENT | | | | | | | | | % Survival |
|---|---|---|---|---|---|---|---|---|---|---|
| | 1-3 | 4-5 | 6 | 7 | 8 | 9 | 10 | 11-12 | 13 | |
| GROUP 1 CONTROL (untreated) | 5/5 | 3/5 | 2/5 | 1/5 | 1/5 | 1/5 | 1/5 | 0/5 | 0/5 | 0% |
| GROUP 2 SPLVS (I.V.) | 5/5 | 3/5 | 3/5 | 1/5 | 0/5 | 0/5 | 0/5 | 0/5 | 0/5 | 0% |
| GROUP 3 SPLV/GENT IN NAFCILLIN aq. (I.V.) | 5/5 | 3/5 | 3/5 | 3/5 | 2/5 | 2/5 | 2/5 | 1/5 | 1/5 | 20% |
| GROUP 4 SPLV/NAF IN GENTAMICIN aq. (I.V.) | 5/5 | 4/5 | 4/5 | 0/5 | 0/5 | 0/5 | 0/5 | 0/5 | 0/5 | 0% |
| GROUP 5 SPLV/NAF AND SPLV/GENT (I.V.) | 5/5 | 4/5 | 4/5 | 3/5 | 3/5 | 3/5 | 1/5 | 1/5 | 0/5 | 0% |
| GROUP 6 SPLV/ NAF-GENT (I.V.) | 5/5 | 5/5 | 5/5 | 5/5 | 5/5 | 4/5 | 4/5 | 4/5 | 4/5 | 80% |
| GROUP 7 SPLV/ NAF-GENT (I.P.) | 5/5 | 5/5 | 4/5 | 4/5 | 4/5 | 3/5 | 3/5 | 3/5 | 3/5 | 60% |

These results demonstrate the increased effectiveness of the combination of nafcillin and gentamicin entrapped in one SPLV preparation in the treatment of *S. typhimurium* infection in vivo whether administered intravenously or intraperitoneally.

10.5. Enhancement of Antibacterial Activity in Treating Salmonella Typhimurium Infections Using SPLVs Containing Gentamicin and Nafcillin In this example, the antibacterial activity and clinical effectiveness of various preparations of the antibiotics gentamicin and nafcillin are compared. The results indicate that of the preparations tested, treatment of *S.*

3 groups and treated as follows: Group 1 (controls) received no treatment; Group 2 received a single preparation containing both aqueous gentamicin (100 mg/kg body weight) and aqueous nafcillin (100 mg/kg body weight, I.P.); Group 3 received one SPLV preparation containing both gentamicin (100 mg/kg body weight, I.P.) and nafcillin (50 mg/kg body weight, I.P.). Results are shown in Table XX.

Results shown in Table XX clearly demonstrate that the SPLVs containing gentamicin and nafcillin coencapsulated were most effective in preventing mortality due to infection.

TABLE XX

EFFECT OF SPLV-ENTRAPPED GENTAMICIN AND NAFCILLIN

| GROUP[a] | SURVIVAL[b] DAYS AFTER INFECTION | | | | | | | | % SURVIVAL |
|---|---|---|---|---|---|---|---|---|---|
| | 1-2 | 3 | 4 | 5 | 6 | 7-10 | 11-12 | 13-15 | |
| GROUP 1 CONTROL (untreated) | 20/20 | 5/20 | 2/20 | 0/20 | 0/20 | 0/20 | 0/20 | 0/20 | 0% |
| GROUP 2 GENT/NAF (aq.) | 20/20 | 15/20 | 10/20 | 6/20 | 1/20 | 0/20 | 0/20 | 0/20 | 0% |
| GROUP 3 SPLV/ | 25/25 | 25/25 | 25/25 | 25/25 | 25/25 | 25/25 | 24/25 | 23/25 | 92% |

TABLE XX-continued

EFFECT OF SPLV-ENTRAPPED GENTAMICIN AND NAFCILLIN

| GROUP[a] | SURVIVAL[b] DAYS AFTER INFECTION | | | | | | | % SURVIVAL |
|---|---|---|---|---|---|---|---|---|
| | 1-2 | 3 | 4 | 5 | 6 | 7-10 | 11-12 | 13-15 | |
| GENT-NAF | | | | | | | | | |

[a]Each animal received a total of 100 mg antibiotic/kg body weight (except for the control group which received no treatment) 24 hours after infection with a lethal dose of *typhimurium* (5 × 10⁶ CFU, I.P.).
[b]Survival is expressed as the number of mice alive divided by the total number of mice in the group.

11. EXAMPLE: TREATMENT OF OCULAR AFFLICTIONS

Bacterial and like infections as well as many other afflictions of the eye cause worldwide economic and public health problems, leading, if untreated or improperly treated, to loss of sight and possible death due to septicemia. Bacterial infections of the eye in animals and man have been reported to be caused by a variety of bacteria including but not limited to: *Clostridium spp., Corynebacterium spp., Leptospira spp., Moraxella spp., Mycobacterium spp., Neisseria spp., Propionibacterium spp., Proteus spp., Pseudomonas spp., Serratia spps., E. Coli spp., Staphylococcus spp., Streptococcus spp.* and bacteria-like organisms including *Mycoplasma spp.* and *Rickettsia spp.* Both animals and man serve as reservoirs for potential spread of infectious bacteria to each other.

Such bacterial infections cannot be treated with antibiotics without lengthy and cumbersome treatment schedules resulting in either frequent treatments, as rapid as every twenty minutes in humans with some infections, or unacceptably high concentrations of the antibiotic in the tissues. Current treatment methods are difficult for many other reasons. The infectious organism in the surface tissues of the eye in some cases are highly resistant to bactericidal activities of antibiotics, and topical administration of antibiotics can result in rapid clearing of the drug from the eye socket yielding varying contact times. As a general rule, treatment of eye infections has to be completely effective since any remaining infection will simply reinfect through lacrimal secretions and the cycle commences once again. Further, in many cases drug concentrations needed to eliminate the infection can cause impairment of vision and in certain cases can result in total blindness. The economic impact of such diseases in domestic animals is demonstrated by the millions of dollars which are lost each year since the only potential way to combat such infectious diseases is sustained therapy and quarantine.

The following experiments evaluate the effectiveness of treatments using free antibiotic in glycerine as compared to antibiotic entrapped in SPLVs for *M. bovis* infections of the eye.

*M. bovis* causes infectious keratoconjunctivitis (pink-eye) in cattle. This

TABLE XXI-continued

RESULTS OF TREATMENT OF INFECTIOUS KERATOCONJUNCTIVITIS
RESULTING FROM OCULAR INFECTIONS OF M. BOVIS IN MICE

| | M. Bovis | | | | | | | | | | Cultures[a] | |
|---|---|---|---|---|---|---|---|---|---|---|---|---|
| | Number of Mice Per Group of 20 | | | | | | | | | | | |
| | Pre-Treatment Corneal Opacity[b] | | | | | Post-Treatment[b] Corneal Opacity[b] | | | | | Days Post-Treatment | |
| | 0 | 1 | 2 | 3 | 4 | 0 | 1 | 2 | 3 | 4 | 3 | 5 |
| Buffer-filled SPLVs plus free Streptomycin[c] | 17 | 2 | 1 | 0 | 0 | 18 | 1 | 1 | 0 | 0 | 2/5 | 3/5 |
| SPLVs-Entrapped Streptomycin[c] | 17 | 3 | 0 | 0 | 0 | 20 | 0 | 0 | 0 | 0 | 0/5 | 0/5 |
| UV-Radiated Mice | | | | | | | | | | | | |
| Controls | 1 | 1 | 5 | 9 | 4 | 10 | 3 | 1 | 2 | 4 | 5/5 | 5/5 |
| Free Streptomycin[c] | 0 | 4 | 9 | 7 | 0 | 14 | 3 | 2 | 1 | 0 | 3/5 | 4/5 |
| Buffer-filled SPLVs plus free Streptomycin[c] | 0 | 3 | 5 | 10 | 2 | 11 | 2 | 4 | 3 | 0 | 3/5 | 3/5 |
| SPLVs-Entrapped Streptomycin[c] | 0 | 1 | 5 | 11 | 3 | 19 | 1 | 0 | 0 | 0 | 0/5 | 0/5 |

[a]Culture of eyes positive for presence of M. bovis. determined by fluorescent antibody staining.
[b]Scoring of normal cornea: 1 = loss of normal luster; 2 = small foci of opacity; 3 = partial opacity of cornea; 4 = total opacity of cornea.
[c]Total administration 10 μl (1.0 mg streptomycin per eye).

11.2. TREATMENT OF RABBIT CONJUNCTIVA USING SPLV-ENTRAPPED ANTIBIOTIC

M. bovis, ATCC strain 10900, were diluted to a concentration of $1 \times 10^7$ cells per ml in sterile saline (0.085% NaCl). Aliquots (0.1 ml) of bacterial suspensions were inoculated topically into the eyes of ten adult female rabbits. Samples for cultures were taken daily by swabbing the conjunctivae and plated onto blood agar plates for isolation of M. bovis. Three days post-inoculation, rabbits were divided into 3 groups: 2 animals (controls) received no treatment; 4 animals received streptomycin in sterile saline (concentration 10 mg/kg body weight); and 4 animals received SPLV-entrapped streptomycin in a sterile saline solution (concentration 10 mg streptomycin/kg body weight). All solutions were administered topically into each eye. After 24 hours, the swabbing of conjunctivae of all rabbits was resumed and continued daily for seven days. The results of isolation for M. bovis on blood agar plates are shown in Table XXII.

TABLE XXII

RESULTS OF ISOLATION FROM RABBIT
CONJUNCTIVAE AFTER TOPICALLY INFECTING
WITH M. BOVIS AND TREATING WITH
AQUEOUS OR SPLV-ENCAPSULATED STREPTOMYCIN

| Group | Animal Number | M. bovis Cultures[a] Days Post-Infection | | | | | | |
|---|---|---|---|---|---|---|---|---|
| | | Pre-Treatment[b] | | Post-Treatment[c] | | | | |
| | | 1 | 2 | 3 | 4 | 5 | 6 | 7 |
| Control | 1 | 0 | + | + | + | + | + | + |
| | 2 | 0 | + | + | + | + | + | + |
| Streptomycin[d] | 1 | 0 | + | + | + | + | + | + |
| | 2 | 0 | 0 | + | + | + | + | + |
| | 3 | 0 | + | + | + | + | + | + |
| | 4 | 0 | + | + | + | + | + | + |
| SPLV-Entrapped Streptomycin[e] | 1 | 0 | 0 | + | 0 | 0 | 0 | 0 |
| | 2 | 0 | + | + | 0 | 0 | 0 | 0 |
| | 3 | 0 | + | + | 0 | 0 | 0 | 0 |
| | 4 | 0 | + | + | 0 | 0 | 0 | 0 |

[a]Cultures scored for presence of M. bovis colonies on blood agar plates after 24 hours at 37° C. Plus (+) represents greater than or equal to 1 CFU M. bovis per isolate; 0 represents no detectable colonies.
[b]All animals inoculated with $1 \times 10^6$ CFU M. bovis topically in each eye.
[c]Animals treated with 0.1 ml solution topically in each eye.
[d]Streptomycin (10 mg/kg body weight) in sterile saline solution.
[e]SPLV-entrapped streptomycin (10 mg/kg body weight) in sterile saline solution.

11.3. Treatment of Keratoconjunctivitis Resulting from Subcutaneous Infections

*M. bovis*, ATCC strain 10900, were diluted to a concentration of $1\times10^7$ cells per ml in sterile saline. Aliquots (0.1 ml) of bacterial suspensions were inoculated into the eyes of adult rabbits which had been previously infected as described in Section 9.2. and were not treated with SPLVs. The right eyes of all nine rabbits were inoculated with 0.1 ml of *M. bovis* subcutaneously into conjunctival tissue and in the left eyes of all rabbits were inoculated with 0.1 ml of *M. bovis* topically. Cultures were taken daily from conjunctivae of both eyes from all rabbits and plated onto blood agar plates for isolation of *M. bovis*. Three days post-inoculation, rabbits were divided into 3 groups: 2 animals received no treatment; 3 animals received streptomycin in a standard ophthalmic glycerin suspension (concentration of streptomycin 10mg/kg body weight); and 4 animals received a saline suspension of SPLV-entrapped streptomycin (10 mg of streptomycin sulfate per kg of body weight). The suspension or solution was administered topically (0.1 ml) into each eye. After 24 hours and on each of the next five days, conjunctival swabbings were taken from all rabbits. The results of isolation for *M. bovis* on blood agar plates are shown in Table XXIII. Necropsies were performed on all animals at the termination of experiments and conjunctivae were removed from all animals. These were scored for vascularization, and were minced, homogenized and plated onto blood agar plates for isolation of *M. bovis*. Results are shown in Table XXIV.

TABLE XXIII
RESULTS OF ISOLATION FROM RABBIT CONJUNCTIVAE AFTER INOCULATION OF *M. BOVIS* INTO CONJUNCTIVAL MEMBRANES AND TREATMENT WITH STREPTOMYCIN IN OPHTHALMIC GLYCERINE SOLUTION OR SPLV-ENCAPSULATED STREPTOMYCIN IN SALINE

| | | *M. bovis* Cultures[a] Days Post Infection[c] | | | | |
|---|---|---|---|---|---|---|
| | Animal | Pre-treatment | | Post-Treatment | | |
| Group | Number[b] | 1 | 2 | 3 | 4 | 5 |
| Control | 1 | + | + | + | + | + |
| | 2 | + | + | + | + | + |
| Streptomycin | 1 | + | + | + | + | + |
| in Glycerne | 2 | + | + | + | + | + |
| solution[d] | 3 | + | + | + | + | + |
| SPLV- | 1 | + | + | 0 | 0 | 0 |
| Encapsulated | 2 | + | + | 0 | 0 | 0 |
| Streptomycin[e] | 3 | + | + | 0 | 0 | 0 |
| | 4 | + | + | 0 | 0 | 0 |

[a]Cultures scored for presence of *M. bovis* colonies on blood agar plates after 24 hours at 37° C. Plus (+) represents greater than or equal to 1 CFU *M. bovis* per isolate; 0 represents no detectable colonies.
[b]All animals were inoculated with $1 \times 10^6$ CFU *M. bovis* topically in both eyes: $1 \times 10^6$ CFU *M. bovis* was injected into conjunctival membranes, in right eyes; and $1 \times 10^0$ CFU *M. bovis* was applied topically in left eyes.
[c]Animals treated with 0.1 ml solution topically in each eye.
[d]Animals treated topically in each eye with streptomycin (10 mg/kg body weight) in ophthalmic glycerine base.
[e]Animals treated topically in each eye with SPLV-encapsulated streptomycin (10 mg/kg body weight) in sterile saline solution.

TABLE XXIV
RESULTS FROM NECROPSY OF THE ORBIT AND ASSOCIATED TISSUES FROM RABBITS AFTER INOCULATION WITH *M. BOVIS* INTO CONJUNCTIVAL TISSUES AND TREATMENT WITH EITHER STREPTOMYCIN IN OPHTHALMIC GLYCERINE SOLUTION OR SPLV-ENCAPSULATED STREPTOMYCIN IN STERILE SALINE[a]

| | Isolation of *M. bovis* Cultures | Vascularization of Right Eye[b] |
|---|---|---|
| Control A | + | 2+ |
| B | + | 2+ |
| Streptomycin in Glycerine Solution | | |
| A | + | 2+ |
| B | + | 1+ |
| C | + | 2+ |
| D | + | 2+ |
| SPLV-encapsulated Streptomycin | | |
| A | 0 | 0 |
| B | 0 | 0 |
| C | 0 | 0 |
| D | 0 | 0 |

[a]Legends are same as Table XXIII, performed on day 5, post infection.
[b]Vascularization scored as follows: 0 = vessels normal; 1 = some vessels definitely dilated and infiltrated by minor vessels; 2 = diffuse red with individual vessels not easily discernible; 3 = diffuse beefy red, vascular leakage and effusion of blood into conjunctivae.

11.4. Evaluation of the Effectiveness of SPLVs as Compared to Liposome Preparations in the Treatment of Ocular Infections

*M. bovis* (ATCC strain 10900) were diluted to a concentration of $1 \times 10^7$ cells per ml in sterile saline. Aliquots (0.1 ml) of bacterial suspensions were inoculated subcutaneously into the conjunctival tissues of both eyes in adult rabbits. Swabbings were taken daily from conjunctivae of both eyes from all rabbits and plated onto blood agar plates for isolation of *M. bovis*. Five days post-inoculation, rabbits were divided into 6 groups: 2 animals received no treatment (controls); 3 animals received a suspension of SPLV-encapsulated streptomycin (10mg of streptomycin sulfate per kg of body weight) which when diluted 1:100 had an $O.D._{480}$ (optical density at 480 nm) equal to 0.928; 3 animals received a suspension of SPLV-encapsulated streptomycin (10 mg of streptomycin sulfate per kg of body weight) which when diluted 1:100 had an $O.D._{480}$ equal to 0.449; 3 animals received a suspension of SPLV-encapsulated streptomycin (10 mg streptomycin sulfate per kg of body weight) which when diluted 1:100 had an $O.D._{480}$ equal to 0.242; 3 animals received a suspension of SPLV-encapsulated streptomycin (10 mg streptomycin sulfate per kg body weight) which when diluted 1:100 had an $O.D._{480}$ equal to 0.119; and 2 animals received a suspension of multilamellar vesicles (MLVs) containing streptomycin (10 mg streptomycin sulfate per kg of body weight) with an $O.D._{480}$ of a 1:100 dilution equal to 0.940. MLVS were made by the process of Fountain et al. Curr. Micro. 6:373 (1981) by adding streptomycin sulfate to the dried lipid film which was then vortexed, and allowed to swell for two hours; the non-entrapped streptomycin was removed by repeated centrifugation.

TABLE XXV

ISOLATION OF *M. BOVIS* FROM INFECTED RABBIT CONJUNCTIVAE AFTER TREATMENT WITH DILUTIONS OF SPLV-ENCAPSULATED STREPTOMYCIN IN SALINE OR MLV-ENCAPSULATED STREPTOMYCIN IN SALINE

| | | Isolation of *M. bovis*[a] Days Post-Infection Pre-Treatment Post-Treatment | | | | | | | | | | | | | |
|---|---|---|---|---|---|---|---|---|---|---|---|---|---|---|---|
| Group | Animal Number | 1 | 2 | 3 | 4 | 5 | 6 | 7 | 8 | 9 | 10 | 11 | 12 | 13 | 14 |
| Control | 1 | + | + | + | + | + | + | + | + | + | + | + | + | + | + |
| | 2 | + | + | + | + | + | + | + | + | + | + | + | + | + | + |
| MLV- | | | | | | | | | | | | | | | |
| encapsulated | 1 | + | + | + | + | + | + | + | 0 | 0 | + | + | + | 0 | + |
| Streptomycin | 2 | + | + | + | + | + | + | 0 | + | + | 0 | 0 | + | + | 0 |
| SPLV- | | | | | | | | | | | | | | | |
| encapsulated | 1 | + | + | + | + | + | 0 | 0 | 0 | 0 | 0 | 0 | 0 | 0 | 0 |
| Streptomycin | 2 | + | + | + | + | + | 0 | 0 | 0 | 0 | 0 | 0 | 0 | 0 | 0 |
| (undiluted) | 3 | + | + | + | + | + | 0 | 0 | 0 | 0 | 0 | 0 | 0 | 0 | 0 |
| SPLV- | | | | | | | | | | | | | | | |
| encapsulated | 1 | + | + | + | + | + | + | 0 | + | + | + | + | + | + | + |
| Streptomycin | 2 | + | + | + | + | + | 0 | 0 | + | 0 | 0 | 0 | 0 | 0 | 0 |
| (1:2 dilution) | 3 | + | + | + | + | + | 0 | 0 | 0 | 0 | + | 0 | 0 | 0 | 0 |
| SPLV- | | | | | | | | | | | | | | | |
| encapsulated | 1 | + | + | + | + | + | + | + | 0 | 0 | 0 | 0 | 0 | 0 | 0 |
| Streptomycin | 2 | + | + | + | + | + | + | 0 | 0 | 0 | + | 0 | 0 | 0 | 0 |
| (1:4 dilution) | 3 | + | + | + | + | + | 0 | 0 | + | + | + | + | + | + | + |
| SPLV- | | | | | | | | | | | | | | | |
| encapsulated | 1 | + | + | + | + | + | 0 | 0 | + | + | + | + | + | + | + |
| Streptomycin | 2 | + | + | + | + | + | 0 | 0 | 0 | 0 | 0 | 0 | 0 | 0 | 0 |
| (1:6 dilution) | 3 | + | + | + | + | + | + | + | + | 0 | + | + | + | + | + |

[a]All animals inoculated with $1 \times 10^6$ CFU *M. bovis* by injection into conjunctival membranes of both eyes. Conjunctival swabbings were plated on blood agar. Cultures scored for presence of *M. bovis* colonies on blood agar plates after 24 hours at 37° C.; + = greater than or equal to 1 CFU; 0 = no detectable cultures.

TABLE XXVI

RESULTS FROM NECROPSY OF THE ORBIT AND ASSOCIATED TISSUES FROM RABBITS AFTER INOCULATION WITH *M. BOVIS* INTO CONJUNCTIVAL TISSUES AND TREATMENT WITH EITHER MLV-ENCAPSULATED STREPTOMYCIN, SPLV-ENCAPSULATED STREPTOMYCIN OR DILUTIONS OF SPLV-ENCAPSULATED STREPTOMYCIN[a]

| | Animal | Isolation of *M. Bovis* | Vascularization of Eyes[b] | Lacrimal Discharge[c] |
|---|---|---|---|---|
| Control | 1 | + | 1+ | 1+ |
| | 2 | + | 1+ | 1+ |
| MLV- | | | | |
| encapsulated | 1 | + | 1+ | 1+ |
| Streptomycin | 2 | 0 | 1+ | 0 |
| SPLV- | | | | |
| encapsulated | 1 | 0 | 0 | 0 |
| Streptomycin | 2 | 0 | 1+ | 0 |
| (undiluted) | 3 | 0 | 0 | 0 |
| SPLV- | | | | |
| encapsulated | 1 | + | 2+ | 2+ |
| Streptomycin | 2 | 0 | 0 | 0 |
| (1:2 dilution) | 3 | 0 | 1+ | 0 |
| SPLV- | | | | |
| encapsulated | 1 | 0 | 0 | 0 |
| Streptomycin | 2 | 0 | 1+ | 0 |
| (1:4 dilution) | 3 | + | 1+ | 0 |
| SPLV- | | | | |
| encapsulated | 1 | + | 1+ | 1+ |
| Streptomycin | 2 | 0 | 1+ | 0 |
| (1:6 dilution) | 3 | + | 1+ | 0 |

TABLE XXVI-continued

RESULTS FROM NECROPSY OF THE ORBIT AND ASSOCIATED TISSUES FROM RABBITS AFTER INOCULATION WITH *M. BOVIS* INTO CONJUNCTIVAL TISSUES AND TREATMENT WITH EITHER MLV-ENCAPSULATED STREPTOMYCIN, SPLV-ENCAPSULATED STREPTOMYCIN OR DILUTIONS OF SPLV-ENCAPSULATED STREPTOMYCIN[a]

[a]Legends are same as Table XXV, performed on day 14 post-infection.
[b]Vascularization scored as follows: 0 = vessels normal; 1 = some vessels dilated and infiltrated by minor vessels; 2 = diffuse red with individual vessels not easily discernable; 3 = diffuse beefy red, vascular leakage and effusion of blood into conjunctivae.
[c]Discharge scored as follows: 0 = no discharge; 1 = discharge with moistening of lids and hairs adjacent to lids; 2 = discharge with moistening of lids, hairs and areas adjacent to eyes.

The suspensions were administered topically into each eye. After 24 hours, conjunctival swabbings were taken from all rabbits daily for 9 days and plated onto blood agar. The results of isolation for *M. bovis* on blood agar plates are shown in Table XXV. Necropsies were performed on all animals. These were scored for lacrimal secretions, and conjunctivae were removed aseptically from all animals. These were scored for vascularization, and were minced, homogenized and plated onto blood agar plates for isolation of *M. bovis*. Results are shown in Table XXVI.

12 EXAMPLE: TREATMENT OF VIRAL INFECTIONS

Lymphocytic choriomeningitis virus (LCMV), a member of the Arenavirus group, is known to cause diseases in man and LCMV infection is fatal in mice inoculated intracerebrally with this virus. The death of mice is caused by the immune cells which react against virus-infected cells. The virus does not kill the cells in which it multiplies, therefore, the therapeutic agent used in mice must either inhibit virus multiplication so that the immune cells will not be activated, and/or inhibit the activation of immune cells.

The following example demonstrates the effectiveness of treating viral infections by administering a SPLV-encapsulated antiviral compound.

12.1. Treatment of Lethal Lymphocytic Chorio-Meningitis Virus Infections in Mice Swiss mice 2 months of age were inoculated intracerebrally with a lethal dose of LCM virus, i.e., 100 plaque forming units (PFU) in 0.05 ml inoculum per mouse. Mice were divided into 4 groups of 7 animals each and were treated on days 2, 3 and 4 post-infection by intraperitoneal injections with 0.1 ml/dose/mouse as follows: (1) the "SPLV-R group" was treated with a suspension of egg phosphatidylcholine SPLVs containing 3 mg Ribavarin/ml. SPLVs were prepared using 100 mg lipids and 0.3 ml of 100 mg drug/ml in PBS buffer; the entrapment of drug was 10%; (2) the "R-group" was treated with a solution of Ribavarin 3 mg/m±in PBS; (3) the "SPLV-group" was treated with bufferfilled SPLVs (i.e., SPLVs prepared as above but without Ribavarin); and (4) the "control group" was treated with PBS. On day 5 post-infection 2 mice from each group were sacrificed and their spleens homogenized (2 spleens/group were homogenized in PBS at 1/20 weight per volume buffer). The plaque forming units (PFU) per ml were determined for each suspension. The remaining 5 mice in each groups were observed for lethality two times daily for 30 days. The results are presented in Table XXVII.

TABLE XXVII
TREATMENT OF LETHAL LCM VIRUS INFECTION IN MICE[a]

| Group | Lethality[c] | Virus Recovered from Spleen (PFU × $10^5$/ml)[c] |
|---|---|---|
| Control | 5/5 | 7.0 |
| SPLV-group | 5/5 | 6.9 |
| R-group | 5/5 | 5.2 |
| SPLV-R-Group | 3/5 | 3.4 |

[a]Two month old mice were each inoculated intracerebrally with a lethal dose, i.e., 100 PFU of LCM virus in 0.05 ml inocula.
[b]Lethality is expressed as number dead/number in group.
[c]On the fifth day post-infection 2 mice from each group were sacrificed and their spleens homogenized at a concentration of 1 gm spleen/20 ml homogenate.

Table XXVII clearly indicates a decrease in lethality and a decrease in the virus recoverable from the infected animals. We have not y et determined whether these results are due to the anti-viral activity of the ribavarin which is released from the SPLVs or whether it is due to an immunomodulation of the mouse host during the sustained release of ribavarin from the SPLVs.

13. EXAMPLE: ENHANCEMENT OF ANTIBACTERIAL ACTIVITY IN TREATING CORYNEBACTERIUM RENALE PYELONEPHRITIS USING SPLVS CONTAINING GENTAMICIN AND NAFCILLIN

In this example, the antibacterial activity and clinical effectiveness of various preparations of gentamicin and nafcillin are compared. The results indicate that of the preparations tested, treatment of *Corynebacterium renale* pyelonephritis is most effective when using an SPLV preperation in which gentamicin and nafcillin are both incorporated into one liposome preparation.

13.1 Preparation of SPLVs

The SPLVs containing either gentamicin or nafcillin or both were prepared as described in Section 6.2.

13.2 Infection of Mice Using Corynebacterium Renale

A *Corynebacterium renale* pyelonephritis was induced in adult Hilltop mice (20–30 gm each) essentially by the method of Shumono and Yanagawa (Infection and Immunity, April 1977, pp. 263–67) as follows: each mouse was anesthetized using ether, the abdominal wall was incised and the bladder isolated. The bladder contents were evacuated by applying gentle pressure. A suspension of *C. renale* in BHI (Blood, Heart Infusion medium, BBL Microbiological Systems, Cockeysville, Md.) at a concentration of $10^7$ CFU (colony forming units) per ml was inoculated into the bladder until full (approximately 0.1 to 0.2 ml per injection or $10^6$ organisms per mouse bladder). The abdominal wall was then closed. The *C. renale* had been prepared by growing *C. renale* ATCC strain No. 10848 overnight in BHI broth. Organisms were then suspended in saline to an O.D.420 of approximately 0.78. Serial dilutions were plated on agar in order to determine the CFU per ml for each dilution.

13.3. Treatment of Infected Mice

Twenty four hours after inoculation with *C. renale* the mice were divided into 7 groups and each group was treated as follows: Group 1 (controls) received no treatment; Group 2 received aqueous gentamicin (100 mg/kg body weight, I.P.); Group 3 received SPLVs containing gentamicin (100 mg/kg body weight, I.P.); Group 4 received aqueous nafcillin (100 mg/kg body weight, I.P.); Group 5 received SPLVs containing nafcillin (100 mg/kg body weight, I.P.); Group 6 received a single aqueous preparation containing both gentamicin (100 mg/kg body weight) and nafcillin (100 mg/kg body weight) I.P ; and Group 7 received one SPLV preparation containing both gentamicin (100 mg/kg body weight) and nafcillin (100 mg/kg body weight) I.P. Results are shown in Table XXVIII. 7 The results in Table XXVIII clearly indicate that the SPLVs containing both gentamicin and nafcillin were most effective in preventing mortality due to *C. renale* pyelonephritis.

In another set of experiments, the effectiveness of gentamicin and nafcillin entrapped in one SPLV preparation was also compared to the effectiveness of administering the two drugs separately contained in SPLVs. Accordingly, mice were infected with *C. renale* as described in Section 13.2. Twenty-four hours after inoculation with *C. renale* the mice were divided into 4 groups and each group was treated as follows: Group 1 (control) received no treatment; Group 2 received aqueous nafcillin (100 mg/kg body weight, I.P.) followed by aqueous gentamicin (100 mg/kg body weight, I.P.) administered 1 hour after the nafcillin (NAF-GENT, aq.; N.B., the aqueous preparations of nafcillin and gentamicin were administered one hour apart in order to prevent in situ inactivation of the drugs); Group 3 received a mixture of two SPLV preparations, one containing gentamicin (SPLV-GENT; 100 mg/kg body weight) and the other SPLV preparation containing nafcillin (SPLV-NAF; 100 mg/kg body weight) I.P.; and Group 4 received a SPLV preparation (SPLV/GENT-NAF) containing both gentamicin (100 mg/kg body weight) and nafcillin (100 mg/kg body weight) I.P. The results shown in Table XXIX demonstrate that the SPLV/GENT-NAF preparation was the most effective in treating the infection.

TABLE XXVIII
EFFECT OF SPLV ENTRAPPED GENTAMYCIN AND NAFCILLIN ON *C. RENALE* PYELONEPHRITIS IN MICE

| GROUP[a] | SURVIVAL DAYS AFTER TREATMENT | | | | | | | % SURVIVAL |
|---|---|---|---|---|---|---|---|---|
| | 1 | 2 | 3 | 4 | 5 | 6 | 7 | |
| GROUP 1 CONTROLS (untreated) | 15/15 | 15/15 | 7/15 | 1/15 | 1/15 | 0/15 | 0/15 | 0 |
| GROUP 2 GENTAMYCIN (100 mg/kg) | 10/10 | 10/10 | 4/10 | 1/10 | 10/10 | 1/10 | 1/10 | 10 |
| GROUP 3 SPLV-GENT (100 mg/kg) | 10/10 | 10/10 | 10/10 | 5/10 | 5/10 | 3/10 | 0/10 | 0 |
| GROUP 4 NAFCILLIN (100 mg/kg) | 10/10 | 10/10 | 7/10 | 0/10 | 0/10 | 0/10 | 0/10 | 0 |
| GROUP 5 SPLV-NAF (100 mg/kg) | 10/10 | 10/10 | 5/10 | 0/10 | 0/10 | 0/10 | 0/10 | 0 |
| GROUP 6 (aq.) GENT/NAF (100 mg/kg each) | 10/10 | 10/10 | 8/10 | 0/10 | 0/10 | 0/10 | 0/10 | 0 |
| GROUP 7 SPLV-GENT/NAF (100 mg/kg each) | 10/10 | 10/10 | 10/10 | 10/10 | 10/10 | 10/10 | 10/10 | 100 |

[a]All mice were treated by intraperitoneal injection 24 hours after infection.

TABLE XXIX
EFFECT OF SPLV ENTRAPPED GENTAMICIN AND NAFCILLIN ON *C. RENALE* PYELONEPHRITIS IN MICE

| GROUP | SURVIVAL DAYS AFTER TREATMENT | | | | | | | % SURVIVAL |
|---|---|---|---|---|---|---|---|---|
| | 1 | 2 | 3 | 4 | 5 | 6-11 | 12-14 | |
| GROUP 1 CONTROLS | ⅛ | 2/8 | ⅛ | 0/8 | 0/8 | 0/8 | 0/8 | 0 |
| GROUP 2 NAF-GENT (aq.) | 10/10 | 10/10 | 1/10 | 0/10 | 0/10 | 0/10 | 0/10 | 0 |
| GROUP 3 SPLV-GENT & SPLV-NAF | 10/10 | 10/10 | 6/10 | 3/10 | 2/10 | 0/10 | 0/10 | 0 |
| GROUP 4 SPLV/GENT/NAF | 9/10 | 9/10 | 9/10 | 9/10 | 9/10 | 9/10 | 8/10 | 80 |

[a]All mice were treated by intraperitoneal injection 24 hours after infection.

The surviving mice which were treated with the SPLV preparation containing both gentamicin and nafcillin were sacrificed at day 14 and the right kidneys were tested for the presence of *C. renale* whereas the left kidneys were analyzed histologically.

The right kidneys were homogenized in BHI media. The homogenate was serially diluted and plated on agar. No growth of organisms was detected in cultures of the right kidneys of the 8 surviving mice. Histologic examination of the left kidney revealed no lesions in ⅝ of the kidneys sampled, minimal to moderate chronic inflammation in the lining of the pelvis of 2 mice, and purulent pyelonephritis with focal necrosis and acute purulent inflammatory reaction in the center left kidney of only 1 mouse. Thus, histologic and bacteriological cure was demonstrated in the surviving animals.

14. EXAMPLE: ENHANCEMENT OF ANTIBACTERIAL ACTIVITY IN TREATING PSEUDOMONAS AERUGINOSA PYELONEPHRITIS USING SPLVS CONTAINING TOBRAMYCIN AND TICARCILLIN

In this example, the antibacterial activity and clinical effectiveness of various preparations of tobramycin (an aminoglycoside antibiotic) and ticarcillin (a β-lactam antibiotic) are compared. The results indicate that of the preparations tested, treatment of *Pseudomonas aeruginosa* pyelonephritis is most effective when using an SPLV preparation in which tobramycin and ticarcillin are both incorporated into one liposome preparation.

SPLVs containing both tobramycin and ticarcillin were prepared by the monophasic solvent system method as follows: a 10 ml ethanol solution of 100 mg EPC was prepared in a round bottom flask. Then 100 mg ticarcillin in 1.5 ml PBS was added to the EPC ethanol solution to which 100 mg tobramycin in 0.5 ml PBS lacking divalent cations (PBS−) was added. The resulting mixture (a dispersion) was evaporated at 54° C. for 3 minutes until a film formed on the side of the vessel. Then 10 ml of PBS was added and the mixture was agitated to form and resuspend the SPLVs.

SPLVs containing either tobramycin or ticarcillin were prepared as described above except that 100 mg of either tobramycin or 100 mg of ticarcillin in PBS was added to the EPC ethanol solution.

14.1. Treatment of Infected Rats

Sprague Dawley rats (approximately 0.2 kg each) were infected with *P. aeruginosa* by the following technique: female rats were anesthetized using Brevital (10.64 mg/200 gm rat) administered subcutaneously. The urinary bladder was exposed by a midline incision made after shaving the abdomen. A small incision was made in the bladder and all urine was drained after which a zinc pellet (3 mm in diameter) was inserted into the bladder. The bladder incision was tied off using size 000 black braided Type B silk thread and a 0.1 ml inoculum of *P. aeruginosa* culture which was grown overnight in TSB (Trypticase Soy Broth, BBL Microbiological Systems, Cockeysville, Md.) was injected into the bladder. The abdominal incision was then closed using stainless steel clamps on the abdominal muscle and on the skin.

Infected rats were divided into 5 groups which were treated with two doses of the following preparations administered intraperitoneally at 4 and 28 hours after inoculation with *P. aeruginosa*: Group 1 (controls) received no treatment; Group 2 received aqueous tobramycin (4 mg/kg body weight); Group 3 received SPLVs containing tobramycin (4 mg/kg body weight); Group 4 received aqueous tobramycin (400 mg/kg body weight); and Group 5 received one SPLV preparation (MPV/TIC-TOBRA) containing both tobramycin (4 mg/kg body weight) and ticarcillin (4 mg/kg body weight).

The surviving rats were sacrificed at day 6 and each pair of kidneys was tested for the presence of *P. aeruginosa* as follows: after each kidney was removed, it was placed on a petri dish containing ethanol, flamed and then homogenized in 2 ml TSB. The homogenate was adjusted to final volume of 10 ml using TSB. Serial 10-fold dilutions of the homogenate were plated in duplicate on agar, and the CFU/ml were determined for each pair of kidneys. Results are shown in Table XXX.

TABLE XXX

EFFECT OF SPLV ENTRAPPED TOBRAMYCIN AND TICARCILLIN ON *P. AERUGINOSA* PYELONEPHRITIS IN RATS

| GROUP | SURVIVORS 6 DAYS POST INFECTION | $LOG_{10}$ CFU OF *P. AERUGINOSA* RECOVERED IN KIDNEY HOMOGENATE RAT | | | | | | |
|---|---|---|---|---|---|---|---|---|
| | | 1 | 2 | 3 | 4 | 5 | 6 | 7 |
| GROUP 1 CONTROLS (untreated) | 5/7 | 6 | 4 | 4 | 5 | 8 | ND | ND |
| GROUP 2 TOBRAMYCIN (aq.) (4 mg/kg) | 7/7 | 4 | 3 | 4 | 0 | 0 | 4 | 0 |
| GROUP 3 SPLV-TOBRA (4 mg/kg) | 4/7 | 3 | 7 | 4 | 0 | ND | ND | ND |
| GROUP 4 TICARCILLIN TOBRAMYCIN (aq.) (4 mg/kg - 400 mg/kg) | 5/7 | 2 | 5 | 4 | 0 | 0 | ND | ND |
| GROUP 5 SPLV/TIC-TOBRA (400 mg/kg - 4 mg/kg) | 7/7 | 0 | 0 | 0 | 0 | 0 | 4 | 0 |

These results indicate that the combination of tobramycin and ticarcillin contained in one SPLV preparation was most effective in the treatment of Pseudomonas pyelonephritis.

14.2. Effects of Different Treatments of Infected Rats

Female Sprague-Dawley rats were infected with *P. aeruginosa* as described above, and treated with various SPLV-drug combinations as listed in Tables XXXI to XXXIV. The animals were observed daily for the 6 day treatment period and any dead animals were removed from the cages and recorded. Four hours after the final treatment on day 6, the animals were sacrificed. Both kidneys were removed by aseptic technique placed on a petri dish containing ethanol, flamed, and then homogenized in 2.0 ml TSB. Each pair of kidneys was homogenized in 4 ml TSB and then diluted with 4 ml of media ($10^{-1}$ dilution). TS (Trypticase Soy) agar plate counts of the homogenized kidneys were made for each animal and compared with the plate counts made on the diluent treated control group. Dilutions for untreated controls: $10^{-1}$, $10^{-2}$, $10^{-3}$, $10^{-4}$, $10^{-5}$, $10^{-6}$, $10^{-7}$. Dilutions for treated kidney homogenates: $10^{-1}$, $10^{-2}$, $10^{-3}$, $10^{-4}$, $10^{-5}$, $10^{-6}$, $10^{-7}$. Results are presented in Tables XXXI to XXXIV, below.

TABLE XXXI

EFFECT OF SPLV-ENTRAPPED TOBRAMYCIN
ADMINISTERED INTRAPERTONEALLY
ON *P. AERUGA* PYELONEPHRITIS IN RATS

| EXPERIMENTAL GROUP | I.P.[a] PER DAY (mg/kg) | # ANIMALS IN GROUP | # DEATHS | # CLEARED OF INFECTION | MEAN TITER OF INFECTED ANIMALS | % CLEARED OF INFECTION |
|---|---|---|---|---|---|---|
| CONTROLS (UNINFECTED/ UNTREATED) | — | 110 | 18 | 4 | $10^5$–$10^6$ | 4.3 |
| FREE TOBRAMYCIN | 4 | 16 | 2 | 4 | $10^4$–$10^5$ | 28.6 |
|  | 2 | 7 | 2 | 0 | $10^4$–$10^5$ | 0 |
|  | 1 | 7 | 1 | 1 | $10^5$–$10^6$ | 17.0 |
|  | 0.5 | 7 | 0 | 0 | $10^5$–$10^6$ | 0 |
|  | 0.25 | 7 | 1 | 1 | $10^4$–$10^5$ | 13.8 |
| SPLV-TOBRAMYCIN | 4 | 40 | 3 | 37 | 0 | 100.00 |
|  | 2 | 28 | 2 | 25 | 0 | 96.1 |
|  | 1 | 35 | 5 | 23 | $10^1$ | 65.7 |
|  | 0.5 | 14 | 3 | 7 | $10^4$ | 70.0 |
|  | 0.25 | 15 | 2 | 8 | $10^5$–$10^7$ | 61.5 |

[a]Six daily intraperitoneal doses.

Table XXXI clearly shows the superiority of SPLV entrapped tobramycin in clearing infection due to *P. aeruginosa* in a single daily dose regimen. The SPLV-entrapped tobramycin was 10 times more effective than free drug alone.

Table XXXII clearly shows the superiority of SPLV entrapped ticarcillin in clearing infection due to *P. aeruginosa* in a single daily dose regimen. The SPLV-entrapped ticarcillin was 30 times more effective than free drug alone.

TABLE XXXII

EFFECT OF SPLV-ENTRAPPED TICARCILLIN
ADMINISTERED INTRAPERITONEALLY
ON *P. AERUGINOSA* PYELONEPHRITIS IN RATS

| EXPERIMENTAL GROUP | I.P.[a] PER DAY (mg/kg) | # ANIMALS IN GROUP | # DEATHS | # CLEARED OF INFECTION | MEAN TITER OF INFECTED ANIMALS | % CLEARED OF INFECTION |
|---|---|---|---|---|---|---|
| CONTROLS (UNINFECTED/ UNTREATED) | — | 110 | 18 | 4 | $10^5$–$10^6$ | 4.3 |
| FREE TICARCILLIN | 400 | 9 | 0 | 8 | $10^6$ | 89.0 |
|  | 200 | 7 | 1 | 0 | $10^4$–$10^5$ | 0 |
|  | 100 | 7 | 2 | 1 | $10^5$–$10^6$ | 16.6 |
|  | 50 | 7 | 0 | 1 | $10^4$–$10^5$ | 14.3 |
| SPLV-TICARCILLIN | 50 | 9 | 1 | 8 | 0 | 100.00 |
|  | 25 | 27 | 5 | 22 | 0 | 100.00 |
|  | 12.5 | 28 | 0 | 26 | $10^6$ | 92.9 |
|  | 6.25 | 28 | 0 | 22 | $10^5$ | 78.6 |
|  | 3.67 | 7 | 1 | 1 | $10^6$–$10^8$ | 16.7 |

[a]Six daily intraperitoneal doses.

TABLE XXXIII

EFFECT OF SPLV-ENTRAPPED TOBRAMYCIN
ADMINISTERED INTRAPERITONEALLY
ON *P. AERUGINOSA* PYELONEPHRITIS IN RATS

| EXPERIMENTAL GROUP | I.P.[a] PER DAY (mg/kg) | # ANIMALS IN GROUP | # DEATHS | # CLEARED OF INFECTION | MEAN TITER OF INFECTED ANIMALS | % CLEARED OF INFECTION |
|---|---|---|---|---|---|---|
| CONTROLS (INFECTED/ UNTREATED) | — | 110 | 18 | 4 | $10^5$–$10^6$ | 4.3 |
| CONTROLS (UNINFECTED/ UNTREATED) | — | 7 | 0 | N.A.[a] | 0 | N.A.[a] |
| FREE TOBRAMYCIN IP (6 Dosages) | 4 | 16 | 2 | 4 | $10^4$–$10^5$ | 28.6 |
| SPLV-TOBRAMYCIN (IP 6 Dosages) | 4 | 40 | 3 | 37 | 0 | 100.00 |
| BUFFER Filled SPLVs IP (6 Dosages) | — | 7 | 0 | 2 | $10^5$–$10^6$ | 28.5 |
| BUFFER Filled SPLVs and Free Tobramycin | 4 | 7 | 0 | 1 | $10^4$ | 14.3 |

TABLE XXXIII-continued

EFFECT OF SPLV-ENTRAPPED TOBRAMYCIN
ADMINISTERED INTRAPERITONEALLY
ON P. AERUGINOSA PYELONEPHRITIS IN RATS

| EXPERIMENTAL GROUP | I.P.[a] PER DAY (mg/kg) | # ANIMALS IN GROUP | # DEATHS | # CLEARED OF INFECTION | MEAN TITER OF INFECTED ANIMALS | % CLEARED OF INFECTION |
|---|---|---|---|---|---|---|
| IP (6 Dosages) | | | | | | |

[a] Not applicable.

Table XXXIII shows neither SPLVs alone nore SPLVs mixed with aqueous tobramycin were as effective in eliminating infection as tobramycin entrapped within SPLVs. The efficacy of SPLVs alone or SPLVs mixed with tobramycin were only as effective as aqueous tobramycin alone.

15. EXAMPLE: ENHANCEMENT OF ANTIBACTERIAL ACTIVITY AGAINST CLOSTRIDIUM NOVYI USING SPLVS CONTAINING GENTAMICIN AND CLINDAMYCIN

TABLE XXXIV

EFFECT OF SPLV-ENTRAPPED TOBRAMYCIN
ADMINISTERED INTRAVENOUSLY
ON P. AERUGINOSA PYELONEPHRITIS IN RATS

| EXPERIMENTAL GROUP | I.P.[a] PER DAY (mg/kg) | # ANIMALS IN GROUP | # DEATHS | # CLEARED OF INFECTION | MEAN TITER OF INFECTED ANIMALS | % CLEARED OF INFECTION |
|---|---|---|---|---|---|---|
| CONTROLS (INFECTED/ UNTREATED) | — | 110 | 18 | 4 | $10^5$–$10^6$ | 4.3 |
| FREE TOBRAMYCIN | 32 | 16 | 0 | 9 | $10^5$–$10^6$ | 56.2 |
| | 16 | 7 | 1 | 1 | $10^3$–$10^4$ | 16.7 |
| | 4 | 14 | 1 | 2 | $10^5$–$10^6$ | 15.4 |
| SPLV-TOBRAMYCIN | 32 | 14 | 0 | 14 | 0 | 100.00 |
| | 16 | 26 | 3 | 18 | 0 | 100.00 |
| | 8 | 28 | 3 | 10 | $10^4$–$10^5$ | 40.0 |
| | 4 | 35 | 7 | 6 | $10^5$–$10^6$ | 21.4 |

[a] One intravenous dose.

Table XXXIV shows that SPLV entrapped tobramycin was three times more effective in eliminating infection for equivalent single doses when compared with aqueous tobramycin administered intravenously.

In this example, the antibacterial activity and clinical effectiveness of various preparations of gentamicin (an aminoglycoside antibiotic) and clindamycin (a derivative of the amino acid trans-L-4-n prophylhygrinic acid

TABLE XXXV

EFFECT OF SPLV-ENTRAPPED TOBRAMYCIN
ADMINISTERED BY VARIOUS ROUTES
ON P. AERUGINOSA PYELONEPHRITIS IN RATS

| EXPERIMENTAL GROUP | I.P.[a] PER DAY (mg/kg) | # ANIMALS IN GROUP | # DEATHS | # CLEARED OF INFECTION | MEAN TITER OF INFECTED ANIMALS | % CLEARED OF INFECTION |
|---|---|---|---|---|---|---|
| CONTROLS (INFECTED/ UNTREATED) | — | 110 | 18 | 2 | $10^5$–$10^6$ | 4.3 |
| FREE TOBRAMYCIN | 16 | 7 | 1 | 1 | $10^3$–$10^4$ | 16.7 |
| SPLV-TOBRAMYCIN | | | | | | |
| Intravenous | 16 | 28 | 4 | 22 | $10^4$ | 91.7 |
| Intraperitoneal | 16 | 7 | 0 | 6 | $10^2$ | 85.7 |
| Subcutaneous | 16 | 7 | 1 | 1 | $10^4$ | 16.7 |
| Oral | 16 | 7 | 2 | 1 | $10^5$ | 20.0 |

[a] One dose.

Table XXXV demonstrates the efficacy of SPLV-entrapped tobramycin administered by different routes. Intravenous and intraperitoneal injections of SPLV-entrapped tobramycin appear to be the most efficacious.

attached to a sulfur-containing derivative of an octose) in the treatment of anaerobic would infection of Clostridium novyi.

SPLVs containing gentamicin (SPLV/GENT) were prepared as described in Section 7.1 using 100 mg gentamicin. SPLVs containing clindamycin (SPLV/CLIN) were prepared the same way except that 100 mg clindamycin was used in place of the gentamicin. SPLVs containing both gentamicin and clindamycin in one liposome preparation (SPLV/GENT-CLIN) were prepared by the procedure described in Section 7.4 using 100 mg of each antibiotic, gentamicin and clindamycin. All SPLV preparations were washed three times in physiological saline.

15.1. Infection of Mice Using Clostridium Novyi

Twenty Swiss Webster adult female mice were injected in the right rear footpad with 0.05 ml of a suspension of a *Clostridium novyi* prepared as follows: *C. novyi* were grown for one day to stationary phase ($10^8$ to $10^9$ CFU/ml) in BHI media in an anaerobic blood bottle. The inoculum was prepared by diluting the culture 1:100 using fresh degassed BHI media; thus the inoculum contained approximately $10^7$ CFU/ml.

15.2. TREATMENT OF INFECTED MICE

Twenty four hours after infection the mice were divided into 4 groups of 5 mice each which were treated as follows: Group 1 (controls) received no treatment; Group 2 received SPLVs containing gentamicin (100 mg gentamicin/kg body weight, I.P.); Group 3 received SPLVs containing clindamycin (100 mg clindamycin/kg body weight, I.P.); and Group 4 received SPLVs containing both clindamycin and gentamicin in one liposome preparation (100 mg of each antibiotic per kg body weight, I.P.). The diameters of the infected feet were measured using calipers and compared to control mice which were injected only with fresh media. Results are shown on Table XXXVI.

TABLE XXXVI
EFFECT OF SPLVS CONTAINING GENTAMICIN AND CLINDAMYCIN ON CLOSTRIDIUM NOVYI INFECTION IN MICE

| GROUP | MEAN FOOTPAD DIAMETER (INCHES) | SURVIVAL DAYS POST INFECTION | | | | | | % SURVIVAL |
|---|---|---|---|---|---|---|---|---|
| | | 1 | 2 | 3 | 4 | 5 | 6-19 | |
| GROUP 1 Control Untreated | 0.167 | 0/5 | 0/5 | 0/5 | 0/5 | 0/5 | 0/5 | 0% |
| GROUP 2 SPLV/GENT | 0.177 | 5/5 | 3/5 | 0/5 | 0/5 | 0/5 | 0/5 | 0% |
| GROUP 3 SPLV/CLIN | 0.177 | 5/5 | 1/5 | 1/5 | 0/5 | 0/5 | 0/5 | 0% |
| GROUP 4 SPLV/ GENT-CLIN | 0.166 | 5/5 | 4/5 | 4/5 | 4/5 | 4/5 | 3/5 | 60% |

[1]The mean footpad diameter of uninfected mice inoculated with fresh media is 0.119.

These results demonstrate that SPLVs containing both gentamicin and clindamycin in one liposome preparation were most effective in the treatment of the anaerobic infection of the wounds.

It will be apparent to those skilled in the art that many modifications and variations may be made without departing from the spirit and scope of the invention. The specific embodiments described are given by way of example only and the invention is limited only by the appended claims.

What is claimed is:

1. Stable plurilamellar vesicles comprising lipid vesicles comprising a plurality of lipid bilayers enclosing aqueous compartments containing at least one entrapped solute, the concentration of such solute in each aqueous compartment being substantially equal to the concentration of solute used to prepare the lipid vesicles, the lipid bilayers dividing each such aqueous compartment being substantially non-compressed, so that the $^{31}$p-NMR signal of stable plurilamellar vesicles prepared and susended in buffer containing $Mn^{++}$ is more strongly quenched that that of MLVs prepared and suspended in buffer containing $Mn^{++}$.

2. Stable plurilamellar vesicles comprising a plurality of lipid bilayers enclosing aqueous compartments containing at least one entrapped solute, the concentration of such solute in each compartment being substantially equal to the concentration of solute used to prepare the lipid vesicle.

3. Stable plurilamellar vesicles comprising lipid vesicles comprising a plurality of lipid bilayers enclosing aqueous compartments containing at least one entrapped solute, the concentration of such solute in each aqueous compartment being substantially equal to the concentration of solute used to prepare the lipid vesicles, the lipid bilayers dividing each such aqueous compartment being substantially non-compressed, so that the lipid vesicles have a characteristic Long Spacing Signature, a Bragg Peak Signature and a Wide-angle X-ray Signature as determined by X-ray diffraction of the lipid vesicles suspended in an aqueous medium that is isosmotic to the aqueous medium used to prepare the lipid vesicles.

4. The stable plurilamellar vesicles of claim 3 in which the lipid bilayers comprise only zwitterionic lipids and in which the Long Spacing Signature of the stable plurilamellar vesicles suspended in an aqueous medium that is isosmotic to the aqueous medium used to prepare the stable plurilamellar vesicles appears substantially as depicted for stable plurilamellar vesicles in FIG. 4, in which the Long Spacing Signature is obtained by plotting the mean long repeat spacing of the lamellar lattice as determined by small angle X-ray diffractions the temperature is varied from 0° C. to 40° C.

5. The stable plurilamellar vesicles of claim 3 in which the lipid bilayers comprise only zwitterionic lipids and in which the Bragg Peak Signature of the stable plurilamellar vesicles suspended in an aqueous medium that is isosmotic to the aqueous medium used to prepare the stable plurilamellar vesicles appears substantially as depicted in FIG. 5b or FIG. 5c, in which the width and asymmetry of the distribution of membrane repeat spacings as obtained by low angle X-ray diffraction at a temperature of 40° C. are determined by the least square fit to the peak positions of the Bragg orders where the peak positions are taken as the centers of parabolas least-square fit to the peak profiles, and where the angle of diffraction, 2θ, for a given order, n, follows from the Bragg relation:

$n\lambda = 2D \sin \theta$ where $\lambda$ = X-ray wavelength and

D = repeat spacing of the lattice.

6. The stable plurilamellar vesicles of claim 3 in which the lipid bilayers comprise only zwitterionic lipids and in which the Wide-angle X-ray Signature of the stable plurilamellar vesicles suspended in an aqueous medium that is isosmotic to the aqueous medium used to prepare the stable plurilamellar vesicles appears substantially as depicted for stable plurilamellar vesicles in FIG. 6a or FIG. 6b, in which the Wide-angle Signature as determined at a temperature of 10° C. by X-ray diffraction in the wide angle regime is obtained by plotting the X-ray intensity versus $S^{-1}$ (Å) and $\lambda/20$ 10Å where $\lambda$ = X-ray wavelength, and $2\theta$ = the angle of diffraction.

7. Stable plurilamellar vesicles comprising lipid vesicles comprising a plurality of lipid bilayers enclosing aqueous compartments containing at least one entrapped solute, the concentration of such solute in each aqueous compartment being substantially equal to the concentration of solute used to prepare the lipid vesicles, the lipid bilayers dividing each such aqueous compartment being substantially non-compressed, so that the lipid vesicles have a characteristic Long Spacing Signature, a Bragg Peak Signature and a Wide-angle X-ray Signature as determined by X-ray diffraction of the lipid vesicles suspended in an aqueous medium that is isosmotic to the aqueous medium used to prepare the lipid vesicles; and in which (a) the Long Spacing Signature of such stable plurilamellar vesicles composed of zwitterionic lipid bilayers suspended in an aqueous medium that is isosmotic to the aqueous medium used to prepare the stable plurilamellar vesicles appears substantially as depicted for stable plurilamellar vesicles in FIG. 4, in which the Long Spacing Signature is obtained by plotting the mean repeat spacing as determined by low angle X-ray diffraction which is a measure of the sum of the thicknesses of a bilayer and an interbilayer aqueous space versus temperature which is varied from 0° C. to 40° C.; and (b) the Bragg Peak Signature of such stable plurilamellar vesicles composed of zwitterionic lipid bilayers suspended in an aqueous medium that is isosmotic to the aqueous medium used to prepare the stable plurilamellar vesicles appears substantially as depicted in FIG. 5b or FIG. 5c, in which the width and asymmetry of the distribution of membrane repeat spacings as obtained by low angle X-ray diffraction at a temperature of 40° C. are determined by the least square fit to the peak positions of the Bragg orders where the peak positions are taken as the centers of parabolas least-square fit to the peak profiles, and where the angle of diffraction, $2\theta$, for a given order, n, follows from the Bragg relation:

$n\lambda = 2D \sin \theta$ where $\lambda$ = X-ray wavelength, and

D = repeat spacing of the lattice; and (c) the Wide-angle X-ray Signature of such stable plurilamellar vesicles composed of zwitterionic lipid bilayers and suspended in an aqueous medium that is isosmotic to the aqueous medium used to prepare the stable plurilamellar vesicles appears substantially as depicted for stable plurilamellar vesicles in FIG. 6a or FIG. 6b, in which the Wide-angle Signature as determined at a temperature of 10° C. by X-ray diffraction in the wide angle regime is obtained by plotting the X-ray intensity versus $S^{-1}$ (Å)

$\lambda/20$ 10Å where = X-ray wavelength, and $2\theta$ = the angle of diffraction.

8. Stable plurilamellar vesicles according to claim 3 or 7, having a lower buoyant density and a volume about one-third larger than MLVs, made from the same components.

9. Stable plurilamellar vesicles according to claim 3 or 7, which are more stable to auto-oxidation during storage in buffer than are MLVs, made from the same components.

10. Stable plurilamellar vesicles according to claim 3 or 7, which release entrapped compounds when exposed to urea.

11. Stable plurilamellar vesicles according to claim 3 or 7, which, when administered intraperitoneally or intravenously in vivo, slowly release any entrapped compounds.

12. Stable plurilamellar vesicles according to claim 3 or 7, which, when administered to cells in culture, the contents of the vesicles are distributed throughout the cytosol of the cells.

13. Stable plurilamellar vesicles according to claim 3 or 7, which, when administered to cells in vivo, both the lipid and aqueous components of the vesicles are retained in the tissues and by the cells.

14. Stable plurilamellar vesicles according to claim 3, 4, 5, 6, 7 or 2, in which the major lipid component of the vesicles is a phosphatidylcholine.

15. Stable plurilamellar vesicles according to claim 3, 4, 5, 6, 7 or 2, in which an anti-oxidant is a component of the vesicle.

16. Stable plurilamellar vesicles according to claim 15, in which said anti-oxidant is butylated hydroxytoluene.

17. Stable plurilamellar vesicles according to claim 3, 4, 5, 6, 7 or 2, in which a protein is entrapped within the vesicle.

18. Stable plurilamellar vesicles according to claim 3, 4, 5, 6, 7 or 2, in which antibacterial compound, antifungal compound, antiparasitic compound, or antiviral compound is entrapped within the vesicle.

19. Stable plurilamellar vesicles according to claim 3, 4, 5, 6, 7 or 2, in which a tumoricidal compound, toxin, cell receptor binding molecule, or immunoglobulin is entrapped within the vesicle.

20. Stable plurilamellar vesicles according to claim 3, 4, 5, 6, 7 or 2, in which an anti-inflammatory compound, anti-glaucoma compound, mydriatic compound, or local anesthetic is entrapped within the vesicle.

21. Stable plurilamellar vesicles according to claim 3, 4, 5, 6, 7 or 2, in which an enzyme, hormone, neurotransmitter, immunomodulator, nucleotide, or cyclic adenosine monophosphate is entrapped within the vesicle.

22. Stable plurilamellar vesicles according to claim 3, 4, 5, 6, 7 or 2, in which a dye, fluorescent compound, radioactive compound, or radio-opaque compound is entrapped within the vesicle.

23. Stable plurilamellar vesicles according to claim 3, 4, 5, 6, 7 or 2, in which a cosmetic preparation, a fragrance or a flavor is entrapped within the vesicle.

* * * * *